United States Patent
Boyden et al.

(10) Patent No.: US 9,011,510 B2
(45) Date of Patent: *Apr. 21, 2015

(54) METHOD, DEVICE AND SYSTEM FOR MODULATING AN ACTIVITY OF BROWN ADIPOSE TISSUE IN A VERTEBRATE SUBJECT

(75) Inventors: Edward S. Boyden, Chestnut Hill, MA (US); Roderick A. Hyde, Redmond, WA (US); Muriel Y. Ishikawa, Livermore, CA (US); Edward K. Y. Jung, Bellevue, WA (US); Eric C. Leuthardt, St. Louis, MO (US); Stephen L. Malaska, Redmond, WA (US); Elizabeth A. Sweeney, Seattle, WA (US); Lowell L. Wood, Jr., Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 989 days.

This patent is subject to a terminal disclaimer.

(21) Appl. No.: 13/068,422

(22) Filed: May 9, 2011

(65) Prior Publication Data

US 2012/0289757 A1 Nov. 15, 2012

Related U.S. Application Data

(63) Continuation-in-part of application No. 13/068,421, filed on May 9, 2011, and a continuation-in-part of application No. 13/068,420, filed on May 9, 2011, now Pat. No. 8,690,934.

(51) Int. Cl.
*A61F 7/12* (2006.01)
*A61F 7/00* (2006.01)

(Continued)

(52) U.S. Cl.
CPC .............. *A61N 1/0534* (2013.01); *A61N 5/025* (2013.01); *A61N 5/04* (2013.01); *A61F 7/12* (2013.01);

(Continued)

(58) Field of Classification Search
USPC ................................... 607/96, 105–106, 113
See application file for complete search history.

(56) References Cited

U.S. PATENT DOCUMENTS 3,977,202 A   8/1976   Forusz et al.
4,100,401 A   7/1978   Tutt et al.

(Continued)

FOREIGN PATENT DOCUMENTS

JP   2008-181998   1/2010
JP   2010-017422   1/2010
WO   WO 03/106966 A2   12/2003

OTHER PUBLICATIONS

PCT International Search Report; International App. No. PCT/US 12/37027; Jul. 24, 2012; pp. 1-2.

(Continued)

*Primary Examiner* — Joseph Stoklosa
*Assistant Examiner* — Adam Avigan

(57) ABSTRACT

Devices, systems, and methods are disclosed herein for treatment of a disease, disorder, or condition in a vertebrate subject. A device is provided that includes one or more cooling elements configured to be applied to one or more tissues of a vertebrate subject to modulate at least one activity of brown adipose tissue of the vertebrate subject, wherein at least a portion of the one or more cooling elements is configured to be implantable, and a programmable controller configured to provide instructions to the one or more cooling elements in response to information regarding one or more physiological conditions of the vertebrate subject.

48 Claims, 11 Drawing Sheets

(51) Int. Cl.
*A61N 1/05* (2006.01)
*A61N 5/02* (2006.01)
*A61N 5/04* (2006.01)
*A61N 1/36* (2006.01)
*A61F 7/10* (2006.01)
*A61F 7/02* (2006.01)

(52) U.S. Cl.
CPC ... *A61F 2007/0075* (2013.01); *A61F 2007/126* (2013.01); *A61N 1/36* (2013.01); *A61F 7/106* (2013.01); *A61N 1/3605* (2013.01); *A61F 2007/0002* (2013.01); *A61F 2007/0056* (2013.01); *A61F 2007/009* (2013.01); *A61F 2007/0093* (2013.01); *A61F 2007/029* (2013.01); *A61F 2007/101* (2013.01)

(56) References Cited

U.S. PATENT DOCUMENTS

| | | | |
|---|---|---|---|
| 4,159,416 | A | 6/1979 | Brejnik et al. |
| 4,312,358 | A | 1/1982 | Barney |
| 4,436,094 | A | 3/1984 | Cerami |
| 4,470,263 | A | 9/1984 | Lehovec et al. |
| 4,829,771 | A | 5/1989 | Koslow et al. |
| 4,953,552 | A | 9/1990 | DeMarzo |
| 5,018,521 | A * | 5/1991 | Campbell ............... 607/98 |
| 5,183,740 | A | 2/1993 | Ligler et al. |
| 5,188,104 | A | 2/1993 | Wernicke et al. |
| 5,263,480 | A | 11/1993 | Wernicke et al. |
| 5,338,625 | A | 8/1994 | Bates et al. |
| 5,347,186 | A | 9/1994 | Konotchick |
| 5,497,772 | A | 3/1996 | Schulman et al. |
| 5,522,394 | A | 6/1996 | Zurbrügg |
| 5,551,953 | A | 9/1996 | Lattin et al. |
| 5,589,932 | A | 12/1996 | Garcia-Rubio et al. |
| 5,705,293 | A | 1/1998 | Hobson |
| 5,752,512 | A | 5/1998 | Gozani |
| 5,815,954 | A | 10/1998 | Huang |
| 5,873,835 | A | 2/1999 | Hastings et al. |
| 5,876,445 | A | 3/1999 | Andersen et al. |
| 5,890,128 | A | 3/1999 | Diaz et al. |
| 6,001,067 | A | 12/1999 | Shults et al. |
| 6,023,932 | A | 2/2000 | Johnston |
| 6,075,199 | A | 6/2000 | Wong |
| 6,111,520 | A | 8/2000 | Allen et al. |
| 6,129,685 | A | 10/2000 | Howard, III |
| 6,151,517 | A | 11/2000 | Honigs et al. |
| 6,170,485 | B1 | 1/2001 | Orrico |
| 6,221,275 | B1 | 4/2001 | Choi et al. |
| 6,278,379 | B1 | 8/2001 | Allen et al. |
| 6,304,766 | B1 | 10/2001 | Colvin, Jr. |
| 6,409,674 | B1 | 6/2002 | Brockway et al. |
| 6,475,639 | B2 | 11/2002 | Shahinpoor et al. |
| 6,517,482 | B1 | 2/2003 | Elden et al. |
| 6,623,698 | B2 | 9/2003 | Kuo |
| 6,645,229 | B2 * | 11/2003 | Matsumura et al. ............ 607/1 |
| 6,673,596 | B1 | 1/2004 | Sayler et al. |
| 6,675,030 | B2 | 1/2004 | Ciurczak et al. |
| 6,675,041 | B2 | 1/2004 | Dickinson |
| 6,694,185 | B2 | 2/2004 | Orton |
| 6,754,472 | B1 | 6/2004 | Williams et al. |
| 6,802,811 | B1 | 10/2004 | Slepian |
| 6,836,678 | B2 | 12/2004 | Tu |
| 6,855,115 | B2 | 2/2005 | Fonseca et al. |
| 6,954,662 | B2 | 10/2005 | Freger et al. |
| 7,027,134 | B1 | 4/2006 | Garcia-Rubio et al. |
| 7,097,662 | B2 | 8/2006 | Evans, III et al. |
| 7,105,175 | B2 | 9/2006 | Schwarz |
| 7,125,382 | B2 | 10/2006 | Zhou et al. |
| 7,184,810 | B2 | 2/2007 | Caduff et al. |
| 7,212,110 | B1 | 5/2007 | Martin et al. |
| 7,299,080 | B2 | 11/2007 | Acosta et al. |
| 7,303,875 | B1 | 12/2007 | Bock et al. |
| 7,314,453 | B2 | 1/2008 | Kuo |
| 7,334,472 | B2 | 2/2008 | Seo et al. |
| 7,459,713 | B2 | 12/2008 | Coates |
| 7,548,779 | B2 | 6/2009 | Konchitsky |
| 7,577,470 | B2 | 8/2009 | Shah et al. |
| 2002/0045924 | A1 * | 4/2002 | Fox ............................... 607/96 |
| 2002/0127143 | A1 | 9/2002 | Kuo |
| 2003/0023189 | A1 | 1/2003 | Kuo |
| 2003/0143580 | A1 | 7/2003 | Straus |
| 2003/0152823 | A1 | 8/2003 | Heller |
| 2003/0225442 | A1 | 12/2003 | Saadat |
| 2004/0078219 | A1 | 4/2004 | Kaylor et al. |
| 2004/0100376 | A1 | 5/2004 | Lye et al. |
| 2005/0143787 | A1 | 6/2005 | Boveja et al. |
| 2005/0228259 | A1 | 10/2005 | Glukhovsky et al. |
| 2005/0277839 | A1 | 12/2005 | Alderman et al. |
| 2006/0146317 | A1 | 7/2006 | Aklian |
| 2006/0161230 | A1 * | 7/2006 | Craven ...................... 607/104 |
| 2006/0173508 | A1 | 8/2006 | Stone et al. |
| 2006/0234369 | A1 | 10/2006 | Sih |
| 2007/0060971 | A1 | 3/2007 | Glasberg et al. |
| 2007/0225781 | A1 | 9/2007 | Saadat et al. |
| 2008/0033518 | A1 * | 2/2008 | Rousso et al. ............. 607/112 |
| 2008/0046013 | A1 | 2/2008 | Lozano |
| 2008/0077211 | A1 | 3/2008 | Levinson et al. |
| 2008/0265146 | A1 | 10/2008 | Coates |
| 2009/0012574 | A1 | 1/2009 | Balczewski et al. |
| 2009/0015022 | A1 | 1/2009 | Rome et al. |
| 2009/0018624 | A1 | 1/2009 | Levinson et al. |
| 2009/0056328 | A1 | 3/2009 | Kao |
| 2009/0081271 | A1 | 3/2009 | Clarke et al. |
| 2009/0118780 | A1 | 5/2009 | DiLorenzo |
| 2009/0139248 | A1 | 6/2009 | Crumlin et al. |
| 2009/0149917 | A1 | 6/2009 | Whitehurst et al. |
| 2009/0149947 | A1 | 6/2009 | Frohwitter |
| 2009/0157151 | A1 | 6/2009 | Cauller et al. |
| 2009/0198293 | A1 | 8/2009 | Cauller et al. |
| 2009/0240113 | A1 | 9/2009 | Heckerman |
| 2009/0308082 | A1 | 12/2009 | Monk |
| 2009/0312676 | A1 | 12/2009 | Rousso et al. |
| 2009/0319026 | A1 | 12/2009 | Meyer |
| 2010/0049004 | A1 | 2/2010 | Edman et al. |
| 2010/0049021 | A1 | 2/2010 | Jina et al. |
| 2010/0076524 | A1 | 3/2010 | Forsberg et al. |
| 2010/0081910 | A1 | 4/2010 | Brister et al. |
| 2010/0111830 | A1 | 5/2010 | Boyden et al. |
| 2010/0111842 | A1 | 5/2010 | Boyden et al. |
| 2010/0111849 | A1 | 5/2010 | Boyden et al. |
| 2010/0111855 | A1 | 5/2010 | Boyden et al. |
| 2010/0112067 | A1 | 5/2010 | Boyden et al. |
| 2010/0113614 | A1 | 5/2010 | Boyden et al. |
| 2010/0125417 | A1 | 5/2010 | Hyde et al. |
| 2010/0125418 | A1 | 5/2010 | Hyde et al. |
| 2010/0125419 | A1 | 5/2010 | Hyde et al. |
| 2010/0125420 | A1 | 5/2010 | Hyde et al. |
| 2010/0152824 | A1 | 6/2010 | Allison |
| 2010/0185174 | A1 | 7/2010 | Boyden et al. |
| 2010/0312295 | A1 * | 12/2010 | Vase et al. ..................... 607/2 |
| 2011/0239682 | A1 * | 10/2011 | Raines et al. ............. 62/259.3 |
| 2011/0270360 | A1 * | 11/2011 | Harris et al. ................ 607/62 |

OTHER PUBLICATIONS

European Patent Office, Extended European Search Report, Pursuant to Rule 62 EPC; App. No. EP 12781678.3; Sep. 26, 2014 (received by our Agent on Oct. 2, 2014); pp. 1-6.

Alberti et al.; "Harmonizing the Metabolic Syndrome—A Joint Interim Statement of the International Diabetes Federation Task Force on Epidemiology and Prevention; National Heart, Lung, and Blood Institute; American Heart Association; World Heart Federation; International Atherosclerosis Society; and International Association for the Study of Obesity"; Circulation; 2009; pp. 1640-1645; vol. 120; American Heart Association, Inc.

Almind et al.; "Ectopic brown adipose tissue in muscle provides a mechanism for differences in risk of metabolic syndrome in mice"; PNAS; Feb. 13, 2007; pp. 2366-2371; vol. 104, No. 7; The National Academy of Sciences of the USA.

Au-Yong et al.; "Brown Adipose Tissue and Seasonal Variation in Humans"; Diabetes; Nov. 2009; pp. 2583-2587; vol. 58.

(56) References Cited

OTHER PUBLICATIONS

Bartness et al.; "Sympathetic and sensory innervation of brown adipose tissue"; International Journal of Obesity; 2010; pp. S36-S42; vol. 34; Macmillan Publishers Limited.
Bartelt et al.; "Brown adipose tissue activity controls triglyceride clearance"; Nature Medicine; Jan. 23, 2011; pp. 1-7; Nature America, Inc.
Böttner et al.; "New Thermoelectric Components Using Microsystem Technologies"; Journal of Microelectromechanical Systems; Jun. 2004; pp. 414-420; vol. 13, No. 3; IEEE.
Boulant et al.; "Temperature Receptors in the Central Nervous System"; Annu. Rev. Physiol.; 1986; pp. 639-654; vol. 48; Annual Reviews, Inc.
Budgett et al.; "Novel technology for the provision of power to implantable physiological devices"; J Appl Physiol; 2007; pp. 1658-1663; vol. 102; American Physiological Society.
Cannon et al.; "Brown Adipose Tissue: Function and Physiological Significance"; Physiol Rev; Jan. 2004; pp. 277-359; vol. 84; American Physiological Society.
Cannon et al.; "Thermogenesis challenges the adipostat hypothesis for body-weight control"; Proceedings of the Nutrition Society; 2009; pp. 401-407; vol. 68.
Carbunaru et al.; "Rechargeable Battery-Powered bion® Microstimulators for Neuromodulation"; Proceedings of the 26th Annual International Conference of the IEEE EMBS; Sep. 1-5, 2004; pp. 4193-4196; IEEE.
Celi, Francesco S.; "Brown Adipose Tissue—When It Pays to Be Inefficient"; N Engl J Med; Apr. 9, 2009; pp. 1553-1556; vol. 360, No. 15; Massachusetts Medical Society.
Cerri et al.; "Activation of Lateral Hypothalamic Neurons Stimulates Brown Adipose Tissue Thermogenesis"; Neuroscience; 2005; pp. 627-638; vol. 135; Elsevier Ltd.
Chen et al.; "A Miniature Biofuel Cell"; J. Am. Chem. Soc.; Abstract; 2 pages; 2001; pp. 8630-8631; vol. 123, No. 35; American Chemical Society.
Choi et al.; "Distributions of Skin Thermoreceptors and Clothing Weights of Korean Urbanites and Farmers"; J Physiol Anthropol; 2001; pp. 375-377; vol. 20, No. 6.
Christensen et al.; "Reversal of Hypermetabolic Brown Adipose Tissue in F-18 FDG Pet Imaging"; Clinical Nuclear Medicine; Apr. 2006; pp. 193-196; vol. 31, No. 4.
Cotter et al.; "The distribution of cutaneous sudomotor and alliesthesial thermosensitivity in mildly heat-stressed humans: an open-loop approach"; J Physiol; 2005; pp. 335-345; vol. 565, No. 1; The Physiological Society.
Craig et al.; "Quantitative Response Characteristics of Thermoreceptive and Nociceptive Lamina 1 Spinothalamic Neurons in the Cat"; J Neurophysiol; Sep. 2001; pp. 1459-1480; vol. 86; The American Physiological Society.
Cypess et al.; "Identification and Importance of Brown Adipose Tissue in Adult Humans"; The New England Journal of Medicine; Apr. 9, 2009; pp. 1509-1517; vol. 360; Massachusetts Medical Society.
Duke et al.; "Combined optical and electrical stimulation of neural tissue in vivo"; Journal of Biomedical Optics; Nov./Dec. 2009; pp. 060501-1 to 060501-3; vol. 14, No. 6.
Durick et al.; "Cellular biosensors for drug discovery"; Biosensors & Bioelectronics; 2001; pp. 587-592; vol. 16; Elsevier Science B.V.
Fajardo et al.; "TRPA1 Channels Mediate Cold Temperature Sensing in Mammalian Vagal Sensory Neurons: Pharmacological and Genetic Evidence"; The Journal of Neuroscience.; Jul. 30, 2008; pp. 7863-7875; vol. 28, No. 31; Society for Neuroscience.
Fan et al.; "Sensitive optical biosensors for unlabeled targets: a review"; Analytica Chimica Acta; 2008; pp. 8-26; vol. 620; Elsevier B.V.
Flechtner-Mors et al.; "In Vivo $\alpha_1$-Adrenergic Lipolytic Activity in Subcutaneous Adipose Tissue of Obese Subjects"; The Journal of Pharmacology and Experimental Therapeutics; 2002; pp. 229-233; vol. 301, No. 1; The American Society for Pharmacology and Experimental Therapeutics.

Froy, Oren; "Metabolism and Circadian Rhythms-Implications for Obesity"; Endocrine Reviews; Feb. 2010; pp. 1-24; vol. 31, No. 1; The Endocrine Society.
Fujioka et al.; "An implantable, focal brain cooling device suppresses nociceptive pain in rats"; Neuroscience Research; 2010; pp. 402-405; vol. 66; Elsevier Ireland Ltd. and the Japan Neuroscience Society.
Gabaldón et al.; "Norepinephrine release in brown adipose tissue remains robust in cold-exposed senescent Fischer 344 rats"; Am J Physiol Regul Integr Comp Physiol; 2003; pp. R91-R98; vol. 285; American Physiological Society.
Golden et al.; "Prevalence and Incidence of Endocrine and Metabolic Disorders in the United States: A Comprehensive Review"; J Clin Endocrinol Metab; Jun. 2009; pp. 1853-1878; vol. 94, No. 6; The Endocrine Society.
Grayson et al.; "A BioMEMS Review: MEMS Technology for Physiologically Integrated Devices"; Proceedings of the IEEE; Jan. 2004; pp. 6-21; vol. 92, No. 1; IEEE.
Gschneider, Jr. et al.; "Thirty years of near room temperature magnetic cooling: Where we are today and future prospects"; International Journal of Refrigeration; Abstract; one page; Sep. 2008; pp. 945-961; vol. 31, Issue 6.
Hagleitner et al.; "Smart single-chip gas sensor microsystem"; Nature; Nov. 15, 2001; pp. 293-296; vol. 414; Macmillan Magazines Ltd.
Hermanides et al.; "Sense and nonsense in sensors"; Diabetologia; 2010; pp. 593-596; vol. 53; Springer.
Hönes et al.; "The Technology Behind Glucose Meters: Test Strips"; Diabetes Technology & Therapeutics; 2008; pp. S-10 to S-26; vol. 10, Supplement 1; Mary Ann Liebert, Inc.
Itoh et al.; "Fluorometric Determination of Glucose Utilization in Neurons in Vitro and in Vivo"; Journal of Cerebral Blood Flow & Metabolism; 2004; pp. 993-1003; vol. 24, No. 9; The International Society for Cerebral Blood Flow and Metabolism.
Jamal et al.; "An improved automated method for the measurement of thermal thresholds. 1. normal subjects"; Journal of Neurology, Neurosurgery, and Psychiatry; 1985; pp. 354-360; vol. 48.
Jensen et al.; "In vivo and in vitro microdialysis sampling of free fatty acids"; Journal of Pharmaceutical and Biomedical Analysis; 2007; pp. 1751-1756; vol. 43; Elsevier B.V.
Jiang et al.; "Cold- and menthol-sensitive C afferents of cat urinary bladder"; Journal of Physiology: 2002; pp. 211-220; vol. 543, No. 1; The Physiological Society.
Johnson et al.; "Could increased time spent in a thermal comfort zone contribute to population increases in obesity?"; Obesity Reviews; 2011: pp. 1-9; International Association for the Study of Obesity.
Jokar et al.; "Single-Phase Flow in Meso-Channel Compact Heat Exchangers for Air Conditioning Applications"; Heat Transfer Engineering; 2010; pp. 3-16; vol. 31, No. 1; Taylor and Francis Group, LLC.
Judd et al.; "Measurement of plasma glycerol specific activity by high performance liquid chromatography to determine glycerol flux"; Journal of Lipid Research; 1998; pp. 1106-1110; vol. 39.
Kajimura et al.; "Initiation of myoblast to brown fat switch by a PRDMI6-C/EBP-β transcriptional complex"; Nature; Jul. 29, 2009; pp. 1-6; Macmillan Publishers Limited.
Kajimura et al.; "Transcriptional Control of Brown Fat Development"; Cell Metabolism; Apr. 7, 2010; pp. 257-262; vol. 11; Elsevier Inc.
Klingenspor, Martin; "Cold-induced recruitment of brown adipose tissue thermogenesis"; Exp Physiol; 2003; pp. 141-148; vol. 88, No. 1.
Kochemasov et al.; "Implantable brain microcooler for the closed-loop system of epileptic seizure prevention"; IFMBE Proceedings 16; 2007; pp. 911-914; Springer-Verlag Berlin Heidelberg 2007.
Lakowicz, Joseph R.; "Advances in Fluorescence Sensing Technology II"; Abstract; one page; May 8, 1995; pp. 462-470; SPIE.
Lavrik et al.; "Cantilever transducers as a platform for chemical and biological sensors"; Review of Scientific Instruments; Jul. 2004; pp. 2229-2253; vol. 75, No. 7; American Institute of Physics.
Lee et al.; "A critical appraisal of the prevalence and metabolic significance of brown adipose tissue in adult humans"; Am J Physiol Endocrinol Metab; 2010; pp. E601-E606; vol. 299; American Physiological Society.

(56) References Cited

OTHER PUBLICATIONS

Lee et al.; "Application of Metallic Nanoparticle Suspensions in Advanced Cooling Systems"; Nov. 17-23, 1996; International Mechanical Engineering Conference; 12 pgs.

Lee et al.; "Investigation of heat transfer in rectangular microchannels"; International Journal of Heat and Mass Transfer; 2005; pp. 1688-1704; vol. 48; Elsevier Ltd.

Li et al.; "Development of Novel Glucose Sensing Fluids with Potential Application to Microelectromechanical Systems-Based Continuous Glucose Monitoring"; Journal of Diabetes Science and Technology; Nov. 2008; pp. 1066-1074; vol. 2, No. 6; Diabetes Technology Society.

Lyubynskaya et al.; "Implantable brain microcooler for the closed-loop system of epileptic seizure prevention"; 11th Mediterranean Conference on Medical and Biomedical Engineering and Computing 2007; IFMBE Proceedings 2007; Abstract; one page; 2007; pp. 911-914; vol. 16, Part 23.

Lyznicki et al.; "Obesity: Assessment and Management in Primary Care"; American Family Physician; Jun. 1, 2001; pp. 2185-2196; vol. 63, No. 11.

Ma et al.; "Ablations of Ghrelin and Ghrelin Receptor Exhibit Differential Metabolic Phenotypes and Thermogenic Capacity during Aging"; $PL_oS$ One; Jan. 2011; pp. 1-10; vol. 6, No. 1.

Mattson, Mark P.; "Does Brown Fat Protect Against Diseases of Aging?"; Ageing Res Rev.; Jan. 2010; pp. 1-17; vol. 9, No. 1.

Mok et al.; "Recent Progress in Nucleic Acid Aptamer-Based Biosensors and Bioassays"; Sensors; 2008; pp. 7050-7084; vol. 8.

Moore, Bert; "The Potential Use of Radio Frequency Identification Devices for Active Monitoring of Blood Glucose Levels"; Journal of Diabetes Science and Technology; Jan. 2009; pp. 180-183; vol. 3, No. 1; Diabetes Technology Society.

Morrison et al.; "Central control of thermogenesis in mammals"; Exp Physiol; 2008; pp. 773-797; vol. 93, No. 7; The Physiological Society.

Morrison, Shaun F.; "Central Pathways Controlling Brown Adipose Tissue Thermogenesis"; News Physiol Sci; Apr. 2004; pp. 67-74; vol. 19; Int. Union Physiol. Sci./Am. Physiol. Soc.

Morrison et al.; "Central neural pathways for thermoregulation"; Frontiers in Bioscience; Jan. 1, 2011; pp. 74-104; vol. 16.

Morrison et al.; "Clinical Applications of Micro- and Nanoscale Biosensors": Biomedical Nanostructures; 2008; Chapter 17; pp. 433-455; John Wiley & Sons, Inc.

Nagasaka, Tetsuo; "Effects of daily infusions of noradrenaline on metabolism and skin temperature in rabbits"; Journal of Applied Physiology; Feb. 1972; pp. 199-202; vol. 32, No. 2.

Nedergaard et al.; "The Changed Metabolic World with Human Brown Adipose Tissue: Therapeutic Visions"; Cell Metabolism; Apr. 7, 2010; pp. 268-272; vol. 11; Elsevier Inc.

Nedergaard et al.; "Unexpected evidence for active brown adipose tissue in adult humans"; Am J Physiol Endocrinol Metab; May 2007; pp. E444-E452; vol. 293; American Physiological Society.

Nielsen et al.; "Clinical Evaluation of a Transcutaneous Interrogated Fluorescence Lifetime-Based Microsensor for Continuous Glucose Reading"; Journal of Diabetes Science and Technology; Jan. 2009; pp. 98-109; vol. 3, No. 1; Diabetes Technology Society.

Nyman et al.; "Soft Tissue-anchored Transcutaneous Port Attached to an Intestinal Tube for Long-term Gastroduodenal Infusion of Levodopa/Carbidopa in Parkinson Disease"; Journal of Vascular and Interventional Radiology; Abstract; 2 pages; Apr. 2009; pp. 500-505; vol. 20, No. 4.

Oesterreicher et al.; "Magnetic cooling near Curie temperatures above 300 K"; J. Appl. Phys; Abstract; one page; 1984; pp. 4334-4338; vol. 55, No. 12.

Pakhomov et al.; "Effects of High Power Microwave Pulses on Synaptic Transmission and Long Term Potentiation in Hippocampus"; Bioelectromagnetics; 2003; pp. 174-181; vol. 24; Wiley-Liss, Inc.

Parysow et al.; "Low-Dose Oral Propranolol Could Reduce Brown Adipose Tissue F-18 FDG Uptake in Patients Undergoing PET Scans"; Clinical Nuclear Medicine; Abstract; one page; May 2007; pp. 351-357; vol. 32, No. 5; Lippincott Williams & Wilkins, Inc.

Passlick-Deetjen et al.; "Why thermosensing? A primer on thermoregulation"; Nephrol Dial Transplant; 2005; pp. 1784-1789; vol. 20.

Piccinni et al.; "Definitive palliation for neoplastic colonic obstruction using enteral stents: Personal case-series with literature review"; World J Gastroenterol; 2004; pp. 758-764; vol. 10, No. 5; The WJG Press.

Poirier et al.; "Obesity and Cardiovascular Disease: Pathophysiology, Evaluation, and Effect of Weight Loss"; Circulation; 2006; pp. 898-918; vol. 113; American Heart Association, Inc.

Qi et al.; "Piezoelectric Ribbons Printed onto Rubber for Flexible Energy Conversion"; Nano Lett.; 2010; pp. 524-528; vol. 10; American Chemical Society.

Rabi et al.; "Lipolysis in brown adipose tissue of cold- and heat-acclimated hamsters"; Journal of Applied Physiology; Abstract; one page; Dec. 1, 1977; pp. 1007-1111; vol. 43.

Raghavan et al.; "BIAcore: a microchip-based system for analyzing the formation of macromolecular complexes"; Structure; Apr. 15, 1995; pp. 331-333; vol. 3; Current Biology Ltd.

Rawson et al.; "Localization of Intra-Abdominal Thermoreceptors in the Ewe"; J. Physiol.; 1972; pp. 665-677; vol. 222.

Richard et al.; "Brown fat biology and thermogenesis"; Frontiers in Bioscience; Jan. 1, 2011; pp. 1233-1260; vol. 16.

Saely et al.; "Brown versus White Adipose Tissue: A Mini-Review"; Gerontology; Dec. 7, 2010; pp. 1-9; S. Karger AG, Basel.

Saito et al.; "High Incidence of Metabolically Active Brown Adipose Tissue in Healthy Adult Humans"; Diabetes; Jul. 2009; pp. 1526-1531; vol. 58; American Diabetes Association.

Schoenen et al.; "Hypothalamic stimulation in chronic cluster headache: a pilot study of efficacy and mode of action"; Brain; 2005; pp. 940-947; vol. 128.

Schmidt et al.; "Microbial biosensor for free fatty acids using an oxygen electrode based on thick film technology"; Biosensors and Bioelectronics; Abstract; one page; 1996; pp. 1139-1145; vol. 11, No. 11; Elsevier Science B.V.

Seale et al.; "Brown Fat in Humans: Turning up the Heat on Obesity"; Diabetes; Jul. 2009; pp. 1482-1484; vol. 58.

Sierra, C. V. Rizzo; "Noninvasive deep brain stimulation using focused energy sources"; Current Science; Jan. 10, 2010; pp. 27-29; vol. 98, No. 1.

Smiles et al.; "Sweating responses during changes of hypothalamic temperature in the rhesus monkey"; Journal of Applied Physiology; May 1976; pp. 653-657; vol. 40, No. 5.

Snow et al.; "Chemical Detection with a Single-Walled Carbon Nanotube Capacitor"; Science; Mar. 25, 2005; pp. 1942-1945; vol. 307.

Söderlund et al.; "Reduction of FDG uptake in brown adipose tissue in clinical patients by a single dose of propranolol"; European Journal of Nuclear Medicine and Molecular Imaging; Abstract; one page; published online Jan. 16, 2007; pp. 1018-1022.

Solomon et al.; "Menstrual cycle and basal metabolic rate in women"; The American Journal of Clinical Nutrition; Oct. 1982; pp. 611-616; vol. 36; American Society for Clinical Nutrition.

"Standards of Medical Care in Diabetes-2010"; Diabetes Care; Jan. 2010; pp. S11-S61; vol. 33, Supplement 1; American Diabetes Association.

Tamura et al.; "One-chip sensing device (biomedical photonic LSI) enabled to assess hippocampal steep and gradual up-regulated proteolytic activities"; Journal of Neuroscience Methods; 2008; pp. 114-120; vol. 173; Elsevier B.V.

Teruel et al.; "Rosiglitazone and Retinoic Acid Induce Uncoupling Protein-1 (UCP-1) in a p38 Mitogen-activated Protein Kinase-dependent Manner in Fetal Primary Brown Adipocytes"; The Journal of Biological Chemistry; Jan. 3, 2003; pp. 263-269; vol. 278, No. 1; The American Society for Biochemistry and Molecular Biology, Inc.

The Biomedical Engineering Handbook, Second Edition, vol. 1; J.D. Bronzino, Ed., Copyright 2000, CRC Press LLC; one page.

Thornhill et al.; "Brown Adipose Tissue Thermogenic Responses of Rats Induced by Central Stimulation: Effect of Age and Cold Acclimation"; Journal of Physiology; 1990; pp. 317-333; vol. 426.

Timmons, James A.; "The Importance of Brown Adipose Tissue"; The New England Journal of Medicine; Jul. 23, 2009; pp. 415-421; vol. 361, No. 4; Massachusetts Medical Society.

(56) References Cited

OTHER PUBLICATIONS

Tseng et al.; "New role of bone morphogenetic protein 7 in brown adipogenesis and energy expenditure"; Nature; Aug. 21, 2008; pp. 1000-1004; vol. 454; Macmillan Publishers Limited.

Tyler, William J.; "Noninvasive Neuromodulation with Ultrasound? A Continuum Mechanics Hypothesis"; Neuroscientist OnlineFirst; published on Jan. 25, 2010; pp. 1-12.

Van Marken Lichtenbelt et al.; "Cold-Activated Brown Adipose Tissue in Healthy Men"; The New England Journal of Medicine; Apr. 9, 2009; pp. 1500-1508; vol. 360, No. 15; Massachusetts Medical Society.

Vashist, Sandeep Kumar; "A Review of Microcantilevers for Sensing Applications"; Journal of Nanotechnology Online; Jun. 2007; pp. 1-15; vol. 3.

Villanova et al.; "Perception and gut reflexes induced by stimulation of gastrointestinal thermoreceptors in humans"; Journal of Physiology; 1997; pp. 215-222; vol. 502, No. 1.

Virtanen et al.; "Functional Brown Adipose Tissue in Healthy Adults"; The New England Journal of Medicine; Apr. 9, 2009; pp. 1518-1525; vol. 360, No. 15; Massachusetts Medical Society.

Wacharasindhu et al.; "Radioisotope microbattery based on liquid semiconductor"; Applied Physics Letters; 2009; pp. 014103-1-014103-3; vol. 95; American Institute of Physics.

Wadum et al.; "Fluorescently labelled bovine acyl-CoA-binding protein acting as an acyl-CoA sensor: interaction with CoA and acyl-CoA esters and its use in measuring free acyl-CoA esters and non-esterified fatty acids"; Biochem J.; 2002; pp. 165-172; vol. 365; Biochemical Society.

Wassermann Em; "Risk and safety of repetitive transcranial magnetic stimulation: report and suggested guidelines from the International Workshop on the Safety of Repetitive Transcranial Magnetic Stimulation", Electroencephalogr Clin Neurophysiol; Jun. 5-7, 1996; Abstract; one page; Jan. 1998; pp. 1-16; vol. 108, No. 1.

Wells et al.; "Biophysical Mechanisms of Transient Optical Stimulation of Peripheral Nerve"; Biophysical Journal; Oct. 2007; pp. 2567-2580; vol. 93, No. 7; Biophysical Society.

Wells et al.; "Stimulating nerves with laser precision"; The International Society for Optical Engineering; 2006; pp. 1-2; 10.1117/2.1200605.0233; SPIE.

Yang et al.; "Converting Biomechanical Energy into Electricity by a Muscle-Movement-Driven Nanogenerator"; Nano Lett.; 2009; pp. 1201-1205; vol. 9, No. 3; American Chemical Society.

Yang et al.; "On-Chip Electrochemical Impedance Spectroscopy for Biosensor Arrays"; Oct. 22-25, 2006; pp. 93-96; IEEE Sensors, EXCO, Daegu, Korea; IEEE.

Yang et al.; "Power generation with laterally packaged piezoelectric fine wires"; Nature Nanotechnology; Abstract; two pages; 2009; pp. 34-39, vol. 4.

Yoneshiro et al.; "Brown Adipose Tissue, Whole-Body Energy Expenditure, and Thermogenesis in Healthy Adult Men"; Obesity; Jan. 2011; pp. 13-16; vol. 19, No. 1; Nature Publishing Group.

Yu et al.; "Cold elicits the simultaneous induction of fatty acid synthesis and β-oxidation in murine brown adipose tissue: prediction from differential gene expression and confirmation in vivo"; The FASEB Journal; Feb. 2002; pp. 155-168; vol. 16; FASEB.

Yusa et al.; "Controlled multiple quantum coherences of nuclear spins in a nanometre-scale device"; Nature; Apr. 21, 2005; pp. 1001-1005; vol. 434; Nature Publishing Group.

Zhang et al,; "Thermosensitive transient receptor potential channels in vagal afferent neurons of the mouse"; Am J Physiol Gastrointest Liver Physiol; 2004; G983-G991; vol. 286; American Physiological Society.

Zukotynski et al.; "Constant ambient temperature of 24° C significantly reduces FDG uptake by brown adipose tissue in children scanned during the winter"; Eur J Nucl Med Mol Imaging; 2009; pp. 602-606; vol. 36; Springer-Verlag.

\* cited by examiner

METHOD, DEVICE AND SYSTEM FOR MODULATING AN ACTIVITY OF BROWN ADIPOSE TISSUE IN A VERTEBRATE SUBJECT

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications is incorporated herein by reference to the extent such subject matter is not inconsistent herewith.

RELATED APPLICATIONS

For purposes of the USPTO extra-statutory requirements, the present application constitutes a continuation-in-part of U.S. patent application Ser. No. 13/068,421, entitled METHOD, DEVICE AND SYSTEM FOR MODULATING AN ACTIVITY OF BROWN ADIPOSE TISSUE IN A VERTEBRATE SUBJECT, naming Edward S. Boyden, Roderick A. Hyde, Muriel Y. Ishikawa, Edward K. Y. Jung, Eric C. Leuthardt, Stephen L. Malaska, Elizabeth A. Sweeney and Lowell L. Wood, Jr. as inventors, filed 9 May 2011, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 13/068,420, entitled METHOD, DEVICE AND SYSTEM FOR MODULATING AN ACTIVITY OF BROWN ADIPOSE TISSUE IN A VERTEBRATE SUBJECT, naming Edward S. Boyden, Roderick A. Hyde, Muriel Y. Ishikawa, Edward K. Y. Jung, Eric C. Leuthardt, Stephen L. Malaska, Elizabeth A. Sweeney and Lowell L. Wood, Jr. as inventors, filed 9 May 2011, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation, continuation-in-part, or divisional of a parent application. Stephen G. Kunin, *Benefit of Prior-Filed Application*, USPTO Official Gazette Mar. 18, 2003. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant has provided designation(s) of a relationship between the present application and its parent application(s) as set forth above, but expressly points out that such designation(s) are not to be construed in any way as any type of commentary and/or admission as to whether or not the present application contains any new matter in addition to the matter of its parent application(s).

SUMMARY

A device is disclosed herein that can be used in a method for modulating activity of brown adipose tissue in a vertebrate subject. The device can be used in a method for inducing weight loss in a vertebrate subject or in a method for treating a disorder, e.g., a metabolic disorder, diabetes, obesity, metabolic syndrome, dyslipidemia, or hypercholesterolemia, in a vertebrate subject. The device includes one or more cooling elements configured to be applied to one or more tissues of a vertebrate subject to modulate at least one activity of brown adipose tissue of the vertebrate subject, wherein at least a portion of the one or more cooling elements is configured to be implantable, and a programmable controller configured to provide instructions to the one or more cooling elements in response to information regarding one or more physiological conditions of the vertebrate subject. The device can further include one or more sensors operably connected to the programmable controller, wherein the programmable controller is configured to provide instructions to the one or more cooling elements in response to information from the one or more sensors regarding one or more physiological conditions of the vertebrate subject.

A device is disclosed herein that includes one or more cooling elements configured to be applied to one or more tissues of a vertebrate subject to modulate at least one activity of brown adipose tissue of the vertebrate subject, wherein at least a portion of the one or more cooling elements is configured to be implantable, and a programmable controller configured to provide instructions to the one or more cooling elements in response to information regarding one or more physiological conditions of the vertebrate subject. The device can further include one or more sensors operably connected to the programmable controller, wherein the programmable controller is configured to provide instructions to the one or more cooling elements in response to information from the one or more sensors regarding the one or more physiological conditions of the vertebrate subject. The programmable controller can be configured to receive information regarding the one or more physiological conditions from the one or more sensors. The device can further include a digital processing unit operably connected to the programmable controller, the digital processing unit configured to receive information from at least one of a sensor, a timekeeping device, a user interface, and an outside operating source, and configured to process the information into at least one resulting instruction and configured to provide the at least one resulting instruction to the programmable controller.

The information regarding the one or more physiological conditions can include information regarding one or more analytes in the vertebrate subject. The information regarding the one or more physiological conditions can include a plasma level of one or more analytes in the vertebrate subject. The information regarding the one or more physiological conditions can include a level of one or more of a metabolic analyte, a sugar, a lipoprotein, or a fatty acid in the vertebrate subject. The information regarding the one or more physiological conditions can include information regarding the at least one activity of the brown adipose tissue.

The device can further include an outside operating source operably connected to the programmable controller, wherein the programmable controller in communication with the outside operating source is configured to provide instructions to the one or more cooling elements in response to information from the outside operating source regarding the one or more physiological conditions of the vertebrate subject. The outside operating source can include a computing device or a human operator. The programmable controller can be configured to accept or send information from or to one or more of a timekeeping device or a user interface. The timekeeping device can be internal to the programmable controller. The programmable controller can be configured to accept user input. The user input can include information relating to one or more of calories ingested by the vertebrate subject, or food ingested by the vertebrate subject. The user input can include, but is not limited to, time input, time of day, period of time, start time, stop time, or length of time.

The device can further include at least one of circuitry and data storage. The device can include programming. The programmable controller can include programming designed to induce weight loss. The programmable controller can include programming designed to treat a disorder. The programmable controller can be configured to be associated with clothing of the vertebrate subject. The programmable controller can be configured to be implanted in the vertebrate subject. The programmable controller can be configured to be located within at least one lumen of the vertebrate subject during use.

The one or more cooling elements can be configured to be located within at least one lumen of the vertebrate subject during use. The one or more cooling elements can be configured to be located within at least one circulatory vessel of the vertebrate subject during use. The one or more cooling elements can be configured to be located within a colon or a large intestine of the vertebrate subject during use. The one or more cooling elements can include one or more electrical cooling elements. The one or more cooling elements can include one or more Peltier cooling elements. The one or more cooling elements can include one or more heat pumps. The one or more heat pumps can transfer heat to one or more tissues including blood or skin of the vertebrate subject. The one or more cooling elements can include one or more implantable deep tissue heat-extracting components in combination with one or more surface tissue heat-releasing components. The one or more cooling elements can include one or more chemical cooling elements. The one or more cooling elements can include, but is not limited to, one or more of nanoparticles, microparticles, paramagnetic particles, magnetic particles, or chemical core particles. The one or more cooling elements can be configured to be injectable. The one or more chemical core particles can include endothermal chemical reactants. The one or more implantable cooling elements can include one or more endothermic biodegradable particles. The one or more endothermic biodegradable particles can include one or more solid ice ($H_2O$) particles.

In the device, modulating the at least one activity of the brown adipose tissue can include increasing metabolic activity of brown adipose tissue or increasing proliferation of brown adipose tissue in the vertebrate subject. In the device, modulating the at least one activity of the brown adipose tissue can include inducing non-shivering thermogenesis in the brown adipose tissue. The one or more tissues can include thermoresponsive tissue of the vertebrate subject. The one or more tissues can include nervous tissue of the vertebrate subject. The one or more tissues can include cutaneous tissue of the vertebrate subject. The one or more tissues can include brown adipose tissue. The one or more tissues can include tissue in a core of a body of the vertebrate subject. The one or more tissues can include one or more blood vessels or lymph vessels. The implantable portion of the device can be configured to be injectable.

The one or more implantable cooling elements can be configured to attain a tissue temperature from approximately 4° C. to approximately 36° C. The one or more implantable cooling elements can be configured to attain a tissue temperature from approximately 12° C. to approximately 20° C. The one or more implantable cooling elements can be configured to attain a tissue temperature from approximately 24° C. to approximately 32° C. The one or more implantable cooling elements can be configured to attain a tissue temperature approximately 16° C. or lower. The programmable controller can be configured to be incorporated with one or more of clothing, bedding, furniture, or upholstery. The device can further include a power source configured to power the device. The power source can include, but is not limited to, stored power, a battery, a fuel cell, or beamed power.

The device can further include a neurostimulator configured to be applied to the one or more tissues. The device can further include a neurostimulator configured to be applied to one or more second tissues of the vertebrate subject other than the one or more tissues. The one or more second tissues can include nerve tissue. The neurostimulator can include, but is not limited to, at least one of electric neurostimulator, magnetic neurostimulator, ultrasonic neurostimulator, or microwave neurostimulator. The device can further include an applicator configured to deliver a therapeutic medicament.

A method for modulating an activity of a brown adipose tissue in a vertebrate subject is disclosed herein that includes applying cooling to one or more tissues of the vertebrate subject with one or more cooling elements, wherein the one or more cooling elements are configured to lower the temperature of the one or more tissues and thereby modulate at least one activity of the brown adipose tissue of the vertebrate subject, wherein at least a portion of the one or more cooling elements is configured to be implantable, and controlling the one or more cooling elements with a programmable controller configured to provide instructions to the one or more cooling elements in response to information regarding one or more physiological conditions of the vertebrate subject. The method can further include sensing with one or more sensors the information regarding the one or more physiological conditions and communicating the information from the one or more sensors to the programmable controller. The method can further include sensing with one or more sensors the information regarding the one or more physiological conditions and communicating the information from the one or more sensors to a digital processing unit, processing the information with the digital processing unit into at least one resulting instruction, and providing by the digital processing unit the at least one resulting instruction to the programmable controller.

The method can further include receiving the information regarding the one or more physiological conditions from an outside operating source to a receiver including at least one of the programmable controller or a digital processing unit. The outside operating source can include a computing device or a human operator. In the method, processing the information with the digital processing unit can include comparing the information regarding the one or more physiological conditions to information of a standard value or preprogrammed value. The information regarding the one or more physiological conditions can include a plasma level of one or more metabolic analytes in the vertebrate subject. The information regarding the one or more physiological conditions can include a sugar level or a fatty acid level in the vertebrate subject.

In the method, modulating the at least one activity of the brown adipose tissue includes increasing metabolic activity or increasing proliferation of brown adipose tissue in the vertebrate subject. In the method, modulating the at least one activity of the brown adipose tissue can include inducing non-shivering thermogenesis in the brown adipose tissue. The method can further include implanting the programmable controller in the vertebrate subject. The method can further include implanting the programmable controller within a lumen of the vertebrate subject. The method can further include implanting at least a portion of one or more cooling elements within a lumen of the vertebrate subject. The method can further include implanting the at least a portion of one or more cooling elements within a circulatory vessel of the vertebrate subject. The method can further include implanting the at least a portion of one or more cooling elements within a colon or a large intestine of the vertebrate subject. The one or more tissues can include thermoresponsive tissue of the vertebrate subject. The one or more tissues can include nervous tissue of the vertebrate subject. The one or more tissues can include a cutaneous tissue of the vertebrate subject. The one or more tissues can include brown adipose tissue. The one or more tissues can include tissue in a core of the body of the vertebrate subject. The one or more tissues can include one or more blood vessels or lymph vessels.

The one or more cooling elements can be configured to cool by electrical cooling activity. The one or more cooling elements can be configured to cool by Peltier cooling activity. The one or more cooling elements can be configured to cool by heat pumps. The one or more heat pumps can be configured to transfer heat to one or more tissues including blood or skin of the vertebrate subject. The one or more cooling elements are configured to cool by one or more implantable deep tissue heat-extracting components in combination with one or more surface tissue heat-releasing components. The one or more cooling elements can be configured to cool by chemical cooling activity. The one or more cooling elements can include, but is not limited to, one or more of nanoparticles, microparticles, paramagnetic particles, magnetic particles, or chemical core particles. The method can further include injecting the implantable portion of the one or more cooling elements. The one or more chemical core particles can include endothermal chemical reactants. The one or more implantable cooling elements can include one or more endothermic biodegradable particles. The one or more endothermic biodegradable particles can include one or more solid ice ($H_2O$) particles.

The method can further include cooling the tissue with the one or more implantable cooling elements to attain a tissue temperature from approximately 4° C. to approximately 36° C. The method can further include cooling the tissue with the one or more implantable cooling elements to attain a tissue temperature from approximately 12° C. to approximately 20° C. The method can further include cooling the tissue with the one or more implantable cooling elements to attain a tissue temperature from approximately 24° C. to approximately 32° C. The method can further include cooling the tissue with the one or more implantable cooling elements to attain a tissue temperature approximately 16° C. or lower. The programmable controller can be incorporated in clothing, bedding, furniture, or upholstery. The method can further include powering the device with a power source. The power source can include, but is not limited to, stored power, a battery, a fuel cell, or beamed power.

The vertebrate subject can be undergoing treatment for at least one of weight loss, diabetes, obesity, metabolic syndrome, dyslipidemia, or hypercholesterolemia. The method can further include providing one or more medicaments for treatment of weight loss, metabolic disorder, diabetes, obesity, metabolic syndrome, dyslipidemia, or hypercholesterolemia, configured to be applied to the one or more tissues in combination with the one or more cooling elements of the device. The one or more medicaments include one or more of β-adrenergic receptor agonist, NPY antagonist, leptin, UCP activating agent, thyroxine, serotonin reuptake inhibitor, MCH antagonist, GLP-1 agonist, 5-HT2C agonist, 5-HT2A agonist, galanin antagonist, CRF agonist, urocortin agonist, melanocortin agonist or enterostatin agonist.

The method can further include applying a neurostimulator to the one or more tissues. The method can further include applying a neurostimulator to one or more second tissues other than the one or more tissues. The one or more other tissues can include nerve tissue. In the method, applying the neurostimulator can include, but is not limited to, electric neurostimulator, magnetic neurostimulator, ultrasonic neurostimulator, or microwave neurostimulator.

A method for inducing weight loss in a vertebrate subject is disclosed herein that includes applying cooling to one or more tissues of the vertebrate subject with one or more cooling elements, wherein the one or more cooling elements are configured to lower the temperature of the one or more tissues and thereby modulate at least one activity of brown adipose tissue of the vertebrate subject, wherein at least a portion of the one or more cooling elements is configured to be implantable, and controlling the one or more cooling elements with a programmable controller configured to provide instructions to the one or more cooling elements in response to information regarding one or more physiological conditions of the vertebrate subject.

The method can further include sensing with one or more sensors the information regarding the one or more physiological conditions and communicating the information from the one or more sensors to the programmable controller. The method can further include sensing with one or more sensors the information regarding the one or more physiological conditions and communicating the information from the one or more sensors to a digital processing unit, processing the information with the digital processing unit into at least one resulting instruction, and providing by the digital processing unit the at least one resulting instruction to the programmable controller. The method can further include receiving the information regarding the one or more physiological conditions from an outside operating source to a receiver including at least one of the programmable controller or a digital processing unit.

The outside operating source can include a computing device or a human operator. In the method, processing the information with the digital processing unit can include comparing the information regarding the one or more physiological conditions to information of a standard value or preprogrammed value. The information regarding the one or more physiological conditions can include a plasma level of one or more metabolic analytes in the vertebrate subject. The information regarding the one or more physiological conditions can include sugar levels or fatty acid levels in the vertebrate subject.

In the method, modulating the at least one activity of the brown adipose tissue can include increasing metabolic activity or increasing proliferation of brown adipose tissue in the vertebrate subject. Modulating the at least one activity of the brown adipose tissue can include inducing non-shivering thermogenesis in the brown adipose tissue. The one or more tissues can include thermoresponsive tissue of the vertebrate subject. The method can further include powering the device with a power source. The method can further include providing one or more medicaments for treatment of weight loss, metabolic disorder, diabetes, obesity, metabolic syndrome, dyslipidemia, or hypercholesterolemia, configured to be applied to the one or more tissues in combination with the one or more cooling elements of the device. The method can further include applying a neurostimulator to the one or more tissues. The method can further include applying a neurostimulator to one or more second tissues other than the one or more tissues. The one or more other tissues can include nerve tissue. In the method, applying the neurostimulator includes electric neurostimulator, magnetic neurostimulator, ultrasonic neurostimulator, or microwave neurostimulator.

A method for treating a disorder in a vertebrate subject is disclosed herein that includes applying cooling to one or more tissues of the vertebrate subject with one or more cooling elements, wherein the one or more cooling elements are configured to lower the temperature of the one or more tissues and thereby modulate at least one activity of brown adipose tissue of the vertebrate subject, wherein at least a portion of the one or more cooling elements is configured to be implantable, and controlling the one or more cooling elements with a programmable controller configured to provide instructions to the one or more cooling elements in response to information regarding one or more physiological conditions of the vertebrate subject. The method can further include sensing with one or more sensors the information regarding the one or more physiological conditions and communicating the information from the one or more sensors to the programmable controller. The method can further include sensing with one or more sensors the information regarding the one or more physiological conditions and communicating the information from the one or more sensors to a digital processing unit, processing the information with the digital processing unit into at least one resulting instruction, and providing by the digital processing unit the at least one resulting instruction to the programmable controller. The method can further include receiving the information regarding the one or more physiological conditions from an outside operating source to a receiver including at least one of the programmable controller or a digital processing unit.

The outside operating source can include a computing device or a human operator. In the method, processing the information with the digital processing unit can include comparing the information regarding the one or more physiological conditions to information of a standard value or preprogrammed value. The information regarding the one or more physiological conditions can include a plasma level of one or more metabolic analytes in the vertebrate subject. The information regarding the one or more physiological conditions can include sugar levels or fatty acid levels in the vertebrate subject.

In the method, modulating the at least one activity of the brown adipose tissue can include increasing metabolic activity or increasing proliferation of brown adipose tissue in the vertebrate subject. In the method, modulating the at least one activity of the brown adipose tissue can include inducing non-shivering thermogenesis in the brown adipose tissue. The one or more tissues can include thermoresponsive tissue of the vertebrate subject. The method can further include powering the device with a power source.

The method can further include providing one or more medicaments for treatment of weight loss, metabolic disorder, diabetes, obesity, metabolic syndrome, dyslipidemia, or hypercholesterolemia, configured to be applied to the one or more tissues in combination with the one or more cooling elements of the device. The method can further include applying a neurostimulator to the one or more tissues. The method can further include applying a neurostimulator to one or more second tissues other than the one or more tissues. The one or more other tissues can include nerve tissue. In the method, applying the neurostimulator can include applying one or more of electric neurostimulator, magnetic neurostimulator, ultrasonic neurostimulator, or microwave neurostimulator.

A method for treating a metabolic disorder in a vertebrate subject is disclosed herein that includes applying cooling to one or more tissues of the vertebrate subject with one or more cooling elements, wherein the one or more cooling elements are configured to lower the temperature of the one or more tissues and thereby modulate at least one activity of brown adipose tissue of the vertebrate subject, wherein at least a portion of the one or more cooling elements is configured to be implantable, and controlling the one or more cooling elements with a programmable controller configured to provide instructions to the one or more cooling elements in response to information regarding one or more physiological conditions of the vertebrate subject. The method can further include sensing with one or more sensors the information regarding the one or more physiological conditions and communicating the information from the one or more sensors to the programmable controller. The method can further include sensing with one or more sensors the information regarding the one or more physiological conditions and communicating the information from the one or more sensors to a digital processing unit, processing the information with the digital processing unit into at least one resulting instruction, and providing by the digital processing unit the at least one resulting instruction to the programmable controller. The method can further include receiving the information regarding the one or more physiological conditions from an outside operating source to a receiver including at least one of the programmable controller or a digital processing unit.

The outside operating source can include a computing device or a human operator. In the method, processing the information with the digital processing unit can include comparing the information regarding the one or more physiological conditions to information of a standard value or preprogrammed value. The information regarding the one or more physiological conditions can include a plasma level of one or more metabolic analytes in the vertebrate subject. The information regarding the one or more physiological conditions can include sugar levels or fatty acid levels in the vertebrate subject. In the method, modulating the at least one activity of the brown adipose tissue includes increasing metabolic activity or increasing proliferation of brown adipose tissue in the vertebrate subject. In the method, modulating the at least one activity of the brown adipose tissue includes inducing non-shivering thermogenesis in the brown adipose tissue. The one or more tissues can include thermoresponsive tissue of the vertebrate subject. The method can further include powering the device with a power source.

The method can further include providing one or more medicaments for treatment of diabetes, obesity, metabolic syndrome, dyslipidemia, or hypercholesterolemia, configured to be applied to the one or more tissues in combination with the one or more cooling elements of the device. The method can further include applying a neurostimulator to the one or more tissues. The method can further include applying a neurostimulator to one or more second tissues other than the one or more tissues. The one or more other tissues can include nerve tissue. In the method, applying the neurostimulator can include applying one or more of electric neurostimulator, magnetic neurostimulator, ultrasonic neurostimulator, or microwave neurostimulator.

A system is disclosed herein that includes a non-transitory signal-bearing medium configured for use in a computing device including, one or more instructions for receiving data including data for applying cooling to one or more tissues of a vertebrate subject with one or more cooling elements of a treatment device, wherein the one or more cooling elements are configured to lower the temperature of the one or more tissues and thereby modulate at least one activity of brown adipose tissue of the vertebrate subject, wherein at least a portion of the one or more cooling elements is configured to be implantable; and one or more instructions for receiving data including data for controlling the one or more cooling elements with a programmable controller configured to provide instructions to the one or more cooling elements in response to information regarding one or more physiological conditions of the vertebrate subject. The system can further include one or more instructions for receiving data including data for sensing with one or more sensors the information regarding the one or more physiological conditions and communicating the information from the one or more sensors to the programmable controller. The system can further include one or more instructions for receiving data for the information regarding the one or more physiological conditions from an outside operating source to a receiver including at least one of the programmable controller or a digital processing unit.

The outside operating source can include a computing device or a human operator. In the system, the one or more instructions for receiving data for processing the information with the digital processing unit can include comparing the information regarding the one or more physiological conditions to information of a standard value or preprogrammed value. The information regarding the one or more physiological conditions can include a plasma level of one or more metabolic analytes in the vertebrate subject. The information regarding the one or more physiological conditions can include sugar levels or fatty acid levels in the vertebrate subject. In the system, modulating the at least one activity of the brown adipose tissue can include increasing metabolic activity or increasing proliferation of brown adipose tissue in the vertebrate subject. In the system, modulating the at least one activity of the brown adipose tissue can include inducing non-shivering thermogenesis in the brown adipose tissue. The system can further include one or more instructions for receiving data for implanting the programmable controller in the vertebrate subject. The system can further include one or more instructions for receiving data for implanting the programmable controller within a lumen of the vertebrate subject.

The system can further include one or more instructions for receiving data for implanting at least a portion of one or more cooling elements within a lumen of the vertebrate subject. The system can further include one or more instructions for receiving data for implanting the at least a portion of one or more cooling elements within a circulatory vessel of the vertebrate subject. The system can further include one or more instructions for receiving data for implanting the at least a portion of one or more cooling elements within a colon or a large intestine of the vertebrate subject. The one or more tissues can include thermoresponsive tissue of the vertebrate subject. The system can further include one or more instructions for receiving data for powering the device with a power source.

The system can further include one or more instructions for receiving data for providing one or more medicaments for treatment of weight loss, metabolic disorder, diabetes, obesity, metabolic syndrome, dyslipidemia, or hypercholesterolemia, configured to be applied to the one or more tissues in combination with the one or more cooling elements of the device. The system can further include one or more instructions for receiving data for applying a neurostimulator to the one or more tissues. The system can further include one or more instructions for receiving data for applying a neurostimulator to one or more second tissues other than the one or more tissues. The one or more other tissues can include nerve tissue. The system can further include one or more instructions for receiving data including data from at least one user interface. The system of claim 155, can further include one or more instructions for receiving data including data from at least one signal emitter. The system of claim 155, can further include one or more instructions for receiving data including data from digital memory.

A system is disclosed herein that includes one or more cooling elements configured to be applied to one or more tissues of a vertebrate subject to modulate at least one activity of brown adipose tissue of the vertebrate subject, wherein at least a portion of the one or more cooling elements is configured to be implantable, and a programmable controller configured to provide instructions to the one or more cooling elements in response to information regarding one or more physiological conditions of the vertebrate subject. The system can further include one or more sensors operably connected to the programmable controller, wherein the programmable controller is configured to provide instructions to the one or more cooling elements in response to information from the one or more sensors regarding the one or more physiological conditions of the vertebrate subject.

The system can further include a digital processing unit operably connected to the programmable controller, the digital processing unit configured to receive information from at least one of a sensor, a timekeeping device, a user interface, and an outside operating source, and configured to process the information into at least one resulting instruction and configured to provide the at least one resulting instruction to the programmable controller. The information regarding the one or more physiological conditions can include information regarding one or more analytes in the vertebrate subject. The information regarding the one or more physiological conditions can include a plasma level of one or more analytes in the vertebrate subject. The information regarding the one or more physiological conditions can include a level of one or more of a metabolic analyte, a sugar, a lipoprotein, or a fatty acid in the vertebrate subject. The information regarding the one or more physiological conditions can include information regarding the at least one activity of the brown adipose tissue. The programmable controller can be configured to receive information regarding the one or more physiological conditions from the one or more sensors.

The system can further include an outside operating source operably connected to the programmable controller, wherein the programmable controller in communication with the outside operating source is configured to provide instructions to the one or more cooling elements in response to information from the outside operating source regarding the one or more physiological conditions of the vertebrate subject. The system can further include at least one user interface. The system can further include at least one signal emitter. The system can further include digital memory.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1A:
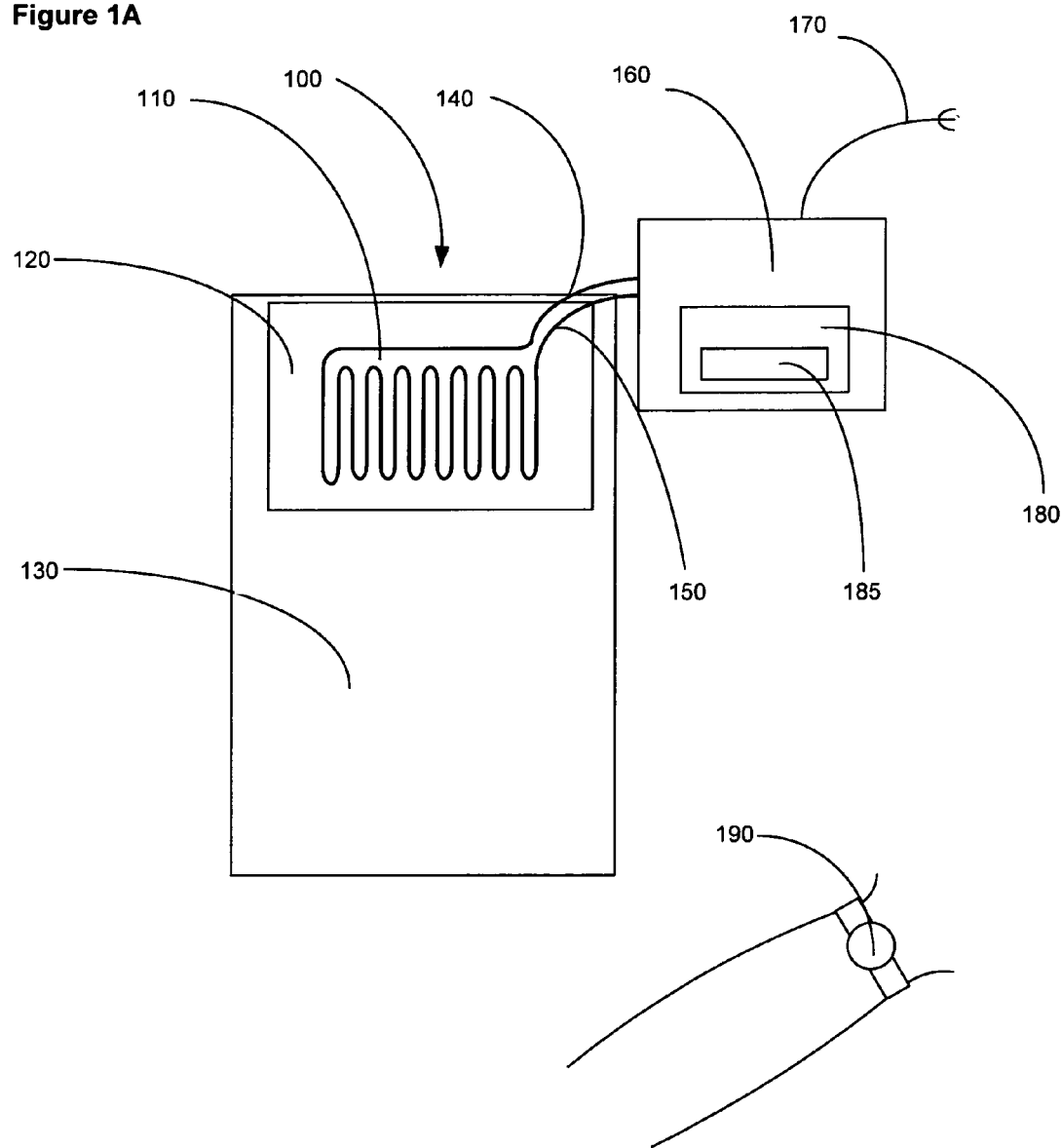
FIGS. 1A, 1B and 1C are a schematic of a diagrammatic view of an aspect of an embodiment of a device.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

This document uses formal outline headings for clarity of presentation. However, it is to be understood that the outline headings are for presentation purposes, and that different types of subject matter may be discussed throughout the application (e.g., method(s) may be described under composition heading(s) and/or kit headings, and/or descriptions of single topics may span two or more topic headings). Hence, the use of the formal outline headings is not intended to be in any way limiting.

A device is disclosed herein that can be used in a method for modulating an activity of brown adipose tissue in a vertebrate subject. The device can be used in a method for inducing weight loss in a vertebrate subject or in a method for treating a disorder, e.g., a metabolic disorder, diabetes, obesity, metabolic syndrome, or dyslipidemia, in a vertebrate subject. The device includes one or more cooling elements configured to be applied to one or more tissues of a vertebrate subject to modulate at least one activity of brown adipose tissue of the vertebrate subject, and a programmable controller configured to provide instructions to the one or more cooling elements in response to information regarding one or more physiological conditions of the vertebrate subject. The device can further comprise one or more sensors operably connected to the programmable controller, wherein the programmable controller is configured to provide instructions to the one or more cooling elements in response to information from the one or more sensors regarding one or more physiological conditions of the vertebrate subject.

A method for modulating an activity of brown adipose tissue of a vertebrate subject is disclosed herein that includes applying cooling to one or more tissues of the vertebrate subject with one or more cooling elements, wherein the one or more cooling elements are configured to lower the temperature of the one or more tissues and thereby modulate at least one activity of the brown adipose tissue of the vertebrate subject, controlling the one or more cooling elements with a programmable controller configured to provide instructions to the one or more cooling elements in response to information regarding one or more physiological conditions of the vertebrate subject.

A device is disclosed herein that includes one or more cooling elements configured to be applied to one or more tissues of a vertebrate subject to modulate at least one activity of brown adipose tissue of the vertebrate subject, wherein at least a portion of the one or more cooling elements is configured to be implantable, and a programmable controller configured to provide instructions to the one or more cooling elements in response to information regarding one or more physiological conditions of the vertebrate subject. The device can further include one or more sensors operably connected to the programmable controller, wherein the programmable controller is configured to provide instructions to the one or more cooling elements in response to information from the one or more sensors.

A method for modulating an activity of brown adipose tissue in a vertebrate subject is disclosed herein that includes applying cooling to one or more tissues of the vertebrate subject with one or more cooling elements, wherein the one or more cooling elements are configured to lower the temperature of the one or more tissues and thereby modulate at least one activity of the brown adipose tissue of the vertebrate subject, wherein at least a portion of the one or more cooling elements is configured to be implantable, and controlling the one or more cooling elements with a programmable controller configured to provide instructions to the one or more cooling elements in response to information regarding one or more physiological conditions of the vertebrate subject.

A device is disclosed herein that includes one or more passive cooling elements configured to be applied to one or more tissues of a vertebrate subject to modulate at least one activity of brown adipose tissue of the vertebrate subject, wherein at least a portion of the one or more passive cooling elements is configured to be implantable, and wherein the one or more passive cooling elements includes a first portion configured to be in association with the one or more tissues to be cooled, and a second portion configured to be placed in association with one or more tissues adjacent to an external epidermal tissue of the vertebrate subject. The second portion of the one or more passive cooling elements can further include one or more branches configured to be placed in association with the one or more tissues adjacent to the external epidermal tissue of the vertebrate subject.

A method for modulating an activity of brown adipose tissue in a vertebrate subject is disclosed herein that includes applying cooling to one or more tissues of the vertebrate subject with one or more passive cooling elements, wherein the one or more passive cooling elements are configured to lower the temperature of the one or more tissues and thereby modulate at least one activity of the brown adipose tissue of the vertebrate subject, wherein at least a portion of the one or more passive cooling elements is configured to be implantable, and wherein the one or more passive cooling elements includes a first portion configured to be in association with the one or more tissues to be cooled, and a second portion configured to be placed in association with one or more tissues adjacent to an external epidermal tissue of the vertebrate subject. The second portion of the one or more passive cooling elements can further include one or more branches configured to be placed in association with the one or more tissues adjacent to the external epidermal tissue of the vertebrate subject.

The device described herein includes one or more cooling elements configured to be applied to one or more tissues of a vertebrate subject to modulate at least one activity of brown adipose tissue, for example to enhance at least one activity of brown adipose tissue, for example to promote non-shivering thermogenesis in brown adipocytes of the vertebrate subject. The device can be used in a method for modulating an activity, e.g., a metabolic activity of brown adipose tissue of a vertebrate subject. The device can be used in a method for inducing weight loss in a vertebrate subject. The device can be used in a method for treating one or more disorders in a vertebrate subject including, but not limited to, overweightedness, obesity, a metabolic disorder, diabetes, dyslipidemia, and metabolic syndrome.

The device includes one or more cooling elements to be applied to one or more tissues of the subject, for example one or more tissues that include a thermoresponsive tissue, e.g., tissues having cold-sensitive thermoreceptors or sensory neurons. The one or more cooling elements can include, but are not limited to, one or more electrical cooling elements, one or more Peltier cooling elements, one or more chemical cooling elements. The one or more cooling elements can further include one or more heat pumps. The one or more cooling elements can include one or more nanoparticles, microparticles, paramagnetic particles, magnetic particles, chemical core particles, or one or more endothermic biodegradable particles. The one or more cooling elements can include one or more systems for passive cooling or active cooling using a heat sink or heat pipes.

The one or more cooling elements of the device can be applied to one or more tissues of a vertebrate subject. The one or more tissues can include one or more thermoresponsive tissue. The one or more tissues can include, but are not limited to, nervous tissue, cutaneous tissue, core tissue, brown adipose tissue, blood vessels, or combinations thereof. Cutaneous tissue can include, but is not limited to, epidermal tissue, dermal tissue, or highly vascularized dermal tissue. Core tissue can include, but is not limited to, any tissue internal to the body e.g., an organ in the viscera, or a deep vein, such as a great vein or a pulmonary vein. Blood vessels can be located in the core tissue, e.g., a deep vein, or in the cutaneous tissue of the vertebrate subject, and can include large blood vessels, e.g., superficial veins, such as saphenous vein.

The device described herein includes a programmable controller configured to provide instructions to the one or more cooling elements for cooling one or more tissues in a vertebrate subject. The device can further include a neurostimulator configured to be applied to the one or more tissues or to one or more other tissues in combination with the one or more cooling elements. The neurostimulator can include but is not limited to an electric neurostimulator, optical neurostimulator, a magnetic neurostimulator, an ultrasonic neurostimulator, or a microwave neurostimulator. In an aspect, the device can include one or more neurostimulators configured to stimulate nerves involved in inducing thermogenesis in brown adipose tissue. The neurostimulator can be in the same unit as the device that includes the one or more cooling elements, or the neurostimulator can be in a separate unit from the device that includes the one or more cooling elements. The neurostimulator can be applied to the one or more tissues to which the cooling elements have been applied. Alternatively or in addition, the neurostimulator can be applied to one or more second tissues of the vertebrate subject other than the one or more tissues. The neurostimulator can be applied to a tissue that includes a nervous tissue or to an innervated tissue.

The device can include a programmable controller operably connected to the one or more cooling elements, wherein the programmable controller is configured to provide instructions to the one or more cooling elements in response to information regarding one or more physiological conditions of the vertebrate subject. The device can further include one or more sensors operably connected to the programmable controller, wherein the programmable controller is configured to provide instructions to the one or more cooling elements in response to information from the one or more sensors regarding one or more physiological conditions of the vertebrate subject. The one or more physiological conditions can include a plasma level and/or localized tissue level of one or more analytes in the subject, which may be one or more metabolic analyte. In an aspect, the one or more analytes can include an analyte associated with a metabolic disorder. The one or more metabolic analyte indicative of a metabolic disorder include, but are not limited to, blood glucose, free fatty acids, triglycerides, insulin, glucagon, pro-inflammatory molecules, cholesterol, low density lipoprotein (LDL), and high-density lipoprotein (HDL), blood pressure, or heart rate. The one or more sensors are configured to provide data to the programmable controller regarding the plasma and/or tissue levels of metabolic analytes associated with a disorder, e.g., a metabolic disorder, diabetes, obesity, metabolic syndrome, or dyslipidemia, in the vertebrate subject.

Thermogenesis in Brown Adipose Tissue

Adipose tissue in mammals and some non-mammal vertebrates is composed of at least two distinct forms of adipose termed white adipose and brown adipose that differ significantly in both structure and function, as reviewed by Saely, et al., "Brown versus White Adipose Tissue: A Mini-Review," *Gerontology*, Karger A G, Basel, Dec. 7, 2010. White adipose tissue is the primary site of energy storage in the form of fat, and excess accumulation of fat in subcutaneous and visceral white adipose tissue depots leads to weight gain and obesity. White adipose tissue is also involved in releasing hormones and cytokines that modulate whole-body metabolism and insulin resistance. White adipocytes, the primary cellular component of white adipose tissue, are characterized by a single large lipid droplet. In contrast, brown adipose tissue is important for both basal and inducible energy expenditure in the form of thermogenesis (i.e., heat production) mediated by the activity of uncoupling protein 1 (UCP-1), a protein specifically expressed in brown adipose tissue. Increased metabolic activity of brown adipose tissue, e.g., in response to cold exposure or to diet, results in increased thermogenesis and heat production. Brown adipocytes, the primary cellular component of brown adipose tissue, are characterized by numerous small lipid droplets and much higher numbers of mitochondria relative to white adipocytes. Brown adipose tissue can affect whole-body metabolism and may alter insulin sensitivity and modify susceptibility to weight gain. Brown adipose tissue, for example, can have profound effects on body weight, energy balance, plasma triglyceride levels, and glucose metabolism. Ablation of the growth hormone secretagogue receptor (GHS-R), e.g., by genetic modification, has been associated with enhanced thermogenic capacity and an elevation in brown adipose tissue mitochondria and UCP-1 in older mice and but not in younger mice. This result suggests GHS-R is important in age related dysfunction of brown adipose tissue. See, e.g., Bartell et al., *Nat Med* (2011) January 23, doi:10.1038/nm.2297; Ma et al., *PLoS ONE* 6(1): e16391. doi:10.1371/journal.pone.0016391. 2011; Richard and Picard, *Frontiers in Bioscience* 16: 1233-1260, 2011; Nedergaard and Cannon *Cell Metab* 11(4): 268-72, 2010, Nedergaard, et al., *Am. J. Physiol. Endocrinol. Metab.* 293: E444-E452, 2007; Almind, et al., *Proc. Natl. Acad. Sci.,* 104: 2366-2371, 2007, each of which is incorporated herein by reference.

The device disclosed herein can include one or more cooling elements configured to be applied to one or more tissues of a vertebrate subject to modulate at least one activity of brown adipose tissue of the vertebrate subject. Modulating the at least one activity of the brown adipose tissue can include, but is not limited to, enhancing metabolic activity of brown adipose tissue, increasing metabolic activity of brown adipose tissue, or increasing proliferation of brown adipose tissue in the vertebrate subject. Modulating the at least one activity of the brown adipose tissue can include, but is not limited to, increasing one or more of adipogenesis, differentiation, non-shivering thermogenesis, or energy production of the brown adipose tissue in the vertebrate subject. Modulating the at least one activity of the brown adipose tissue can include modulating, e.g., increasing, non-shivering thermogenesis.

In rodents, brown adipose tissue tends to be localized within the interscapular, subscapular, renal, and paraspinal regions, whereas in humans the main depots of brown adipose tissue are supraclavicular, cervical, and paraspinal. Brown adipose tissue functions in cold- and diet-induced thermogenesis, which significantly contributes to the control of body temperature and energy expenditure (Richards and Picard, ibid). Thermogenesis in brown adipose tissue may represent a defense mechanism against obesity by increasing energy expenditure. Ablation of brown adipose tissue in rodents, for example by excision or by using a toxic gene, results in hyperphagia and obesity, supporting a role for brown adipose tissue in metabolic homeostasis. Likewise, the absence of brown adipose tissue activity is more apparent in overweight humans, in particular those of advancing age, correlating with obesity. In addition, a lack of UCP1 activity is sufficient to cause or aggravate obesity in mice. Considering the advances in studies into human brown adipose tissues, data regarding effects of brown adipose tissue on metabolism have been extrapolated to human biology, yielding explanations for human metabolic phenomena (see e.g. Nedergaard & Cannon, *Cell Metab.* 11(4): 268-272, 2010, which is incorporated herein by reference).

In human neonates, brown adipose tissue is readily detectable, and is known to provide thermal regulation in the early months following birth. The brown adipose tissue present at birth in humans decreases during normal development to adulthood, and, until recently, it was commonly thought that all brown adipose tissue was actually lost within the first few years of life. Newer technologies, including positron emission tomography (PET)-computed tomography (CT) and uptake of radioactive fluorodeoxyglucose (FDG), have now allowed the identification of metabolically active brown adipose tissues in human adults. Prospective studies using PET-CT with FDG uptake in healthy adult humans indicate high prevalence of brown adipose tissue in young adults, with detection of active brown adipose tissue less apparent in elderly (who tend to have higher bodyweight) and/or overweight persons. Both the presence and activity of the brown adipose tissues has been confirmed histologically. See, e.g., Saito, et al., *Diabetes* 58: 1526-1531, 2009 and Yoneshiro et al., *Obesity* 19: 13-16, 2011, which are incorporated herein by reference. Conversely, FDG uptake in humans can be inhibited or reversed by exposure to warm conditions. See e.g. Christensen et al., *Clin Nucl Med.* 2006 April; 31(4):193-6 and Nedergaard, et al., *Am. J. Physiol. Endocrinol. Metab.* 293:E444-E452, 2007, each of which is incorporated herein by reference. Studies indicate a high frequency of presence of brown adipose tissue in human adults. In addition, brown adipose tissue is more commonly detected in female, younger, and leaner individuals; fasting glucose levels are lower in individuals with apparent brown adipose tissue; and brown adipose tissue is more detectable in individuals with lower body weight and fasting glucose levels. Brown adipose tissue in humans and other animals is more active, and more detectable, at lower temperatures, a reflection of its role in cold-induced increases in energy expenditure. Brown adipose tissue is likely present in the majority of adult humans, with variations in activity and amount arising from factors including environment, age, weight, gender, and glucose levels. See, e.g., Lee, et al., *Am J Physiol Endocrinol Metab* 299: E601-E606, 2010; van Marken Lichtenbelt, et al., *N. Engl. J. Med.,* 360: 1500-1508, 2009; Cypess, et al., *N. Engl. J. Med.,* 360: 1509-1517, 2009, each of which is incorporated herein by reference.

In mammals, thermogenesis can be induced by thermoregulatory networks in response to a cold environment, a fall in core body temperature, and/or the presence of cytokines in certain tissues, e.g. brown adipose tissue. Temperature information is detected by thermoreceptors located in surface and core body parts and is transmitted to the peri-optic area (POA) of the hypothalamus. Environmental temperatures have direct and more rapid effects on skin temperature than on the temperatures within the body core, so that feedforward thermal afferents from the skin provide the POA with signals to rapidly initiate cold-defensive thermogenic responses before the body core temperatures are affected. Cutaneous thermoreception and its molecular mechanism in sensation utilize proteins from the transient receptor potential (TRP) family of cation channels, and different proteins are included in responses to different temperature ranges. Thermoreceptive mechanisms also exist in body core structures, including the brain, spinal cord and abdomen. The POA itself contains neurons whose activity is affected by local brain temperature, and temperature changes in the spinal cord can affect the activity of thermoregulatory neurons in the POA. Splanchnic and vagus nerve afferent fibers distributed in the abdomen and exhibit responses to temperature changes similar to those of cutaneous thermoreceptors, and visceral thermoreceptors are thought to be important in temperature regulation. Cold thermal receptors have been identified in different vagal territories including the gastrointestinal and respiratory tracts, and TRP channels are present in vagal afferent neurons associated with the gut and in the dorsal horn and dorsal root ganglia. Since responses in the core are not as rapid as in the skin, these receptors are likely to be involved in maintaining thermoregulation of basal temperature and in extreme or internal changes. Information from the peripheral and core thermoreceptors, then, travels various pathways to subdivisions of the POA responsible for thermoregulation, which can include both nonshivering (brown adipose tissue) and shivering thermogenesis. See, e.g., Morrison and Nakamura, *Front. Biosci.* 16: 74-104, 2011; Morrison, et al., *Exp. Physiol.* 93: 773-797, 2008; Zhang et al., Am J Physiol Gastrointest Liver Physiol 286: G983-G991, 2004; Fajardo, et al., The Journal of Neuroscience, Jul. 30, 2008 •28(31): 7863-7875; Choi & Seol, *J. Physiol. Anthropol.,* 20: 375-377, 2001; each of which is incorporated herein by reference.

Control of mammalian body temperature in a cold environment can be achieved, in part, through sympathetically regulated, nonshivering thermogenesis. Exposure to cold temperature signals the sympathetic nervous system, and triggers the release of catecholamine neurotransmitters, e.g., norepinephrine, that stimulates β-adrenergic receptors, initiating a cascade of intracellular events in the brown adipocytes and resulting in activation of the mitochondrial protein uncoupling protein 1 (UCP-1). UCP-1 is located in the inner mitochondrial membrane and serves to uncouple oxidative phosphorylation by promoting a proton leak across the mitochondrial membrane, thereby generating heat and lowering ATP synthesis. The major endogenous stimulator of UCP-1 expression and thermogenesis is the β-adrenergic stimulation mediated by catecholamines released from the sympathetic nervous system. β-adrenergic receptors are expressed predominantly in brown adipose tissue, and stimulation of these receptors increases oxygen consumption and UCP-1 mRNA expression. See, e.g., Nedergaard & Cannon, Cell Metab. 11(4): 268-272, 2010; Bartness, et al., International Journal of Obesity 34: 536-S42, 2010; Cannon & Nedergaard, Physiol. Rev. 84: 277-359, 2004; Morrison, et al., Exp. Physiol., 93: 773-797, 2008, each of which is incorporated herein by reference.

Increased detection and activity of brown adipose tissue has been observed in adult humans under exposure to cold. Thermogenesis in brown adipocytes appears to be a facultative process in that the tissue will be inactive in warm surroundings but will be acutely activated, within minutes, when an animal experiences a cold environment. See, e.g., Nedergaard; et al., Am. J. Physiol. Endocrinol. Metab. 293: E444-E452, 2007, and Cannon & Nedergaard, Physiol. Rev. 84: 277-359, 2004, which are incorporated herein by reference. In human subjects, for example, the metabolic activity of brown adipose tissue as measured by the uptake of $^{18}$F-fluorodeoxyglucose ($^{18}$F-FDG) and PET imaging is increased in subjects exposed to a cold environment just prior to the imaging analysis. See, e.g., Lee, et al., Am J Physiol Endocrinol Metab 299: E601-E606, 2010; Saito, of al., Diabetes 58:1526-1531, 2009; Yoneshiro et al., Obesity (2011) 19, 13-16, 2011; van Marken Lichtenbelt, et al., N. Engl. J. Med., 360:1500-1508, 2009; and Virtanen, et al., N. Engl. J. Med. 360:1518-1525, 2009, which are each incorporated herein by reference. The increased activity of brown adipose tissue in response to exposure to cold is facilitated by release of catecholamine neurotransmitters, e.g., norepinephrine, from the sympathetic nervous system in response to activation of cold-sensitive thermoreceptors in and on the body. The level of brown adipose tissue sympathetic nerve activity, and the norepinephrine release and receptor binding determine the level of thermogenesis by regulating both the activity of lipases providing the fuel to the mitochondria and the level of expression of UCP1 (Cannon & Nedergaard, Physiol. Rev. 84: 277-359, 2004, which is incorporated herein by reference.

Thermogenesis in brown adipose tissue can be regulated by the degree of activation and also by the capacity of the brown adipose tissue. The degree of activation can be determined by the acute rate of sympathetic stimulation and can be altered within seconds. The capacity of the brown adipose tissue is mainly determined by the chronic level of sympathetic stimulation of the tissue and needs days or weeks to be significantly altered. The total amount of brown adipose tissue, and thus the capacity for non-shivering thermogenesis, is a response to the environmental temperature to which the animal is chronically exposed. During long-term exposure, chronic adrenergic stimulation induces progenitor cells in the tissue to proliferate and brown preadipocytes to differentiate (which can also be stimulated by PPARg ligands), thereby increasing the total capacity of the tissue, a process referred to as recruitment. The differentiation program of brown adipocytes is characterized by induction of Ucp1 gene expression and mitochondrial biogenesis. Adaptive increases in brown adipose tissue amount and activity may be reflected in seasonal differences of FDG uptake by brown adipose in humans. In response to acute exposure to cold temperatures, activation of brown adipose tissue, e.g., via the β-adrenergic receptors, stimulates the synthesis of UCP-1 and mitochondrial proteins in the brown adipocytes. Mitochondrial mass can be experimentally increased in brown adipocytes using a beta adrenergic receptor agonist to activate the β-adrenergic receptors. See, e.g. Richard & Picard, Front Biosci., 16: 1233-60, 2011; Saito et al., ibid; Au-Yong et al., Diabetes 58: 2583-2587, 2009, each of which is incorporated by reference.

In general, the accumulation of white adipose tissue, for example due to an imbalance in caloric intake relative to energy expenditure, contributes to increased weight gain and obesity. The pathological accumulation of excess white adipose tissue that characterizes obesity is a major risk factor for the development of other diseases including Type 2 diabetes, cardiovascular disease, hypertension, stroke, arthritis, and various types of cancer. In contrast, brown adipose tissue evolved in mammals to dissipate large amounts of chemical energy as heat. In rodents, the metabolic activity of brown adipose tissue increases in response to feeding, essentially diet-induced adaptive thermogenesis, and may be a compensatory mechanism to limit excess weight gain and obesity. Rodents lacking the ability to undergo UCP-1 dependent thermogenesis are prone to obesity. In humans with limited detectable brown adipose tissue, this compensatory mechanism may be lacking, and as such, excessive caloric intake may lead to accumulation of fat and weight gain. Activation and/or proliferation of brown adipose tissue and increased thermogenesis may provide a mechanism for limiting and/or reducing weight gain and treating obesity and associated secondary diseases. See, e.g., Seale & Lazar, et al., Diabetes, 58: 1482-1484, 2009; Cannon & Nedergaard, Proc. Nutr. Soc., 68: 401-407, 2009, each of which is incorporated herein by reference.

Metabolically active brown adipocytes can take up glucose from the peripheral circulation. Cold exposure increases glucose utilization in brown adipose tissue by several fold and is dependent upon intact sympathetic innervations, e.g., localized release of norepinephrine. In humans, glucose, in the form of $^{18}$FDG as used for imaging by PET-CT, is taken up into metabolically active brown adipose tissue depots. Such uptake is increased at lower temperatures. See, e.g., Lee, et al., Am J Physiol Endocrinol Metab 299: E601-E606, 2010; Saito, et al., Diabetes 58: 1526-1531, 2009; Yoneshiro et al., Obesity (2011) 19, 13-16, 2011; van Marken Lichtenbelt, et al., N. Engl. J. Med., 360: 1500-1508, 2009; Cypess, et al., N Engl. J. Med., 360: 1509-1517; and Virtanen, et al., N. Engl. J. Med., 360: 1518-1525, each of which is incorporated herein by reference. Glucose uptake is also reduced by pretreatment with (3-adrenergic blockers. See, e.g., Parysow, et al., Clin Nucl Med. 2007 32(5): 351-7 and Söderlund, et al., J. of Nucl. Med. and Mol. Imag 34(7): 1018-1022, 2007. Likewise, the level of detectable brown adipose tissue appears to be inversely proportional to blood glucose levels. Individuals with little detectable brown adipose tissue have increased glucose levels. In patients scanned more than once, lower fasting glucose levels correlated with increased detectable brown adipose tissue (Lee et al., Am J Physiol Endocrinol Metab. 2010 October; 299(4): E601-6). The presence of metabolically active brown adipose tissue can lower the levels of glucose in the blood stream, which may have beneficial consequences for the treatment of diabetes and other metabolic disorders including metabolic syndrome. The treatment goal for both Type 1 and Type 2 diabetes is to maintain the levels of glucose at near normal levels. As such, controlled modulation of brown adipose tissue activity and thermogenesis can be a mechanism for controlling the levels of glucose in the blood stream and consequently treating metabolic disorders.

With reference to the figures, and with reference now to FIGS. 1 through 5, depicted is an aspect of a device, system, or method that can serve as an illustrative environment of and/or for subject matter technologies. The specific devices and methods described herein are intended as merely illustrative of their more general counterparts.

Referring to FIG. 1A, depicted is a partial diagrammatic view of an illustrative embodiment of a device 100 including one or more cooling elements 110 applied to one or more tissues of a vertebrate subject to modulate at least one activity of brown adipose tissue of the vertebrate subject. A programmable controller 180 is operably connected to the one or more cooling elements 110, wherein the programmable controller 180 is configured to provide instructions to the one or more cooling elements 110 in response to information regarding one or more physiological conditions of the vertebrate subject. The cooling elements 110 include flexible tubing incorporated into an item of furniture and/or bedding such as a pillow 120 on the bed 130 of the subject. The cooling elements 110 can contact thermoreceptors associated with the skin, e.g., facial skin, of the subject. The cooling elements 110 are connected through an outlet 140 and an inlet 150 through the pillow to a refrigeration unit 160 to provide a coolant, e.g., refrigerated water, through the flexible tubing of the cooling elements 110. The refrigeration unit 160 is connected to a power source 170. The power source can be one or more of a wired power source and/or a wireless power source and a power transducer. The programmable controller 180 includes an interface 185 that is configured to communicate with a hands-free unit 190 such as a piece of jewelry or wrist watch-like accessory on the subject's wrist. The hands-free unit 190 can include or communicate with sensors for monitoring a physiologic condition or indicator thereof such as the level of an analyte in blood, e.g., blood glucose, and/or the caloric intake or weight of the subject. The blood glucose levels or caloric intake can be monitored, for example, by transdermal sensing. The hands-free unit 190 can also or instead include or communicate with sensors configured to analyze content of an outside substance, for example a food substance about to be ingested, to gather information, for example information on caloric, nutritional, or sugar content. See, e.g., U.S. Patent Application 2010/0125420; 2010/0125419; U.S. 2010/0125418; U.S. 2010/0125417; each of which is incorporated herein by reference. The hands-free unit 190 can also use manual input of information, e.g., caloric intake and weight. The hands-free unit 190 can also use wired or wireless input, for example from a database, of information, e.g., caloric content of ingested food. Data collected by the hands-free unit 190 are wirelessly transmitted to the programmable controller 180 at the interface 185 at the end of the waking day.

Figure 1B:
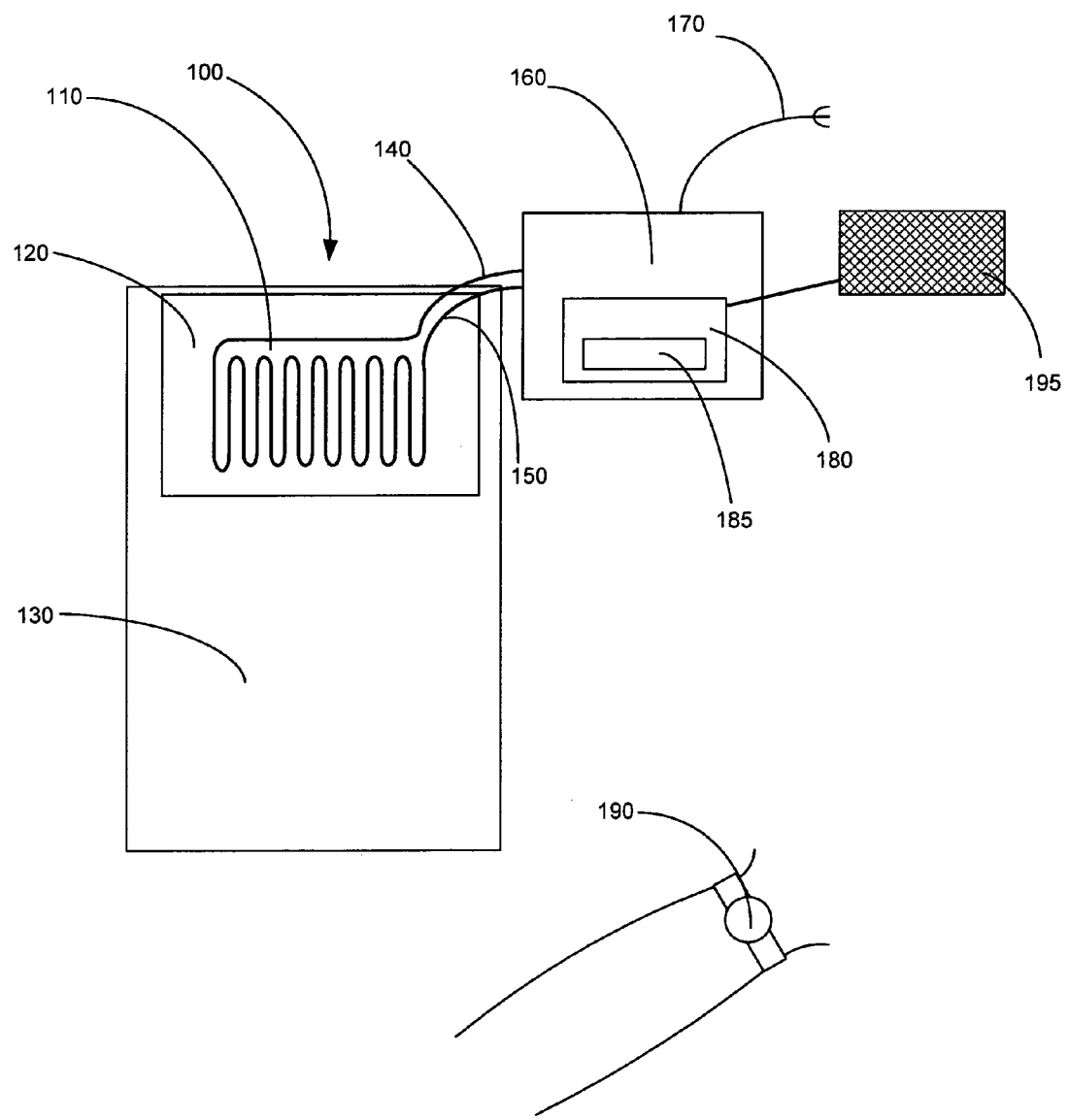

Referring to FIG. 1B, depicted is a partial diagrammatic view of an illustrative embodiment of a device 100 including one or more cooling elements 110 applied to one or more tissues of a vertebrate subject to modulate at least one activity of brown adipose tissue of the vertebrate subject. A programmable controller 120 is operably connected to the one or more cooling elements 110, wherein the programmable controller 180 is configured to provide instructions to the one or more cooling elements 110 in response to information regarding one or more physiological conditions of the vertebrate subject. A digital processing unit 195 is operably connected to the programmable controller 180. The digital processing unit 195 processes data, for example data collected by the hands-free unit 190 from user input or from sensors included in or communicating with the hands-free unit. The digital processing unit 195 processes data into one or more resulting instructions and provides the one or more instructions to the programmable controller 180. The digital processing unit 195 can be housed in the hands-free unit 190 and communicate with the hands-free unit 190 through circuitry and/or can communicate with the hands-free unit 190 through wired or wireless interface. The digital processing unit 195 can communicate with the programmable control 180 through wired or wireless interface. The cooling elements 110 include flexible tubing incorporated into an item of furniture and/or bedding such as a pillow 120 on the bed 130 of the subject. The cooling elements 110 can contact thermoreceptors associated with the skin, e.g., facial skin, of the subject. The cooling elements 110 are connected through an outlet 140 and an inlet 150 through the pillow to a refrigeration unit 160 to provide a coolant, e.g., refrigerated water, through the flexible tubing of the cooling elements 110. The refrigeration unit 160 is connected to a power source 170. The power source can be one or more of a wired power source and/or a wireless power source and a power transducer. The programmable controller 180 includes an interface 185 that is configured to communicate with a hands-free unit 190 such as a piece of jewelry or wrist watch-like accessory on the subject's wrist. The hands-free unit 190 can include or communicate with sensors for monitoring a physiologic condition or indicator thereof such as the level of an analyte in blood, e.g., blood glucose, and/or the caloric intake or weight of the subject. The blood glucose levels or caloric intake can be monitored, for example, by transdermal sensing. The hands-free unit can also or instead include or communicate with sensors configured to analyze content of an outside substance, for example, a food substance about to be ingested, to gather information, for example information on caloric or sugar content. The hands-free unit 190 can also use manual input of information, e.g., caloric intake and weight, into the device. The hands-free unit 190 can also use wired or wireless input of information, e.g., caloric content of ingested food. Data collected by the hands-free unit 190 are wirelessly transmitted to the programmable controller 180 via the interface 185, for example at the end of the waking day. In addition or instead, data collected by the hands-free unit 190 are communicated to the digital processing unit 195, and the digital processing unit 195 processes the data collected by the hands-free unit 190 into one or more resulting instruction and provides the one or more resulting instruction to the programmable controller 180.

Figure 1C:
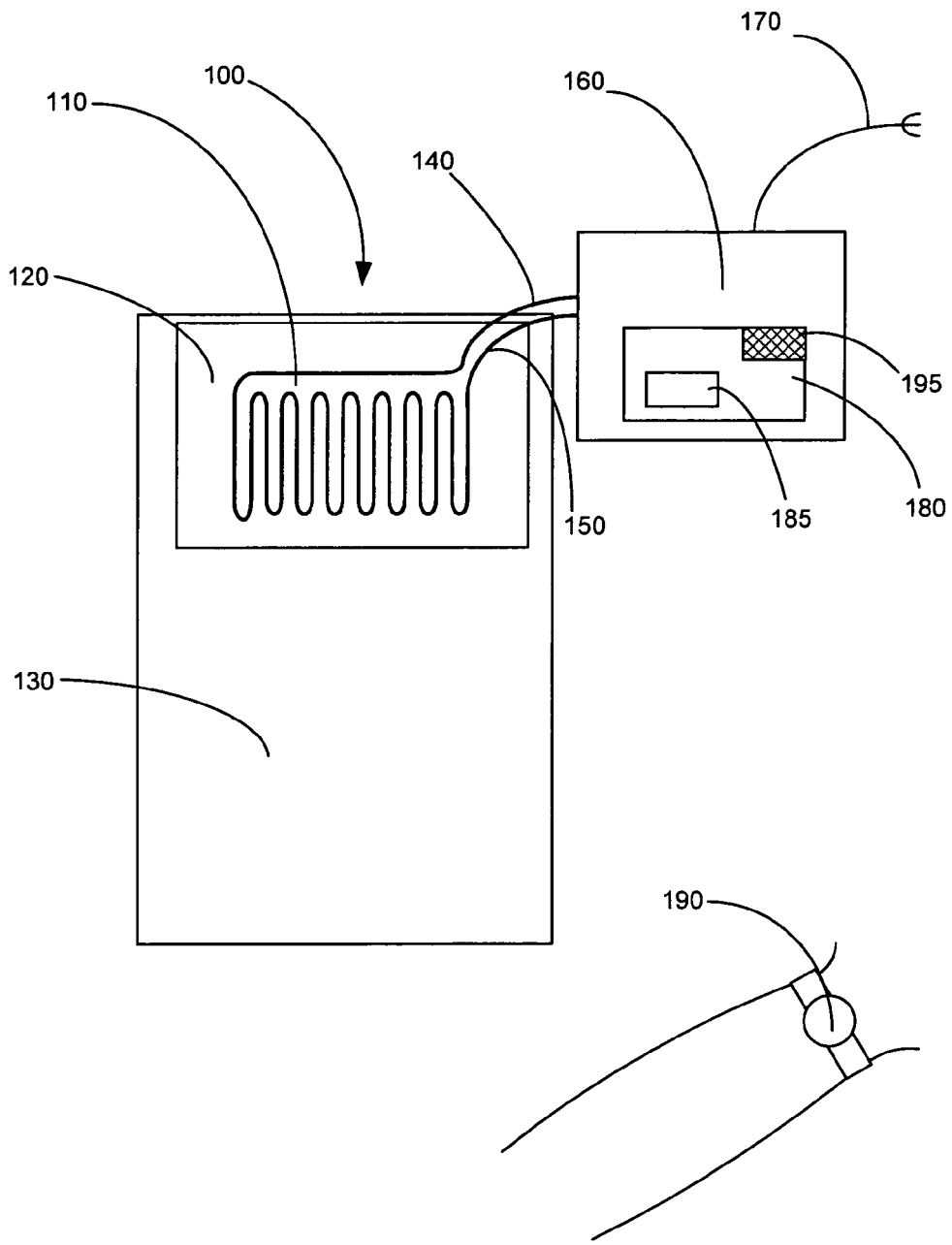

Referring to FIG. 1C, depicted is a partial diagrammatic view of an illustrative embodiment of a device 100 including one or more cooling elements 110 applied to one or more tissues of a vertebrate subject to modulate at least one activity of brown adipose tissue of the vertebrate subject. A programmable controller 120 is operably connected to the one or more cooling elements 110, wherein the programmable controller 180 is configured to provide instructions to the one or more cooling elements 110 in response to information regarding one or more physiological conditions of the vertebrate subject. A digital processing unit 195 is operably connected to the programmable controller 180. The device 100 of FIG. 1C operates in a similar manner to the device 100 of FIG. 1B, except that in the device 100 of FIG. 1C, the digital processing unit 195 is physically incorporated into a unit that includes the programmable controller 180. The digital processing unit 195 can be housed in or nearby the programmable controller 180, or can be incorporated into the programmable controller 180, and can communicate with the programmable controller 180 through circuitry and/or through wired or wireless interface. The digital processing unit 195 housed in or near the programmable control 180 can communicate, e.g. wirelessly, with the hands-free unit 190.

Figure 2:
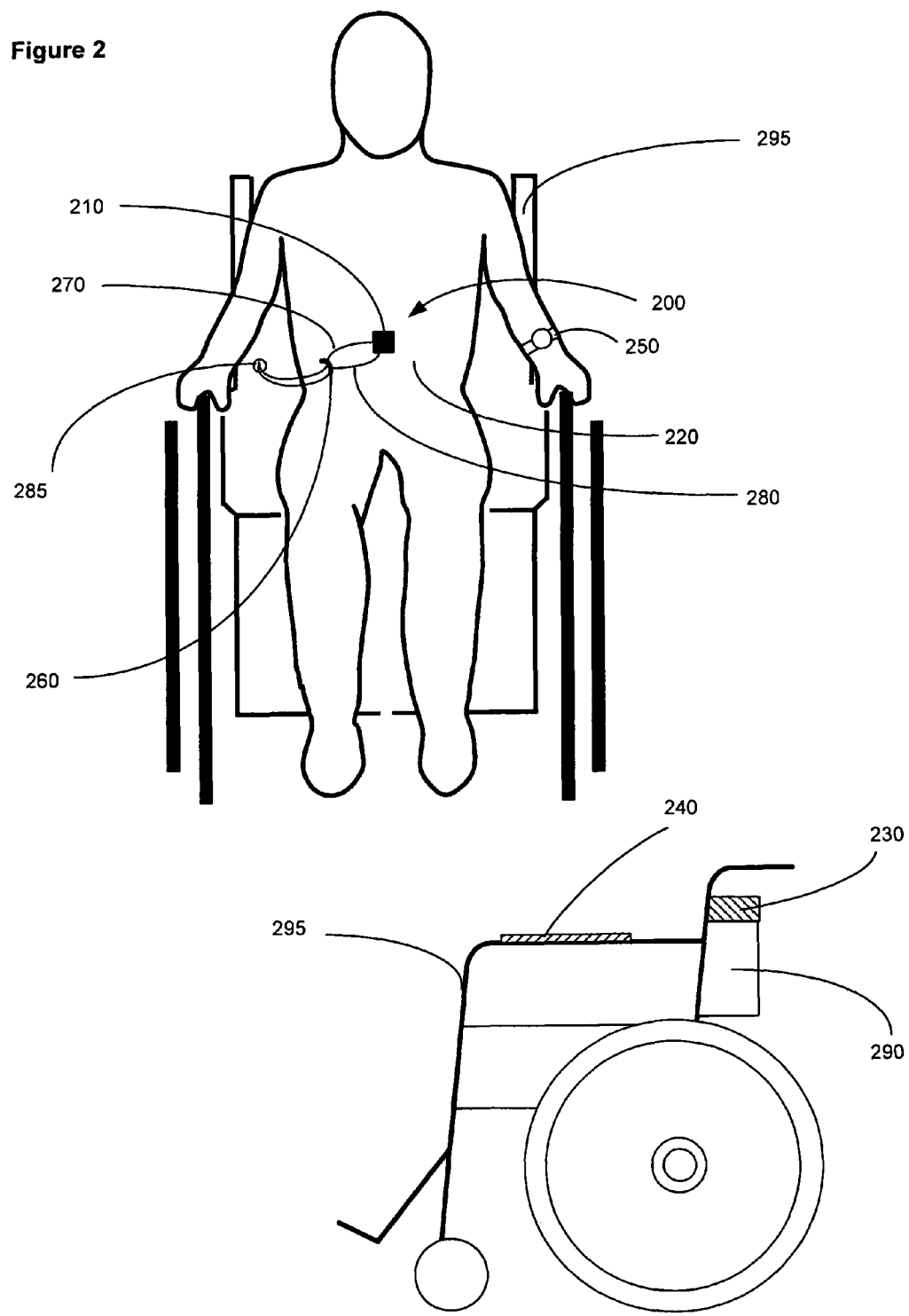
FIG. 2 is a schematic of a diagrammatic view of an aspect of an embodiment of a device.

Referring to FIG. 2, depicted is a partial diagrammatic view of an illustrative embodiment of a device 200 including one or more cooling elements 210 applied to an internal tissue 220, for example in the abdomen, of a vertebrate subject to modulate at least one activity of brown adipose tissue of the vertebrate subject to treat a disorder, e.g., a metabolic disease such as diabetes, in the vertebrate subject. The device includes a programmable controller 230 operably connected to the one or more cooling elements 210, wherein the programmable controller 230 is configured, e.g., through programming, to control the one or more cooling elements 210 in response to information regarding one or more physiological conditions of the vertebrate subject, e.g., information regarding blood glucose levels, caloric intake or weight of the vertebrate subject. At least a portion of the device is configured to be implantable 210. The programmable controller 230 can be accessed through a user interface 240 to provide programming or to provide information regarding the physiological condition, e.g., caloric intake or weight. The programmable controller 230 can be configured to interact with a sensor 250, for example an implanted sensor or external sensor for monitoring blood glucose. The programmable controller 230 can be configured or programmed to control the cooling elements 210 in response to information received from the sensor or from user input. An incision 260 in the skin of the subject acts as an entry point through the peritoneum for inlet cooling tubing 270 and outlet cooling tubing 280 including cooling fluid, e.g., water. The inlet cooling tubing 270 and outlet cooling tubing 280 are connected through a port 285 to a refrigeration unit 290 attached to a chair 295.

Figure 3:
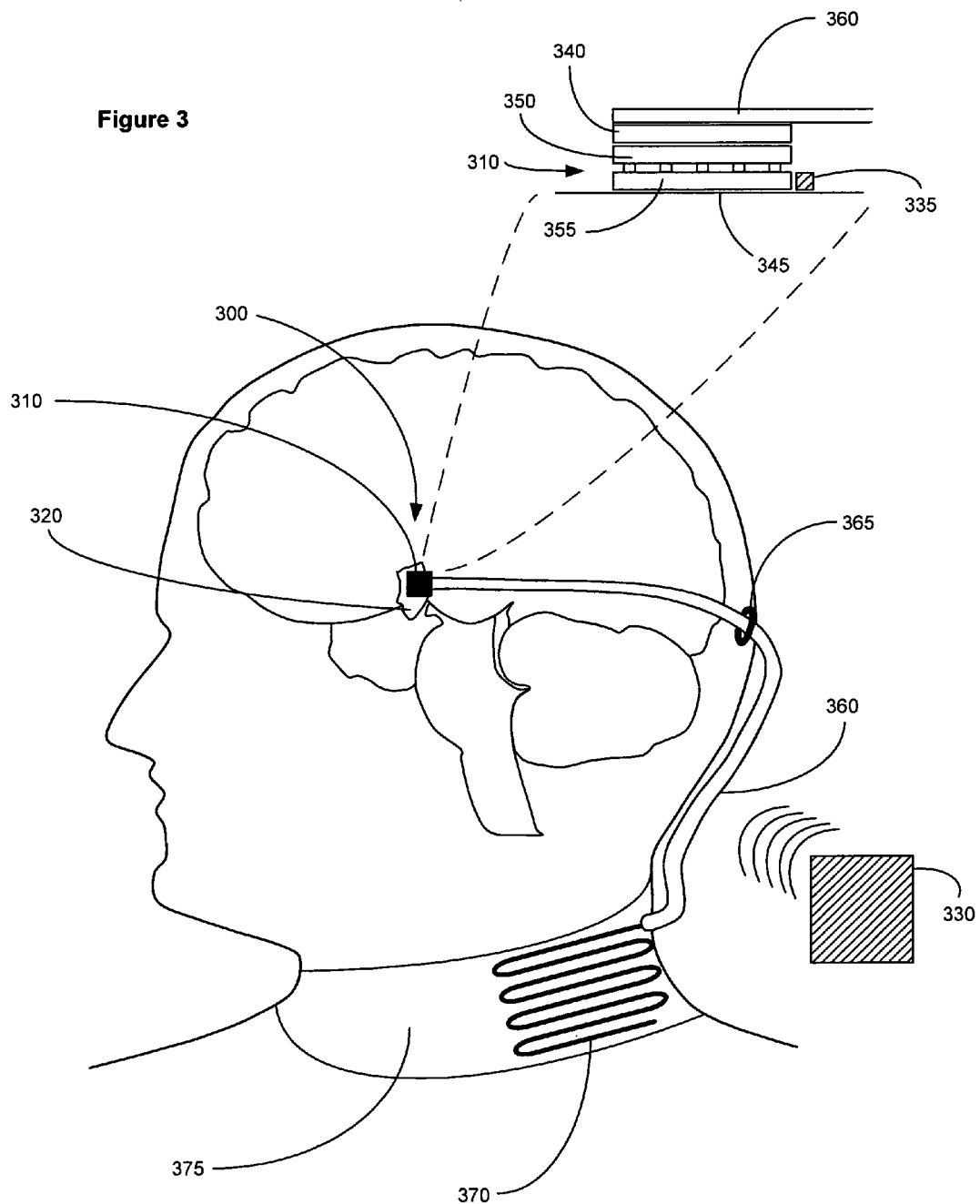
FIG. 3 is a schematic of a diagrammatic view of an aspect of an embodiment of a device.

Referring to FIG. 3, depicted is a partial diagrammatic view of an illustrative embodiment of a device 300 including one or more cooling elements 310, e.g., one or more Peltier devices, configured to be applied to a nervous tissue, e.g. a hypothalamus 320, in the brain of a vertebrate subject to controllably cool the hypothalamus 320 and to modulate at least one activity of brown adipose tissue of the vertebrate subject to treat a metabolic disease, e.g., diabetes, in the vertebrate subject. The device includes a programmable controller 330 operably connected to the one or more cooling elements 310. The programmable controller 330 is operably connected to a thermocouple sensor probe 335 and is configured, e.g., programmed, to control the one or more cooling elements 310 in response to information regarding one or more physiological conditions, e.g., a core temperature, of the vertebrate subject. At least a portion of the device is configured to be implantable into the pre-optic area (POA) of the hypothalamus 320 of the subject. Direct cooling of the local environment of the POA evokes activation and thermogenesis in brown adipose tissue. See, e.g., Morrison & Nakamura, Frontiers in Bioscience 16: 74-104, 2011; Boulant & Dean, Ann. Rev. Physiol. 48: 639-654, 1986; Passlick-Deetjen & Beddenbender-Stoll, Nephrol. Dial. Transplant., 20: 1784-1789, 2005; each of which is incorporated herein by reference. The implantable cooling element includes a chip-sized Peltier cooling element 310 measuring approximately 6 mm by 6 mm can be combined with a fine thermocouple probe 335 and a copper heat sink 340. The cooling surface 355 of the Peltier device is close to or in contact with a tissue surface 345 of the subject. This portion of the cooling element can be covered with a fine layer of medical silicone or other biocompatible membrane. The copper heat sink 340 is positioned on the heat dissipating side 350 of the Peltier element and the heat from the copper heat sink 340 is transferred to a circulating fluid that is part of a microchannel cooling system 360 flowing between the implanted portion of the cooling element through a port 365 to a location on the exterior 370 of the subject onto a neck wrap 375 at the nape of the neck of the subject. Internal heat transferred from the Peltier element 310 into the circulating fluid 360 is transferred to the external ambient environment through a series of tubes 370 associated with the microchannel cooling system. The thermocouple sensor 335 is used to measure the temperature of the hypothalamus tissue 320 as it is being cooled and can be included in a closed loop system to modulate the activity of the Peltier element 310 to maintain a desired tissue temperature. The thermocouple sensor 335 can be connected to a programmable controller 330 of the device. The programmable controller 330 is located on the exterior of the subject and is incorporated into a dedicated-use handheld device. The handheld programmable controller 330 includes a user interface allowing for input and receipt of information. The handheld programmable controller 330 is operably connected to the Peltier element 310 and the thermocouple sensor 335 via wireless radio frequency.

Figure 4:
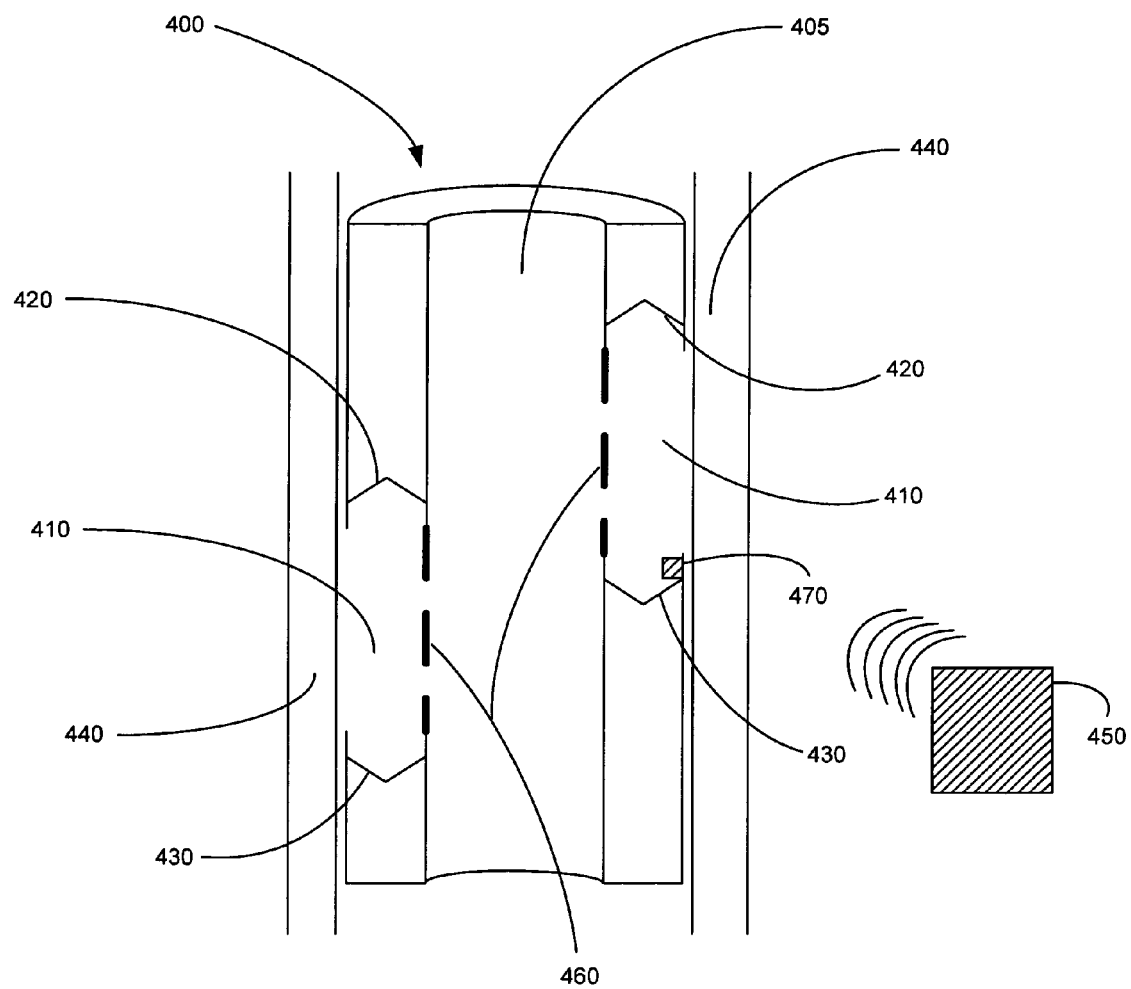
FIG. 4 is a schematic of a diagrammatic view of an aspect of an embodiment of a device.

Referring to FIG. 4, depicted is a partial diagrammatic view of an illustrative embodiment of a device 400 including one or more cooling elements 410, e.g., endothermal chemical components, configured to be applied to a lumenal tissue, e.g. a colon 440, of a vertebrate subject to controllably cool the tissue and to modulate at least one activity of brown adipose tissue of the vertebrate subject to treat a disorder, e.g. a metabolic disease such as diabetes, in the vertebrate subject. The device includes a programmable controller 450 operably connected to the one or more cooling elements 410, wherein the programmable controller 450 is operably connected to a sensor 470 configured to monitor a physiological condition or indicator thereof such as the level of an analyte, e.g. blood glucose, in the subject. The programmable controller 450 can control the one or more cooling elements 410 in response to information received from the sensors regarding the one or more physiological conditions of the vertebrate subject. At least a portion of the device 400 is configured to be implantable into the colon 440 of the subject. The device includes an implantable portion implanted into the colon having a cooling element 410 containing an endothermal chemical composition. The implantable portion of the device 400 resembles a self-expanding stent including an internal lumen 405 for insertion into the lower colon. The implantable portion 400 of the device includes two sets of micro-reservoirs, 420 and 430, each containing a distinct endothermic chemical, e.g., citric acid and sodium bicarbonate, which upon mixing in a common chamber 410 draw heat from the surrounding environment resulting in cooling. The micro-reservoirs, 410, 420, and 430, are incorporated into the wall of the stent-like structure. Each micro-reservoir, 420, and 430, containing either citric acid or sodium bicarbonate is covered with a gold foil which in the presence of a triggering event, e.g., a voltage, dissolves and releases the contents of the micro-reservoir. The common chamber 410 is in direct contact with the luminal surface of the colon allowing for localized cooling. The common chamber 410 also includes a semi-permeable diffusion membrane 460 through which the byproducts of the endothermic reaction can diffuse out of the chamber 410 and into the lumen of the colon 440.

Figure 5:
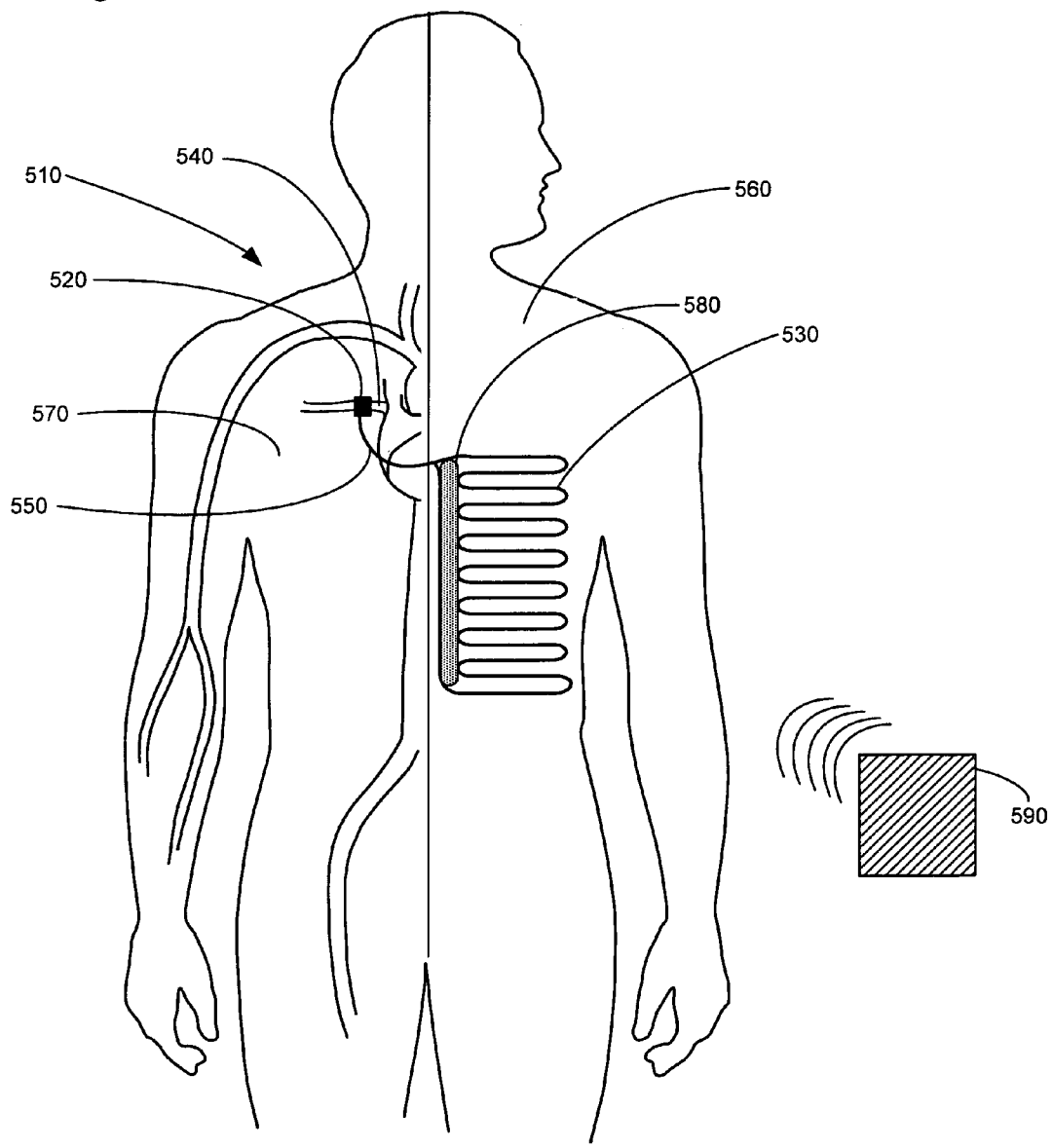
FIG. 5 is a schematic of a diagrammatic view of an aspect of an embodiment of a device.

Referring to FIG. 5, depicted is a partial diagrammatic view of an illustrative embodiment of a device having a programmable controller for cooling an area of the body of a human subject to treat a disorder, e.g., a metabolic disorder such as metabolic syndrome, in the human subject. Over time the device can further modulate activity of brown adipose tissue by inducing proliferation and differentiation of adipocytes thus increasing the mass and total activity of the brown adipose tissue. The device can include one or more passive cooling elements 510, including a deep portion 520 and a shallow portion 530, configured to be applied to the pulmonary vein 540 and thermoreceptors therein, to cool the tissues and to enhance at least one activity of brown adipose tissue of the vertebrate subject with minimal energy input to the device. The device includes a first portion 520 of the one or more passive cooling elements is configured to be in association with deep tissue, e.g., pulmonary vein tissue 540, to be cooled, and a second portion 530 of the one or more passive cooling elements is configured to be in association with one or more tissues adjacent to an external epidermal tissue 560 of the vertebrate subject, and wherein at least a portion 520 of the device is configured to be implantable. The passive cooling system includes a series of tubes 550 and a low-energy pump 580 that can circulate a fluid, e.g., water in a closed loop through the deep and shallow portions of the system. The deep portion 520 of the passive cooling system is implanted in close proximity to or in direct contact with the pulmonary vein 540. The shallow portion 530 of the passive cooling system is implanted just below the surface of the skin 560 where the temperature of the subject is closer to ambient temperature and heat exchange with the external environment is possible. The shallow portion 530 of the passive cooling system is configured in a tentacle-like structure, allowing the fluid to be spread out over a larger surface area 560 to encourage more rapid cooling or equilibrium with the outside environment. The fluid in the passive cooling system is pumped by a pump 580 from the relatively cooler environment of the shallow portion to the relatively warmer environment of the deep portion of the device. The pump 580 for circulating the fluid through the implanted passive cooling system can be powered by a body heat energy generator incorporated into the implanted portion of the device. The device further includes an external programmable controller 590 mounted into the armrest of the subject's chair or into a watchband. The programmable controller 590 is configured to send wireless instructions to the implanted passive cooling system 510.

Figure 6:
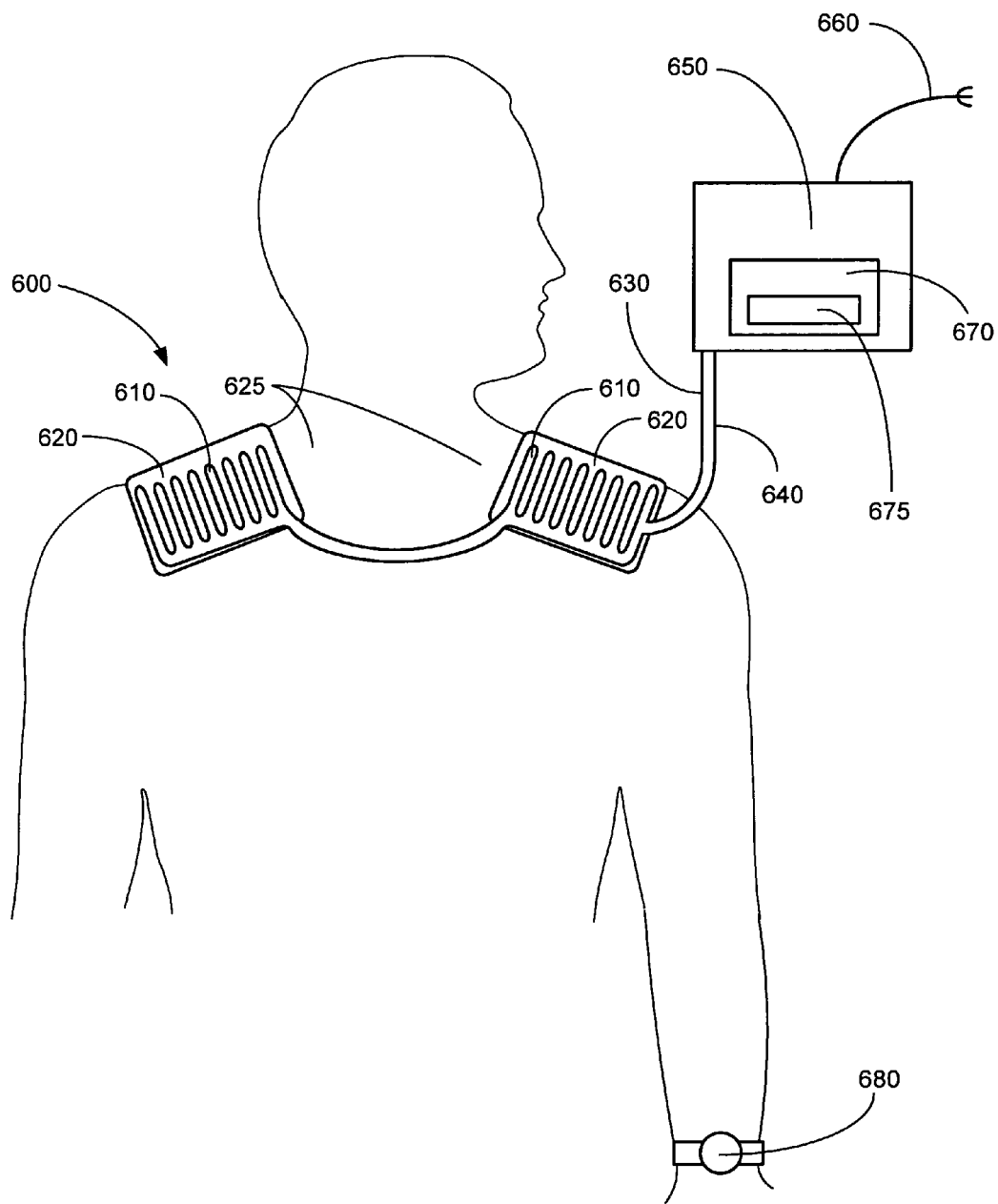
FIG. 6 is a schematic of a diagrammatic view of an aspect of an embodiment of a device.

Referring to FIG. 6, depicted is a partial diagrammatic view of an illustrative embodiment of a device 600 including one or more cooling elements 610 configured to be applied to one or more external tissues of a human subject, for example an external skin surface 625 such as that located in a suprascapular region of a human subject, to modulate at least one activity of brown adipose tissue of the human subject. A programmable controller 670 is operably connected to the one or more cooling elements 610 and is configured to control the one or more cooling elements 610 in response to information regarding one or more physiological conditions of the human subject. The cooling elements 610 are applied externally to the skin in the suprascapular region of the human subject. The cooling elements 610 include flexible tubing incorporated into a flexible padded substrate 620 and are applied externally to the skin in the suprascapular region of the human subject. The cooling elements 610 can contact thermoreceptors associated with the skin of the subject. The cooling elements 610 include tubing connected through an outlet 630 and an inlet 640 through the padded substrate 620 and through a refrigeration unit 650 that provides cooling to a coolant, e.g., refrigerated water, that flows through the flexible tubing of the cooling elements 610. The refrigeration unit 650 is connected to a power source 660. The power source 660 can be one or more of a wired power source and/or a wireless power source and transducer. The programmable controller 670 includes a user interface 675 that is configured to communicate with a hands-free unit 680 such as a piece of jewelry or wrist watch-like accessory on the subject's wrist. The hands-free unit 680 can include or communicate with sensors for monitoring a physiologic condition or indicator thereof, such as the level of an analyte in blood, e.g., glucose, and/or the caloric intake or weight of the subject. The blood glucose levels can be monitored, for example, by a transdermal sensor. The hands-free unit 680 can also, or instead, include or communicate with sensors configured to analyze content of an outside substance, for example a food substance about to be ingested, to gather information, e.g., information on caloric or sugar content. See, e.g., U.S. Patent Application 2010/0125420; 2010/0125419; U.S. 2010/0125418; U.S. 2010/0125417; each of which is incorporated herein by reference. The hands-free unit 680 can also use manual input of information, e.g., caloric intake and weight, entered into the device. The hands-free unit 680 can also receive wired or wireless input of information, e.g., caloric content of ingested food provided by a database in a personal computing device. The hands-free unit 680 can also utilize manual input of information, e.g. caloric intake and weight, into the device. Information collected by the hands-free device 680 is wirelessly transmitted to the programmable controller 670 at the user interface 675, for example at the end of the waking day or at other predetermined times.

Figure 7:
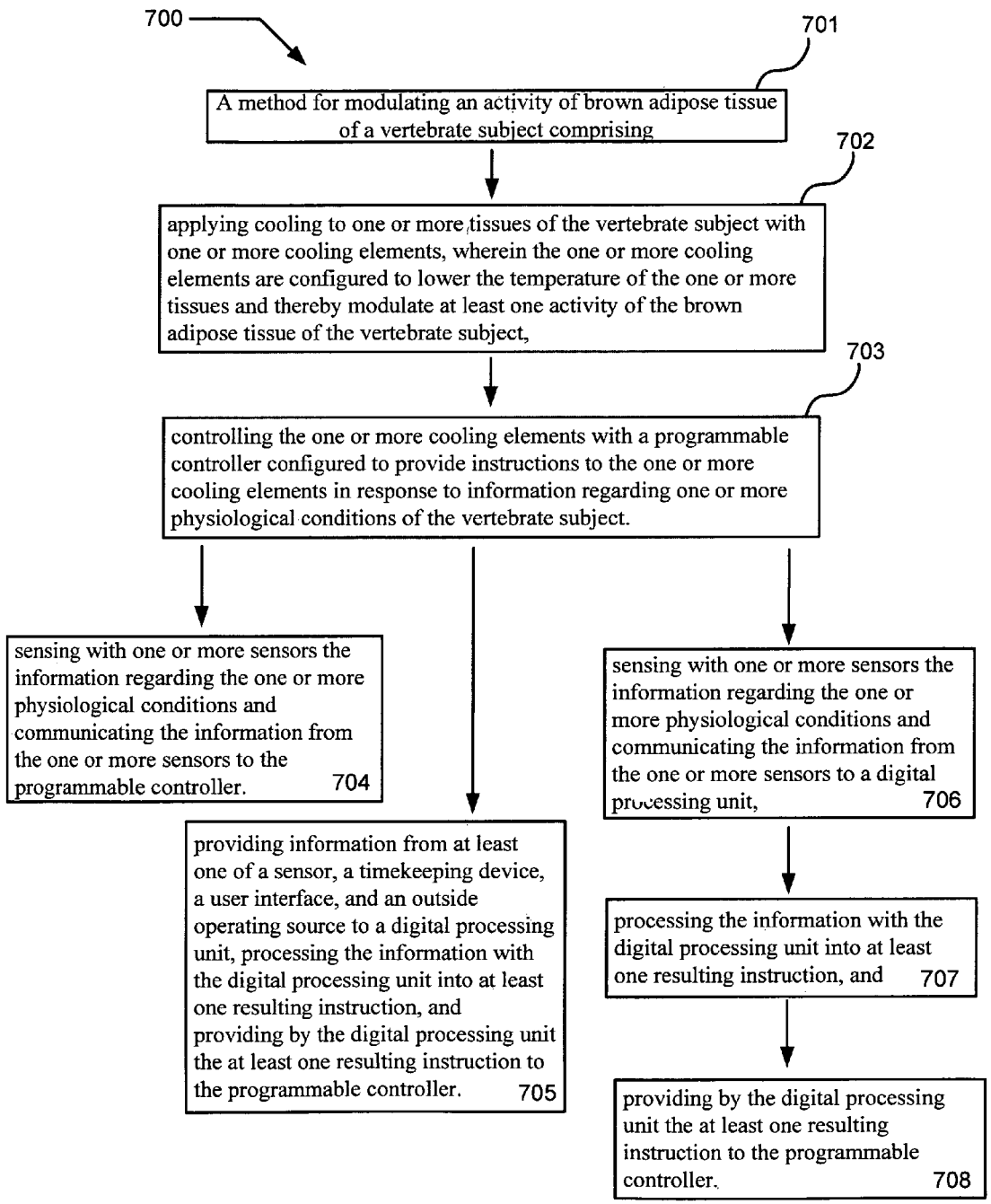
FIG. 7 is a schematic of a diagrammatic view of an aspect of an embodiment of a method for treating a metabolic disorder in a vertebrate subject.

Referring to FIG. 7, depicted is a partial diagrammatic view of an illustrative embodiment of a method 701 for modulating an activity of brown adipose tissue of a vertebrate subject comprising applying 702 cooling to one or more tissues of the vertebrate subject with one or more cooling elements, wherein the one or more cooling elements are configured to lower the temperature of the one or more tissues and thereby modulate at least one activity of the brown adipose tissue of the vertebrate subject, and controlling 703 the one or more cooling elements with a programmable controller configured to provide instructions to the one or more cooling elements in response to information regarding one or more physiological conditions of the vertebrate subject. The method can further include sensing 704 with one or more sensors the information regarding the one or more physiological conditions and communicating the information from the one or more sensors to the programmable controller. The method can further include sensing 706 with one or more sensors the information regarding the one or more physiological conditions and communicating the information from the one or more sensors to a digital processing unit, processing 707 the information with the digital processing unit into at least one resulting instruction, and providing 708 by the digital processing unit the at least one resulting instruction to the programmable controller. The method can further include providing 705 information from at least one of a sensor, a timekeeping device, a user interface, and an outside operating source to a digital processing unit, processing the information with the digital processing unit into at least one resulting instruction, and providing by the digital processing unit the at least one resulting instruction to the programmable controller.

Figure 8:
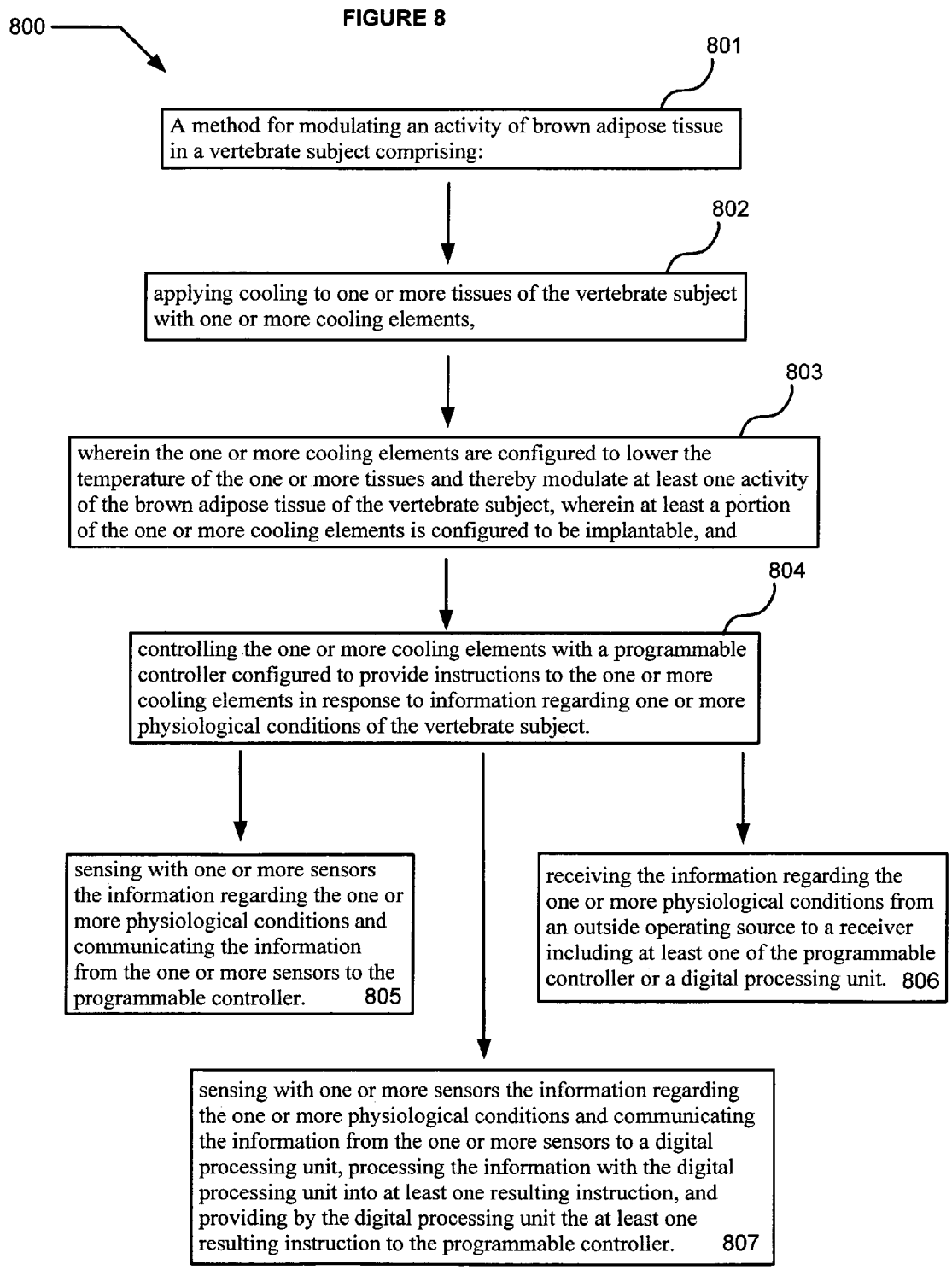
FIG. 8 is a schematic of a diagrammatic view of an aspect of an embodiment of a method for treating a metabolic disorder in a vertebrate subject.

Referring to FIG. 8, depicted is a partial diagrammatic view of an illustrative embodiment of a method 801 for modulating an activity of brown adipose tissue in a vertebrate subject, where the method includes applying 802 cooling to one or more tissues of the vertebrate subject with one or more cooling elements, wherein the one or more cooling elements 803 are configured to lower the temperature of the one or more tissues and thereby modulate at least one activity of the brown adipose tissue of the vertebrate subject, wherein at least a portion of the one or more cooling elements is configured to be implantable, and controlling 804 the one or more cooling elements with a programmable controller configured to provide instructions to the one or more cooling elements in response to information regarding one or more physiological conditions of the vertebrate subject. The method further includes sensing 805 with one or more sensors the information regarding the one or more physiological conditions and communicating the information from the one or more sensors to the programmable controller. The method further includes sensing 807 with one or more sensors the information regarding the one or more physiological conditions and communicating the information from the one or more sensors to a digital processing unit, processing the information with the digital processing unit into at least one resulting instruction, and providing by the digital processing unit the at least one resulting instruction to the programmable controller. The method further includes receiving 806 the information regarding the one or more physiological conditions from an outside operating source to a receiver including at least one of the programmable controller or a digital processing unit.

Figure 9:
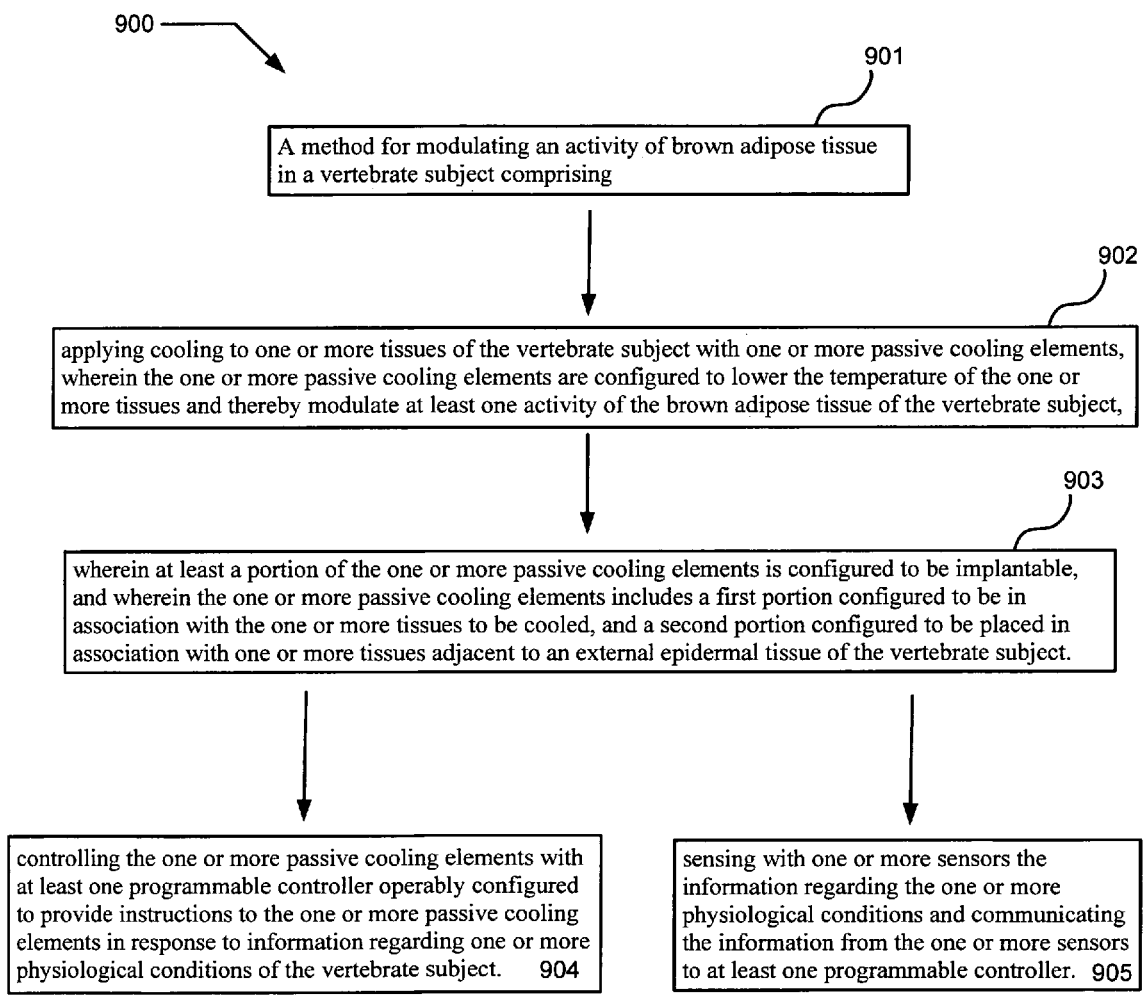
FIG. 9 is a schematic of a diagrammatic view of an aspect of an embodiment of a method for treating a metabolic disorder in a vertebrate subject.

Referring to FIG. 9, depicted is a partial diagrammatic view of an illustrative embodiment of a method 901 for modulating an activity of brown adipose tissue in a vertebrate subject, where the method includes applying 902 cooling to one or more tissues of the vertebrate subject with one or more passive cooling elements, wherein the one or more passive cooling elements are configured to lower the temperature of the one or more tissues and thereby modulate at least one activity of the brown adipose tissue of the vertebrate subject, wherein at least a portion of the one or more passive cooling elements 903 is configured to be implantable, and wherein the one or more passive cooling elements includes a first portion configured to be in association with the one or more tissues to be cooled, and a second portion configured to be placed in association with one or more tissues adjacent to an external epidermal tissue of the vertebrate subject. The method can further include controlling 904 the one or more passive cooling elements with at least one programmable controller operably configured to provide instructions to the one or more passive cooling elements in response to information regarding one or more physiological conditions of the vertebrate subject. The method can further include sensing 905 with one or more sensors the information regarding the one or more physiological conditions and communicating the information from the one or more sensors to at least one programmable controller.

Method for Treating One or More Disorders

The device described herein, including one or more cooling elements configured to be applied to one or more tissues of a vertebrate subject to modulate at least one activity of brown adipose tissue of the vertebrate subject, and a programmable controller configured to provide instructions to the one or more cooling elements in response to information regarding one or more physiological conditions of the vertebrate subject can be used in a method for treating one or more disorders in the vertebrate subject. The one or more disorders include, but are not limited to, metabolic disorder, overweightedness, obesity, diabetes, dyslipidemia, and metabolic syndrome. Obesity refers to a medical condition in which excess body fat has accumulated to the extent that it may have an adverse effect on health, leading to reduced life expectancy and/or increased health problems. Obesity is defined as a function of body weight relative to height (weight in kilograms/height$^2$ in meters) as represented by the body mass index (BMI). Individuals with a BMI equal to or exceeding 30 kg/m$^2$ are considered obese whereas individuals with a BMI ranging from 25 kg/m$^2$ to 29.9 kg/m$^2$ are considered overweight. Obesity can be further classified as class I (BMI of 30.0-34.9 kg/m$^2$), class II (BMI of 35.0-39.9 kg/m$^2$), and class III (BMI of equal to or greater than 40 kg/m$^2$). The risk of developing type 2 diabetes, hypertension and cardiovascular disease increases with increasing BMI. See, e.g., Poirier, et al., *Circulation,* 113:898-918, 2006, which is incorporated herein by reference.

Metabolic disorder generally refers to a broad array of disorders characterized by defects that interfere with the body's metabolism, the chemical processes by which a body transforms proteins, carbohydrates and fats into energy. Inherited metabolic disorders are often the result of inherited genetic defects. Examples of inherited metabolic disorders include Tay-Sachs Disease, Leukodystrophies, Lysosomal Disorders, and Lipid Storage Disorders, see e.g., information posted on the National Library of Medicine of the National Institutes of Health Medline Plus website entitled "Metabolic Disorders" (http://www.nlm.nih.gov/medlineplus/metabolicdisorders.html#cat1), which was accessed on Feb. 17, 2011. A metabolic disorder can result from a diseased or dysfunctional organ. Diabetes is an example of a metabolic disorder resulting from a diseased and/or dysfunctional organ, the pancreas. Additional examples of metabolic disorders may include but are not limited to obesity, metabolic syndrome, impaired glucose tolerance, and dyslipidemias. See, e.g. Golden, et al., *J. Clin. Endocrinol. Metab.* 94: 1853-1878, 2009, which is herein incorporated by reference.

Diabetes, especially diabetes mellitus, refers to a disorder of carbohydrate metabolism and is characterized excessive amounts of glucose in the blood. The two main types of chronic diabetes are Type 1 or insulin-dependent diabetes and Type 2 or noninsulin-dependent diabetes. Type 1 diabetes is characterized by selective destruction of insulin-producing β-cells in the pancreas and severe or absolute insulin deficiency. Individuals with Type 1 diabetes are dependent on daily insulin administration to keep glucose levels at a near normal level. Type 2 diabetes is characterized by tissue resistance to the action of insulin combined with a relative deficiency in insulin secretion. A given individual may have more resistance or more β-cell deficiency, and the abnormality may be mild or severe. Although insulin is produced in these patients, it is inadequate to overcome the resistance and the blood glucose rises. The impaired insulin action can also affect fat metabolism resulting in increased free fatty acid flux and triglyceride levels and reciprocally low levels of high-density lipoprotein (HDL). A major risk factor for the development of Type 2 diabetes is being overweight or obese. In addition to chronic forms of diabetes, temporary or early forms of diabetes can occur including prediabetes, which presents with blood sugar levels are higher than normal but not high enough to be classified as diabetes, and gestational diabetes, which occurs during pregnancy.

Dyslipidemia refers to abnormal concentrations of lipids in the blood. Dyslipidemia can manifest as hyperlipidemia and can include an elevation of plasma cholesterol (hypercholesterolemia), triglycerides (hyperglyceridemia), or both. Dyslipidemia can include elevated or abnormal levels of lipoproteins including low-density lipoprotein (LDL; "bad") or high-density lipoprotein (HDL; "good"). In Western society, most cases of dyslipidemia are instances of hyperlipidemia. Hyperlipidemia often results from dietary and lifestyle choices, e.g., eating a high fat diet or smoking. The causes of dyslipidemia can also be genetic or secondary. Primary causes of dyslipidemia include single or multiple gene mutations that lead to the overproduction of triglycerides and LDL cholesterol or the underproduction or excessive clearance of HDL cholesterol. Dyslipidemia in adults is commonly associated with a sedentary lifestyle coupled with excessive intake of saturated fat, cholesterol, and trans-isomer fatty acids. Dyslipidemia can be secondary to other disorders including diabetes mellitus, metabolic syndrome, hypothyroidism, overuse of alcohol, and chronic kidney disease. Dyslipidemias, in particular hypdercholesterolemia, have been linked to coronary heart disease and the formation of atherosclerotic plaques inside blood vessel walls, causing them to thicken and narrow and increasing the risk of heart disease, stroke, and heart attack. Treatment of dyslipidemia focuses primarily on reducing high levels of LDL cholesterol and secondarily on treating high levels of triglycerides, low levels of HDL cholesterol, or causative disorders such as diabetes or metabolic syndrome.

Metabolic syndrome refers to a syndrome characterized by the presence of at least three factors from an established group of traits, and marked by an association between a metabolic disorder and cardiovascular disease. The factors considered diagnostic criteria for metabolic syndrome can include abdominal obesity (e.g., excessive adipose tissue in and around the abdomen), elevated serum triglycerides, decreased HDL cholesterol, elevated blood pressure, insulin resistance, and glucose intolerance. Other factors present can include prothrombotic state (e.g., high fibrinogen or plasminogen activator inhibitor-1 in the blood), and proinflammatory state (e.g., elevated C-reactive protein in the blood). See, e.g., Alberti, et al., *Circulation,* 120:1640-1645, 2009, which is incorporated herein by reference.

Device Including One or More Cooling Elements Applied to One or More Tissues

The device includes one or more cooling elements configured to be applied to one or more tissues of a vertebrate subject and a programmable controller configured to provide instructions to the one or more cooling elements. The one or more tissues can include, but are not limited to, a thermoresponsive tissue, e.g. a thermoreceptor-containing tissue. Thermoreceptor-containing tissue refers to tissue having sensory receptors responsive to warm or cold stimuli. Nerve endings of sensory neurons that respond preferentially to cooling are found in in the skin but also occur in in the cornea, tongue, bladder, gastric and respiratory tissues. Warm and cold thermoreceptors have also been identified in different vagal territories including the gastrointestinal tract and the upper and lower respiratory tract. Thermoreceptive mechanisms also exist in body core structures including the brain, spinal cord and abdomen, including in the abdominal viscera, and in or around the great veins in the upper abdomen and thorax. Thermoreceptors in the abdominal viscera signal via splanchnic and vagus nerve afferent fibers, and their responses to temperature changes are similar to those of cutaneous thermoreceptors. Responses in the core are not as rapid as in the skin, and are likely to be involved in maintaining thermoregulation of basal temperature and in extreme or internal changes. Responsiveness to external cooling of the skin is noted to varying degrees on the face, chest, abdomen, back, upper arm, forearm, back of the hand, palm, thigh, leg, dorsum of the foot, and sole of the foot. The most sensitive areas of skin appear to be on the face and chest while the skin of feet appears to be the least sensitive. See, e.g., Morrison & Nakamura, *Frontiers in Bioscience* 16, 74-104, 2011; Choi & Seol, *J. Physiol. Anthropol.,* 20: 375-377, 2001, each of which is incorporated herein by reference.

The device including the one or more cooling elements can be applied to thermoresponsive tissue in the central nervous system. Regions of the central nervous system that appear to contain thermoresponsive tissue include, but are not limited to, portions of the hypothalamus including the preoptic area, anterior hypothalamus, and posterior hypothalamus; other portions of the brain including midbrain, medulla, and cortex; and the spinal cord. See, e.g., Morrison & Nakamura, Frontiers in Bioscience 16, 74-104, 2011; Boulant & Dean, *Ann. Rev. Physiol.* 48: 639-654, 1986, Passlick-Deetjen & Beddenbender-Stoll, *Nephrol. Dial. Transplant.,* 20: 1784-1789, 2005, each of which is incorporated herein by reference. Activation of an implantable, closed-loop cooling system with a peristaltic pump and a thermoelectric cooling device has been described for cooling specific portions of the central nervous system. See, e.g., Osorio, et al., *Medicon* 2007, *IFMBE Proceedings,* 16: 911-914, 2007 which is incorporated herein by reference.

Thermoresponsive tissue can refer to tissue in the core of the subject's body. Thermoresponsive tissue in the core can include, but is not limited to, bladder, gastrointestinal tract, abdominal viscera, and deep veins. For example, intraluminal application of cold stimuli to the stomach and small intestines induces abdominal cold sensation and a reflex contraction of the stomach. A similar reflex reaction is observed when the inner bladder wall is exposed to cold stimuli. See, e.g., Rawson & Quick, *J. Physiol.* 222: 665-677, 1972; Villanova, et al., *J. Physiol.* 502: 215-222, 1997; Jiang, et al., *J. Physiol.,* 543: 211-220, 2002, each of which is incorporated herein by reference.

The device including the one or more cooling elements can be applied to one or more tissues that include nervous tissue, cutaneous tissue, core tissue, organ tissue, visceral tissue, respiratory tissue, gastric tissue, adipose tissue, blood vessels, muscle tissue, or combinations thereof. Tissues may include a thermoresponsive tissue, e.g., a thermoreceptor-containing tissue, or may be associated with a thermoresponsive tissue. Nervous tissue refers to components of both the peripheral and central nervous systems including, but not limited to, peripheral neurons, spinal cord, and brain. A cutaneous tissue refers to a tissue associated with the skin and can include, but is not limited to, dermal tissue such as epidermal, dermal, or subdermal tissue. A cutaneous tissue can include a blood vessel, for example a blood vessel that occurs in vascularized dermal tissue. A cutaneous tissue can include a nerve tissue, which can be, for example, a cutaneous nerve tissue, a nerve fiber or nerve tissue ending. Cutaneous tissue is a well-known site of thermoreceptor-containing sensory neurons. A core tissue refers to a tissue deep within a body portion and can include, but is not limited to, a visceral tissue; an organ such as a visceral organ, digestive organ, or cardiopulmonary organ; a musculoskeletal tissue; a central nervous tissue or brain tissue; or one or more lymph vessels or blood vessels, in particular a deep blood vessel. A central nervous tissue can include, for example, a spinal ganglion, afferent or efferent nerve of the spinal ganglion, or a vagal nerve. Core tissue can be located in the thorax, abdominal, pelvic, head, and/or limb regions, and can include, but is not limited to, brain, heart, liver, lung, stomach, intestine, urogenital tract, kidney, bladder, secretory organs, skeletal muscle, vasculature, lymph, adipose, and bone. Core tissue can further refer to digestive tissue, circulatory tissue, or one or more blood vessels or lymph vessels. A blood vessel can include one or more great blood vessels or large blood vessels, such as a saphenous vein or pulmonary vein. A core tissue or a cutaneous tissue can include a thermoresponsive tissue, for example a thermoreceptor-containing tissue.

Brown adipose refers to any of a number of depots of brown adipose tissue, including brown adipocytes and brown adipocyte precursors, in a subject. The brown adipose tissue may include or be associated with a thermoresponsive tissue, e.g., a thermoreceptor-containing tissue. In rodents, for example, brown adipose tissue is found in two large lobulated masses on the dorsal aspect of the thorax between the scapulae and to a lesser extent around the aorta and in the hilus of the kidney. Brown adipose tissue is found in human neonates and human adults in a number of locations including, but not limited to, supraclavicular, paravertebral, mediastinal, para-aortic, and suprarenal areas. See, e.g., Richard and Picard, *Frontiers in Bioscience* 16: 1233-1260, 2011; Nedergaard, et al., *Am. J. Physiol. Endocrinol. Metab.* 293: E444-E452, 2007; Cypess, et al., *N. Eng. J. Med.*, 360: 1509-1517, 2009; Virtanen, et al., *N. Eng. J. Med.*, 360: 1518-1525, 2009; and van Marken Lichtenbelt, et al., *N. Eng. J. Med.*, 360: 1500-1508, 2009, each of which is incorporated herein by reference.

Device Including One or More Cooling Elements

A device is described herein that includes one or more cooling elements and a programmable controller configured to provide instructions to the one or more cooling elements in response to information regarding one or more physiological conditions of the vertebrate subject. The device can be used for the treatment of a disorder. The device including the one or more cooling elements can be applied to one or more tissues of the vertebrate subject to modulate at least one activity of brown adipose tissue of the vertebrate subject. The one or more cooling elements can include, but are not limited to, one or more electrical cooling elements, one or more Peltier cooling elements, one or more chemical cooling elements. The one or more cooling elements can further include one or more heat pumps. The one or more cooling elements can include one or more nanoparticles, microparticles, paramagnetic particles, magnetic particles, or chemical core particles.

In an aspect, the device including the one or more cooling elements can be applied directly to the surface of the body, e.g., on the surface of a cutaneous tissue such as the skin. The one or more cooling elements can be applied to the skin associated with the face, chest, abdomen, back, upper arm, forearm, back of the hand, palm, thigh, leg, dorsum of the foot, sole of the foot, or other body structure. In an aspect, the one or more cooling elements can be inserted into or through a natural orifice of the subject, e.g. to access a core tissue. Examples of a natural orifice include, but are not limited to, the oral cavity, trachea, esophagus, nose, ear, urethra, anus and vagina. In an aspect, the one or more cooling elements can access a dermal, subcutaneous, or core tissue through one or more artificial openings. In an aspect, the one or more cooling elements are implantable, e.g. able to be implanted directly into or in close proximity to a thermoresponsive tissue or other tissue type. In an aspect, the one or more cooling elements are directly inserted into a blood or lymph vessel.

In an aspect, at least a portion of the one or more cooling elements are applied to a deep portion of the body, while another portion of the one or more cooling elements is routed to a shallow portion of the body. The cooling elements can cool the tissue by passive means or by active means, or a combination thereof. The cooling elements in the shallow portion of the body can be tentacles near a cutaneous surface, i.e., implanted just below the skin to enable heat transfer with the external ambient temperature. For example, a first portion of the one or more cooling elements can be implanted into the hypothalamus of the subject and a second portion of the cooling elements implanted just below the skin at the neckline. The two portions of the one or more cooling elements can form a continuous loop through which a cooling fluid flows to cool the thermoresponsive tissues, e.g., the tissue in the hypothalamus.

The one or more cooling elements can be configured to attain a temperature from approximately 4° C. to approximately 36° C., a temperature from approximately 12° C. to 20° C., or a temperature from approximately 16° C. or lower. In general, the one or more cooling elements applied to one or more tissues can be cooler than the actual temperature attained by the tissue. For example, the one or more cooling elements can be configured to cool one or more tissues to a temperature ranging from approximately below 37° C. to approximately above 4° C. The ability of a cooling element to cool a tissue to a specific temperature is dependent upon the specific temperature of the cooling element and the amount of time the tissue is exposed to the cooling element. While cooling specific tissues of the body with the one or more cooling elements, the temperature of the rest of the body is maintained at thermoneutral temperatures, e.g., by using clothing or coverings, including insulated or warmed clothing or coverings.

In an aspect, the one or more cooling elements of the device can include one or more electrical cooling elements. The one or more electrical cooling elements can include one or more of a thermoelectric module, a thermoelectric cooler, a solid-state heat pump, and/or a Peltier cooling element. In an aspect, the one or more cooling elements of the device can include one or more Peltier cooling elements. The Peltier cooling elements can range in size from about $1 \times 2$ mm$^2$ to about $60 \times 60$ mm$^2$ (from, e.g., TEC Microsystems GmbH, Berlin, Germany; Eureca Messtechnik GmbH, Koln, Germany). Smaller micro-Peltier coolers with sub-millimeter areas have also been described. See, e.g., Bottner, et al., *J Microelectromechanical Systems*, 13: 414-420, 2004, which is incorporated herein by reference. In an aspect, the cooling element can include an array of micro Peltier cooling elements. In an aspect, the one or more Peltier cooling elements can be configured for direct contact with the skin of a subject. See, e.g., U.S. Pat. No. 6,023,932, which is incorporated herein by reference. In an aspect, the one or more Peltier cooling elements can be incorporated into a garment or other object wherein the cold plate of the Peltier is in intimate thermal contact with the skin of the wearer. See, e.g., U.S. Pat. No. 4,470,263, which is incorporated herein by reference. The Peltier cooling element can further include a thermocouple fixed to the surface of the Peltier to measure the actual temperature of the skin or tissue to provide feedback control of the temperature of the thermode. See, e.g., Craig, et al., *J. Neurophysiol.*, 86: 1459-1480, 2001, which is incorporated herein by reference.

In an aspect, the one or more cooling elements of the device can include one or more heat pumps. One or more heat pumps can be configured to move heat from one location, e.g., the target tissue, to another location using mechanical work. One common type of heat pump works by exploiting the physical properties of an evaporating and condensing refrigerant. The refrigerant, in its gaseous state, can be pressurized and circulated through the system by a compressor. On the discharge side of the compressor, a hot and highly pressurized gas is cooled in a heat exchanger, i.e., a condenser, until it condenses into a high pressure, moderate temperature liquid. The condensed refrigerant then passes through a pressure-lowering device like an expansion valve or capillary tube to another heat exchanger where the refrigerant evaporates into a gas via heat absorption. The refrigerant then returns to the compressor and the cycle is repeated.

In an aspect, the one or more cooling elements of the device can include one or more chemical cooling elements. The one or more chemical cooling elements can include one or more chemical refrigerant, e.g., an evaporant. See. e.g., Fajardo et al., *J. Neuroscience* 28: 7863-7875, 2008, which is incorporated herein by reference. Common examples of chemical refrigerants include, but are not limited to, chlorofluorocarbons (e.g., trichlorofluoromethane, dichlorodifluoromethane, and 1,2-dichlorotetrafluoroethane), hydrochlorofluorocarbons (e.g., chlorodifluoromethane and 2,2-dichloro-1,1,1-trifluoroethane), hydrofluorocarbons (e.g., 1,1,1,2-tetrafluoroethane), hydrocarbons (e.g., butane and iso-butane). Other potential chemical refrigerants for use as chemical cooling elements include, but are not limited to, pentane, isopentane, diethyl ether, methyl formate, hydrogen, helium, ammonia, water, neon, nitrogen, oxygen, argon, carbon dioxide, chloroethylene, chloromethane, sulfur dioxide, ethane, propane, and pentafluoroethane. The one or more chemical cooling elements can include a chemical cooling agent able to directly cool the tissue, e.g., an agent containing menthol or icillin. The one or more chemical cooling elements can include an endothermal chemical reactant capable of an endothermic reaction, for example, wherein the endothermal chemical reactants are housed in a tubing.

In an aspect, the one or more cooling elements of the device can include one or more nanoparticles, microparticles, paramagnetic particles, magnetic particles, or chemical core particles. The chemical core particles can further include endothermal chemical reactants capable of an endothermic reaction.

In an endothermic reaction, energy must be absorbed in order for the reaction to proceed. The absorbed energy results in a decrease in the temperature of the reaction mixture. For example, the combination of citric acid solution with sodium bicarbonate results in an endothermic reaction and a decrease in temperature. Other examples include, but are not limited to, the combination of barium hydroxide octahydrate crystals with dry ammonium chloride, the combination of ammonium chloride with water, the combination of thionylchloride with colbalt sulfate heptahydrate, the combination of ammonium nitrate with water, the combination of potassium chloride with water, and the combination of ethanoic acid with sodium carbonate. The one or more endothermal chemical reactants can be configured for direct contact with the skin and/or core tissue. Alternatively, the one or more endothermal chemical reactants can be contained in a mixing chamber with at least one surface adapted for efficient heat transfer, e.g., a metal plate, the latter of which is in direct contact with the skin and/or core tissue.

In an aspect, the one or more cooling elements include one or more endothermic biodegradable particles. The one or more endothermic biodegradable particles can include one or more frozen particles composed of water. The frozen particles composed of water can include any of a number of ice forms including normal hexagonal crystalline ice, ice Ih, and other forms of ice generated at modified temperatures and/or pressures including, but not limited to, ice Ic, ice II, ice III, ice IV, ice V, ice VI, ice VII, ice VIII, ice IX, ice X, ice XI, ice XII, ice XIII, or ice XIV. The one or more endothermic biodegradable particles can further include one or more frozen particles composed of hydrogen oxide, helium, neon, krypton, argon, xenon, nitrogen, chlorine, bromine, oxygen, air, carbon dioxide, or a combination thereof. The one or more frozen particles can include one or more medicament configured for delivery to the skin and/or core tissue for treatment of a metabolic disorder. Methods for preparation and delivery of frozen particles have been described in U.S. patent application Ser. Nos. 12/290,664; 12/290,671; 12/586,076; 12/384,202; 12/383,264; 12/383,851; and 12/590,033, each of which is incorporated herein by reference. The one or more endothermic biodegradable particles can be configured for direct or indirect application to the skin and/or to a core tissue and are anticipated to temporarily cool the site while undergoing a phase transition, e.g., melting, in response to the temperature of the skin and/or core tissue. The one or more endothermic biodegradable particles can be configured for direct contact with the skin and/or core tissue. Alternatively, the one or more endothermic biodegradable particles can be contained in a reservoir with at least one surface adapted for efficient heat transfer, e.g., a metal plate, the latter of which is in direct contact with the skin and/or core tissue that include cold-sensitive thermoreceptors.

In an aspect, the one or more cooling elements include a flow system in which fluid circulates through a series of tubing or other channels in a closed cycle. The fluid in the flow system can include a liquid and/or a gas. The fluid can be cooled by one or more of an electrical cooling element, a Peltier cooling element, a heat sink, a chemical cooling element, a particulate cooling element, or combinations thereof. At least a portion of the tubing can be placed in direct contact with the skin or other body parts. For example, insertion of thermodes into the hypothalamus of rhesus monkey can then be connected to a perfusion manifold and a circulating water bath. See, e.g., Smiles, et al., *J. Appl. Physiol.*, 40: 653-657, 1976, which is incorporated herein by reference. The fluid circulates through the tubing from a cooling element, e.g., a refrigeration system using a chlorofluorocarbon and/or a Peltier cooling element, to the tissue and back to the cooling element. The flow system can include a pump configured to pump the fluid through the flow system. The one or more cooling elements including a flow system can be incorporated into clothing, e.g., undergarment, vest, jacket, hat, body suit, or wrap, and/or into furniture, e.g., a bed and/or chair. See, e.g., U.S. Patent Applications 2009/0312676; 2008/0077211; 2008/0033518; 2009/0308082, each of which is incorporated herein by reference. In an aspect, the one or more cooling elements including a flow system can be incorporated into bedding including, but not limited to, pillows, sheets, blankets, or combinations thereof.

In an aspect, the one or more cooling elements can include a system for passive cooling or active cooling using a heat sink. In general, a heat sink is a term for a component that efficiently transfers heat from one place to another, in this case transferring heat associated with a fluid away from the fluid to facilitate cooling of the fluid. A passive heat sink dissipates heat through natural convection or macroscopic movement of heated molecules from a hot region to a cool region. For example, a fluid warmed by interaction with the internal temperature of a subject, e.g., 37° C., will lose heat as it passes from the internal space to an external space and is exposed to ambient temperature. For example, a fluid warmed by contact with the torso of a subject will lose heat as it passes from space adjacent to the torso, e.g. under clothing, to an external space, e.g. outside of the clothing, and is exposed to ambient temperature. A heat sink can feature a series of metal tubes in contact with a metal plate. The tubes are configured to provide maximum surface exchange with the cooling metal plate. The heat sink can include a meso-channel design in which fluid flow in a single tube is divided into multiple smaller tubes and recollects into larger tube at the end of the metal plate system. Jokar, et al., *Heat Transfer Engineering*, 31:3-16, 2010, which is incorporated herein by reference. The heat sink can include microchannel heat exchangers for transferring heat through multiple flat fluid-filled tubes containing small channels while air travels perpendicular to the fluid flow. See, e.g., Lee, et al., *Heat Mass Transfer*, 48: 1688-1704, 2005, Which is incorporated herein by reference. The heat sink can include a series of tubes, e.g., metal tubes, in contact with moving air such as a fan configured to move air past the series of metal tubes.

In an aspect, the one or more cooling elements can include a passive or active cooling system that includes one or more heat pipes. A heat pipe is a heat transfer system that combines thermal conductivity and phase transition to efficiently transfer heat between two interfaces. At the hot interface within a heat pipe, a liquid under vacuum in contact with a thermally conductive solid surface turns into a vapor by absorbing the latent heat of vaporization. The vapor flows through the system because of low pressure associated with the system and condenses back into a liquid at the cold interface, releasing the latent heat. For example, the one or more cooling elements can include one or more heat pipes which use a fluid that "boils" at body temperature, e.g., 37° C., but re-condenses at ambient temperature, e.g., 20-25° C. The liquid can return to the hot interface through either capillary action or gravity action where it vaporizes once more and repeats the cycle. The internal pressure of the heat pipe can be set or adjusted to facilitate the phase change. The heat pipe can consist of a sealed pipe or tube with hot and cold ends made of a material with high thermal conductivity such as, for example, copper, aluminum or titanium. The heat pipe can then be filled with a coolant or refrigerant under vacuum. Examples of such fluids include, but are not limited to, water, ethanol, acetone, sodium, or mercury.

The one or more heat pipes can further include a structure configured to exert capillary pressure on the liquid phase of the coolant or refrigerant. The structure can be sintered metal powder or a series of grooves, for examples, but in general may be any material capable of exerting capillary pressure on the condensed liquid to wick it back to the heated end. Alternatively, gravity or some other source of acceleration, e.g., provided by pressure and the mechanics of body movement, sufficient to overcome surface tension can be used to cause the condensed liquid to flow back to the heated end. In general, heat pipes contain no mechanical moving parts and typically require no maintenance.

The heat pipes for low temperature applications generally use some combination of ammonia (at −60° C. to 100° C.), alcohol (methanol at 10° C. to 130° C.; or ethanol at 0° C. to 130° C.), or water (at 30° C. to 200° C.) as working fluid. Other fluids or refrigerants can be used. Since the heat pipe contains a vacuum, the coolant can boil and take up latent heat at well below its boiling point at atmospheric pressure. For example, in an evacuated heat pipe, water will boil just slightly above its melting point (0° C.). The heat pipe will operate, therefore, when the hot end is just slightly warmer than the melting point of the working fluid. In an evacuated heat pipe, water will boil at just above 273° K (0° C.) and so can start to effectively transfer latent heat at this low temperature. One advantage of heat pipes over many other heat-dissipation mechanisms is their great efficiency in transferring heat.

The one or more cooling elements can further include one or more of nanoparticles, microparticles, paramagnetic particles, magnetic particles, chemical core particles, endothermic chemical particles, ice bullets, or combinations thereof. Nanoparticles, e.g., copper oxide, copper, and/or aluminum oxide particles (30 nm in diameter) suspended in a refrigerant, e.g., deionized water, ethylene glycol, or oil, to form a nanofluid increase cooling efficiency by providing better heat transfer. See, e.g., U.S. Pat. No. 6,221,275; Lee & Choi, "Application of metallic nanoparticle suspensions in advanced cooling systems," in *Recent Advances in Solids/ Structures and Application of Metallic Materials* International Mechanical Engineering Congress and Exposition, Atlanta, Ga., Nov. 17-22, 1996, each of which is incorporated herein by reference.

The one or more cooling elements can include one or more particles that are paramagnetic or magnetic particles. In general, magnetic cooling or magnetocaloric effect arises from exposing a magnetic material to a changing magnetic field. In an aspect, the cooling is facilitated by fluid suspensions containing magnetic and/or paramagnetic particles. See, e.g., Oesterreicher & Parker, *J. Appl. Phys.*, 55:4334-4338, 1984, and Gschneidner & Pecharsky, *Int. J. Refrigeration*, 31:945-961, 2008, each of which is incorporated herein by reference.

The one or more nanoparticles, microparticles, paramagnetic particles, magnetic particles, chemical core particles, endothermic chemical particles, ice bullets, or combinations thereof can be applied directly or indirectly to the surface of the skin or to an internal tissue. One or more particle types can be directly applied to the surface of the skin or to an internal tissue by release from a reservoir associated with the device. In an aspect, the device can be worn by the subject in the form of an undergarment that is in contact with one or more thermoreceptor-associated areas of the skin. In response to the programmable controller, the particles can be released from one or more reservoirs associated with the undergarment and brought into direct contact with the skin. In an aspect, the device can include a catheter for delivery of one or more particle types to one or more internal thermoreceptor-associated tissues or other internal target tissue. The catheter can be placed intravenously for direct access into a blood vessel; the catheter can be placed subcutaneously into a brown adipose depot; or the catheter can be placed intraperitoneally to access target tissues in the abdomen. In an aspect, the catheter for delivery of one or more particle types can be placed into a natural orifice of the subject, examples of which include, but are not limited to, oral cavity, nasal cavity, ear canal, urethra, vagina, or anus/colon.

In an aspect, the one or more nanoparticles, microparticles, paramagnetic particles, magnetic particles, chemical core particles, endothermic chemical particles, ice bullets, or combinations thereof can be applied indirectly to the surface of the skin or to an internal tissue. In this instance, the one or more particles types are contained in a compartment of the device wherein the compartment has direct contact with the skin or internal tissue. For example, the one or more particle types can be released into a compartment which includes a surface that readily transfers heat, e.g., a conducting metal surface, which is in direct contact with the skin and/or target tissue.

In an aspect, the one or more cooling elements can include one or more fluid-perfused patches. The one or more fluid-perfused patches may be configured to be applied to the surface of the skin. The patch size and number can vary depending upon the proportion of skin to be cooled. The one or more fluid-perfused patches can be applied directly to the surface of the skin, for example using an adhesive material. The one or more fluid-perfused patches can be associated with a garment worn by the subject so as to align the patches in contact with the skin and/or an underlying tissue. The one or more fluid-perfused patches can be associated with a structure that comes in direct contact with subject, e.g., bedding or a bed, a chair, or other piece of furniture, and aligns the patches in contact with the target tissue. The fluid-perfused patches and/or garment including the fluid-perfused patches can be under control of the programmable controller.

In an aspect, the one or more cooling elements can be part of a climate-controlled item of clothing, e.g., a fluid-perfusion suit. The fluid-perfusion suit can include one or more areas of controlled temperature output. The fluid-perfusion, suit can be worn to maintain core temperature at a set temperature while one or more cooling elements, for example one or more fluid-perfused patches, at one or more lower temperatures can be applied to specific tissue locations to induce non-shivering thermogenesis in brown adipose tissue. A climate-controlled item of clothing, e.g., a fluid-perfusion suit, can be configured to include an array of tubes incorporated into a long-sleeved jacket and/or full-length trousers and/or hood to enable transport of a cooling fluid to various parts of a body. The array of tubes can be connected to an external device configured to provide fluid, e.g., water at one or more temperatures, to the array of tubes, thereby maintaining the temperature in the item of clothing. The climate-controlled item of clothing can include a vest with cooling lines connected to an external refrigeration unit (from, e.g., Polar Products, Inc., Akron, Ohio). Alternatively, the climate-controlled item of clothing with cooling elements can be self-contained, for example utilizing one or more commercially available components such as those available from Allen Vanguard, Ashburn, Va. In general, the temperature and flow properties of the fluid within the fluid-perfused patches and/or climate controlled item of clothing and/or fluid-perfusion suit are under control of the programmable controller.

In an aspect, the one or more cooling elements can be part of a piece of furniture, a furniture covering, and/or a piece of bedding. The one or more cooling elements can be configured to include an array of tubes connected to an external device configured to provide fluid, e.g., water, at one or more temperatures to the tubes, thereby maintaining temperature to the furniture, furniture covering, or bedding. The one or more cooling elements can be self-contained.

In an aspect, the one or more cooling elements can include one or more cold packs. The one or more cold packs can be inserted into a piece of clothing, a piece of furniture, and/or a piece of bedding and be configured to apply a cooling temperature to one or more portions of the body, e.g., a portion of the skin or underlying tissues, to modulate activity of a brown adipose tissue, for example to induce non-shivering thermogenesis in brown adipose tissue. The device that includes a programmable controller can control flow of a cooling fluid past the cold packs in order to apply a cooling temperature to one or more portions of the body in response to information regarding one or more physiological conditions of the vertebrate subject. For example, the one or more cooling elements can include one or more cold packs inserted into cooling vests, hats, and/or wraps for neck, wrist, ankle, foot, and torso (from, e.g., Polar Products, Inc., Akron, Ohio). The one or more cold packs can include cold packs refrozen by placement into a refrigerator or freezer. The one or more cooling elements can include cold packs containing one or more endothermic chemical reactants. See, e.g., U.S. Pat. No. 3,977,202, which is incorporated herein by reference.

Device Including One or More Cooling Elements in Combination with One or More Neurostimulators Applied to One or More Tissues The device described herein including one or more cooling elements configured to be applied to one or more tissues of a vertebrate subject and a programmable controller configured to provide instructions to the one or more cooling elements in response to information regarding one or more physiological conditions of the vertebrate subject can further include a neurostimulator operating in combination with the one or more cooling elements. The neurostimulator can include but is not limited to an electric neurostimulator, optical neurostimulator, a magnetic neurostimulator, an ultrasonic neurostimulator, or a microwave neurostimulator. In an aspect, the device can include one or more neurostimulators configured to stimulate nerves involved in inducing thermogenesis in brown adipose tissue. For example, electrical stimulation of the ventromedial hypothalamic nucleus can induce thermogenesis in interscapular brown adipose tissue temperature, as measured by a 1 to 2° C. increase. See, e.g., Thornhill & Halvorson, *J. Physiol.* 426: 317-333, 1990, which is incorporated herein by reference. The one or more neurostimulator can be implanted into or adjacent to the central nervous system and be configured to stimulate neurons within a thermoregulatory pathway linking the nervous system to the brown adipose tissue. See e.g. Morrison & Nakamura, *Front Biosci.* 16: 74-104, 2011. Neurostimulation of one or more part of the brain can be used to directly or indirectly modulate the metabolic activity of brown adipose tissue, e.g. through a sympathetic pathway of the nervous system. Neurostimulation of specific nerves in the brain, e.g., hypothalamic nerves, are linked to localized release of catecholamines, e.g., norepinephrine, at the site of brown adipose tissue. The one or more neurostimulator probes can be placed in or near the hypothalamus, a region of the central nervous system previously shown to be linked to activation of brown adipose tissue. See, e.g., Morrison, et al., *Exp. Physiol.*, 93: 773-797, 2008, which is incorporated herein by reference.

In an aspect, a method for treating a disorder can include use of the device, as described herein, that includes one or more cooling elements configured to be applied to one or more tissues of a vertebrate subject and a programmable controller configured to provide instructions to the one or more cooling elements in response to information regarding one or more physiological conditions of the vertebrate, and further includes a neurostimulator for stimulating a nervous tissue. The neurostimulator used in the treatment method may be included in the device or may be a separate device. In an aspect, the device can include one or more neurostimulators configured to stimulate nerves other than those associated with modulating the metabolic activity of brown adipose tissue. For example, neurostimulation of the hypothalamus and/or vagus nerve can be used to curb appetite in subjects. See, e.g., U.S. Pat. Nos. 5,188,104; 5,263,480; 6,129,685, each of which is incorporated herein by reference. Neurostimulation of the vagus nerve can be combined with the one or more cooling elements to provide combined reduction in food intake and increased thermogenesis and heat loss to treat a disorder, e.g., a metabolic disorder such as obesity.

In an aspect, the device can include an electric neurostimulator combined with one or more cooling elements. The electric neurostimulator can be one or more of a pacemaker-like device which sends electrical impulses to specific neurons at specific intervals. The electric neurostimulator can be one or more of an implantable microstimulator such as those described in U.S. Patent Applications 2009/0157151 and 2009/0149917, each of which is incorporated herein by reference. The one or more electric neurostimulator can be one or more of an implantable Bion® microstimulator, a miniature, self-contained, rechargeable neurostimulator (from Advanced Bionics Corp., CA). The microstimulator can include one or more of a rechargeable battery, a radio and antenna for bi-directional telemetry, a programmable microchip, and a stimulating electrode. See, e.g., Carbunaru, et al., *Proc. 26$^{th}$ Annual International Conf. IEEE EMBS*, San Francisco, Calif., USA, Sept. 1-5, 2004, pp. 4193-4193, which is incorporated herein by reference. In an aspect, the neurostimulator can be one or more injectable neurotransponders, wherein each neurotransponder is the size of a grain of salt (about 1 mm in length and 0.25 mm in diameter) and can be linked together to form an array. See, e.g., U.S. Patent Application 2009/0198293, which is incorporated herein by reference. In general, the one or more electrical neurostimulators are in wireless communication with the device described herein. Examples of other commercially available neurostimulators include, but are not limited to, Synergy™ and Restore™ (from Medtronic, Minneapolis, Minn.), Eon Mini™ (from St. Jude Medical, Plano, Tex.), and Precision Plus™ (from Boston Scientific, Natick, Mass.).

In an aspect, the device including the one or more neurostimulators for use in combination with one or more cooling elements can further include one or more magnetic neurostimulators. For example, the magnetic neurostimulator can be in the form of transcranial magnetic stimulation in which a magnetic field is used to generate an electrical current in the brain. See, e.g., Wassermann, *Electroencephalogr. Clin. Neurophysiol.*, 108:1-16, 1998, which is incorporated herein by reference.

In an aspect, the device including the one or more neurostimulators for use in combination with one or more cooling elements can further include one or more ultrasonic neurostimulators. Ultrasonic neurostimulators are configured to deliver focused ultrasound, in pulsed or continuous waveforms to influence nerve activity through thermal and/or nonthermal (mechanical) mechanisms. The ultrasonic neurostimulator can deliver either low intensity ultrasound from about 30 to 500 mW/cm$^2$ and/or high-intensity focused ultrasound at power levels up to or exceeding 1000 W/cm$^2$. See, e.g., Tyler, *Neuroscientist*, 2010, e-print ahead of publication, which is incorporated herein by reference. In an aspect, focused ultrasound can be combined with a magnetic field to induce neurostimulation as described in U.S. Pat. No. 5,476,438, which is incorporated herein by reference.

In an aspect, the device including the one or more neurostimulators for use in combination with one or more cooling elements can further include one or more microwave neurostimulators. Focused microwaves at lower energies can provide sufficient thermal energy to trigger nerve stimulation. For example, microwave amplification through stimulated emission of radiation (maser) pulses can induce localized human deep brain stimulation, eliciting an action potential while increasing the baseline temperature. See, e.g, Pakhomov, et al., *Bioelectromagnetics*, 24: 174-181, 2003; U.S. Pat. No. 7,548,779; Sierra, *Current Sci.*, 98: 27-29, 2010, each of which is incorporated herein by reference.

In an aspect, the device including the one or more neurostimulators for use in combination with one or more cooling elements can further include one or more optical neurostimulators. The one or more optical neurostimulators can include a pulsed infrared-laser light that when applied to a nerve or nerves elicits an action potential. For example, pulsed, low-energy infrared with wavelengths ranging from 1.80 to 2.1 µm at a stimulation threshold of 0.3-0.4 J/cm$^2$ can elicit nerve action potentials and at a threshold that is several fold less than the threshold at which tissue damage occurs. See, e.g., Wells, et al., *SPIE Newsroom*, 10.1117/2.1200605.0233, 2006; Wells, et al., *Biophys J.*, 93: 2567-2580, 2007, each of which is incorporated herein by reference. Optical stimulation can also be combined with electrical stimulation to provide high spatial precision and greater energies without damaging radiant exposure. See, e.g., Duke, et al., *J. Biomedical Optics*, 14: 060501, 2009, which is incorporated herein by reference.

Device Including Programmable Controller in Communication with One or More Cooling Elements The device includes one or more cooling elements and a programmable controller operably connected to the one or more cooling elements, wherein the programmable controller is configured to provide instructions to the one or more cooling elements in response to information regarding one or more physiological conditions of the vertebrate subject. The programmable controller is configured to provide instructions to the one or more cooling elements in contact with one or more tissue in response to information regarding one or more physiological conditions of the vertebrate subject.

The programmable controller can be directed through a number of sources including, but not limited to pre-programmed information in the programmable controller regarding one or more physiological conditions of the subject, information provided by user input regarding one or more one or more physiological conditions of the subject, or programming provided by a digital processing unit regarding one or more physiological conditions of the subject.

The device further includes one or more sensors operably connected to the programmable controller, wherein the programmable controller is configured to provide instructions to the one or more cooling elements in response to information from the one or more sensors regarding one or more physiological conditions of the vertebrate subject. The one or more sensors can be configured to sense one or more one or more physiological conditions, or indicators thereof, of the vertebrate subject. For example, the programmable controller can be programmed so that if the skin temperature rises above 32° C., the programmable controller instructs the cooling elements to increase cooling but if the skin temperature falls below 24° C., it instructs the cooling elements to decrease cooling. A temperature of 32° C. represents an average thermoneutral skin temperature while 24° C. represents a skin temperature in the extremities following environmental cold exposure. In general, the cooling elements can be modulated by the programmable controller to keep the skin temperature between approximately 24° C. and 32° C. to induce non-shivering thermogenesis in brown adipose tissue of the human subject.

The device can further include a digital processing unit able to process information regarding the one or more physiological conditions into one or more resulting instructions and provide the instructions to the programmable controller. The digital processing unit can receive information regarding one or more physiological conditions of the subject from at least one of a sensor, a timekeeping device, a user interface, and an outside operating source. The digital processing unit can process that information into at least one resulting instruction, and can provide programming of the resulting information to the programmable controller.

The one or more physiological conditions include information regarding one or more analytes in the vertebrate subject including, but not limited to, a plasma level of one or more metabolic analytes, for example, blood glucose levels, blood fatty acid levels, blood pressure, heart rate, and cholesterol levels. For example, the device can include a blood glucose sensor operatively linked to the programmable controller, optionally through a digital processing unit, to sense the levels of glucose in the subject. The digital processing unit can also receive data regarding food consumed and can determine an estimate of calories ingested at specific times of the day and/or during the course of the day and provide programming to the programmable controller. Typically, the level of glucose measured in the blood will fluctuate depending upon when the measurement is taken relative to when the last meal was eaten.

The device including the digital processing unit operably connected to the programmable controller, wherein the digital processing unit can be programmable and can include memory such as volatile or non-volatile memory. The at least one digital processing unit can include processors such as microprocessors or digital signal processors, and computational entities such as operating systems, drivers, and applications programs. The at least one digital processing unit can be configured to receive information from at least one of a sensor, a timekeeping device, a user interface, or an outside operating source. The at least one digital processing unit can be configured to process the information into at least one resulting instruction and provide the at least one resulting instruction to the programmable controller. The at least one digital processing unit can be configured to implement logic such as comparison, sorting, reduction, and/or endpoint determination, e.g., relating to information regarding one or more physiological conditions of the vertebrate subject. The device can be configured with a digital processing unit configured to collect and analyze multiple data points in a relative fashion, including either serially or in parallel, e.g., relating to information regarding the one or more physiological conditions. The system can also include additional sensors, as described herein, and/or instruments such as a timekeeping device or clock.

In an aspect, the device including the programmable controller can further include the combination of the programmable controller and the one or more cooling elements as a single unit. For example, the programmable controller can be incorporated into a refrigeration unit that delivers cooling fluid in one or more tubes of the cooling element, which can be, for example, attached to the skin and/or implanted into an internal tissue of the subject. In another example, the programmable controller can be incorporated into a piece of clothing that also includes the one or more cooling elements.

In an aspect, the device includes a programmable controller wherein aspects of the programmable controller are physically separate from but in communication with the one or more cooling elements. For example, the one or more cooling elements of the device can be implanted into or proximal to an internal tissue of a subject, e.g., the hypothalamus, and receive instructions regarding control of the one or more cooling elements from an external programmable controller. The external programmable controller can be a computer work station or a handheld device that communicates, for example, wirelessly, with the one or more cooling elements implanted in the subject.

In an aspect, the device includes a programmable controller and one or more cooling elements that are integrated into an implantable single unit device. The implantable single unit device can function autonomously without input from an outside source, with the programmable controller controlling the function of the cooling elements based on input from one or more sensors. In this instance, one or more sensors can also be integrated into the implantable single unit device or can be placed in one or more locations remote from the implantable device and in wireless communication with the device. One or more digital processing units can also be integrated into the implantable single unit device or can be placed in one or more locations remote from the implantable device and be in wireless communication with the device. The one or more digital processing units can in communication with additional aspects of the device including sensors integrated with the device. The implantable single unit device, including any integrated digital processing units, can also be configured to receive information from an external or outside source, for example when changes need to be made to the device programming. Changes to the device programming can be made, for example, by the subject, a caregiver, and/or health care provider. The programmable controller or digital processing unit can communicate with other components of the device through a personal area network, for example, using a technology that permits communication over a short range, e.g., 5 to 10 meters using Bluetooth® wireless communication technology.

The one or more sensors configured to sense one or more physiological conditions of the vertebrate subject, or indications thereof, can be incorporated into a component of the device that includes one or more of the programmable controller, the digital processing unit, and the one or more cooling elements. For example, one or more sensors configured to measure a temperature of a tissue, e.g. a tissue to which one or more cooling elements is applied or a separate tissue, can be associated with the programmable controller that provide instructions to the one or more cooling elements, for example instructing the cooling elements to cool or not to cool one or more tissues of the subject. As another example, the one or more sensors configured to measure the activity level of a subject can be incorporated into a wrist watch-like accessory that also includes the programmable controller and a digital processing unit. In an aspect, the one or more sensor can be configured to come into direct contact with the surface of the skin and employ transdermal sensing of one or more analytes in the subject. For example, sensors included in the GlucoWatch® (from, Cyngus, Inc. Redwood City, Calif.) are configured to non-invasively and continuously monitor glucose using transdermal reverse iontophoresis. The digital processing unit receives data from the sensor and processes the data into at least one resulting instruction and provides the at least one resulting instruction to the programmable controller, which provides instructions to the one or more cooling elements. Alternatively or in addition, the one or more sensors providing information regarding one or more physiological conditions of the vertebrate subject, or indicators thereof, can be at one or more locations remote from the programmable controller and/or the one or more cooling elements. In this instance, data collected by the one or more sensors can be sent via wireless communication to the digital processing unit and/or programmable controller. For example, the one or more sensors can be one or more of an implanted sensing electrode or luminal pressure monitor configured to send data regarding heart rate or blood pressure to an externally located programmable controller. As another example, the one or more sensors can be one or more of an implantable sensor configured to monitor one or more analytes such as, for example, glucose. See, e.g., U.S. Pat. No. 6,001,067, which is incorporated herein by reference.

The device including the programmable controller can be configured to communicate with an outside operating source. The outside operating source can be configured to both transmit and receive data to and from the programmable controller or an associated digital processing unit. The outside operating source can be, for example, a computing device such as a personal computing device, smart phone, or personal digital assistant. The outside operating source can include access to a database having information regarding one or more analyte levels of normal subjects compared to subjects having a disease or disorder. The outside operating source can include database access having information regarding nonphysiologic information, such as caloric content of foodstuffs. The outside operating source can include a nonphysiologic sensor, for example an electronic food detector that can determine mass, volume, or weight of foodstuff to be eaten by the subject or can measure and quantitate caloric content and nutritional content of foodstuff that will be eaten by the subject. Data from the electronic food detector can be communicated to the digital processing unit or the programmable controller. See, e.g., U.S. Patent Application 2010/0125420;

2010/0125419; U.S. 2010/0125418; U.S. 2010/0125417; each of which is incorporated herein by reference. The outside operating source can include a user input device, a timekeeping device, or a human operator. The outside operating source can be carried by the subject, positioned in a room with the subject, and/or positioned in a location remote from the subject. The remote location can be a location outside the immediate location of the subject such as, for example, another room, down the hall, down the street, across town, across state, and/or across country. The remote location can include, but is not limited to, a caregiver's room, a nurse's station, a health care provider's office or clinic, a study site, and/or a health department. The outside operating source can further include a handheld device carried by another individual, e.g. a caregiver and/or health care provider. The programmable controller and/or digital processing unit are configured to both transmit and receive data to and from the outside operating source. The communication can be by wireless transmission, phone line, cable line, computer network, or other communication transmission line and/or wireless network. In an aspect, the outside operating source can be a computing device.

The device including the programmable controller can include one or more of a user interface for use by a subject, caregiver, and/or health care provider to interact with the device. The user interface can include one or more of a computing device with a display screen, e.g., a monitor or LCD screen, and a keyboard, keypad, or touchpad. The user interface can include one or more dedicated handheld device. The user interface can be incorporated into a multipurpose handheld device, e.g., a cell phone, a PDA, a handheld computer, or a wrist watch. The user interface can be used by a subject, a caregiver, a health care provider, or a combination thereof. The user interface can be used to input information, to receive information, or a combination thereof. Input information can include, for example, current weight, caloric intake, e.g., types of food consumed and quantity thereof, desired weight, desired rate of weight loss, for example, 1 to 2 pounds per week. The input information can include physiological conditions, or indicators thereof, that are measured using clinical assays independent of the device and can include, e.g. blood sugar levels, fatty acid levels, cholesterol levels, heart rate, blood pressure, other medical information pertinent to a metabolic disorder. For example, glucose readings from a standard glucose monitor or cholesterol levels measured during a clinical visit can be entered by the subject, caregiver, and/or health care provider using the user interface. The user interface can also be used to receive information. Examples of received information can include physiological conditions measured or sensed, e.g., metabolic analytes, blood glucose levels, fatty acid levels; internal temperature of brown adipose tissue associated with cold-induced thermogenesis; parameters associated with activity of brown adipose tissue, e.g. glucose accumulation, glycerol and fatty acid release, temperature, norepinephrine; calculated energy expenditure; calculated caloric intake; or net caloric intake.

The device including the programmable controller, which can include a digital processing unit, can include one or more time-keeping device, for example, a clock. A clock can be configured to provide the time of day, time of month, and/or time of year in a given global location. The time of day is relevant to the metabolic rate of the subject. For example, the metabolic rate of nocturnal animals is greater at night than during the day, while the metabolic rate of diurnal animals is greater during the day than at night. For example, day and night rhythms and the circadian clock have been linked with metabolism and with lipogenic and adipogenic pathways, which has implications for metabolic syndrome and obesity. See, e.g., O. Froy, *Endocrine Reviews* 31: 1-24, 2009, which is incorporated herein by reference. As such, the function of the one or more cooling elements can be adjusted to take into consideration the anticipated metabolic rate at different times during a 24 hour period. The time of month is relevant to the metabolic rate of, for example, female subjects during the menstrual cycle. For example, basal metabolic rate decreases at menstruation and falls to its lowest point approximately 1 week before ovulation and subsequently rises until the beginning of the next menstrual cycle. See, e.g., Solomon, et al., *Am. J. Clin. Nutr.*, 36: 611-616, 1982, which is incorporated herein by reference. A clock can be configured to provide elapsed time relative to an event, e.g., food consumption, oscillatory glucose and insulin levels in the blood, exercise or other activity.

The device including the programmable controller can further include programming, which may be in a digital processing unit, designed to optimize function of the one or more cooling elements, for example, to induce weight loss or treat a disorder. The programming includes computer software or other computing algorithms able to integrate information regarding, for example, caloric intake, energy expenditure, and activity of brown adipose tissue to determine the appropriate amount of cooling needed to induce thermogenesis sufficient for weight loss and/or treatment. In general, weight loss is facilitated when the energy expenditure of the subject exceeds the energy input, e.g., caloric intake, of the subject. Energy expenditure over the course of a 24 hour period, for example, includes resting or basal metabolic rate, i.e., the amount of energy required to maintain normal bodily functions at rest; energy expended during activity, e.g., walking or other exercise; and energy dissipated by thermogenesis in response to controlled cooling of tissue. Programming to induce weight loss takes into consideration these various parameters and compares them with the caloric intake over a similar period and modulates the cooling elements accordingly to increase or decrease thermogenesis to modulate the energy expenditure portion of the calculation. The programming also considers the current weight of the subject, the desired weight of the subject, and the desired rate of weight loss over a given time.

The device including the programmable controller can further include programming, which may be in digital processing unit, designed to take into consideration the basal and resting metabolic rate of the subject as part of optimizing the function of the one or more cooling elements to induce weight loss and/or treatment of a disorder. Basal metabolic rate is the minimum number of calories needed to sustain life in a fasting, resting individual. Basal metabolic rate can be measured experimentally in humans, for example, as the heat output from the body per unit time and/or by measuring the rate of oxygen consumption. Measurements are taken 12 to 14 hours after the last meal, completely at rest (but not asleep) and at an environmental temperature of 26-30° C., to ensure thermal neutrality. Measurement of metabolic rate under less rigorously controlled conditions can be used to determine the resting metabolic rate. For individuals with a sedentary lifestyle and relatively low physical activity, basal metabolic rate accounts for about 70-80% of total energy expenditure. The parameters of gender, height, weight, age, temperature, muscular activity, ventilation capacity, caloric intake, drugs, hormones and emotional state for use in determining basal and/or resting metabolic rate can be entered into the programmable controller using the user interface. See, e.g., Lyznicki, et al., *Am. Fam. Physician,* 63: 2185-2196, 2001, which is incorporated herein by reference.

The device including the programmable controller can further include a digital processing unit with programming designed to compare the information regarding one or more analytes, e.g. metabolic analytes, such as, for example, levels determined by sensors and provided to the digital processing unit. The digital processing unit with programming can be designed to compare the information regarding analyte levels at a given time with previous measurements or with acceptable norms. When the digital processing unit determines that the sensed levels of the one or more analytes are outside the acceptable norms, the digital processing unit provides resulting instructions to the programmable controller that is configured to take corrective action by providing instruction to the cooling elements to apply cooling to skin or other tissue site, for example to modulate at least one activity of brown adipose tissue, e.g. inducing non-shivering thermogenesis. For example, normal fasting blood glucose levels measured 8-12 hours following a meal range from about 70 to 100 mg/dL. A normal blood glucose level 2 hours postprandial in a non-diabetic individual is less than 180 mg/dL while the postprandial blood glucose levels in a poorly controlled diabetic will be higher, depending upon how much carbohydrate has been consumed, how much insulin the subject is producing, and how responsive the subject's insulin is to the carbohydrate consumed. See, e.g., American Diabetes Association, *Diabetes Care,* 33: S11-S61, 2010, which is incorporated herein by reference. The digital processing unit can be programmed to process the data and provide resulting instructions to the programmable controller. The programmable controller then provides instructions to the cooling elements to adjust the cooling, for example to increase cooling to induce non-shivering thermogenesis and thereby lower glucose levels to approach a near normal value.

Other analytes and other indicators of physiological conditions in the subject can be sensed by the sensors and analyzed by the digital processing unit, which processes the information into at least one resulting instruction and provides the resulting instruction to the programmable controller. The programmable control can provide instructions to the one or more cooling elements in response to information regarding one or more physiological conditions of the vertebrate subject. For example, triglycerides can also be analyzed in a tissue or fluid of the subject. A level of triglycerides of less than 150 mg/dL is considered normal, 150 to 199 mg/dL is borderline high, 200-499 mg/dL is high and 500 mg/dL and above is very high. Similarly, high blood pressure is defined as systolic pressure≥140 mm Hg and/or diastolic pressure≥90 mm Hg. In general, the digital processing unit is configured to receive data regarding one or more physiological condition, to process the information, for example by comparing the data with previous data or normal values, into at least one resulting instruction. The digital processing unit provides the at least one resulting instruction to the programmable controller to adjust the one or more cooling elements accordingly in order to modulate at least one activity of brown adipose tissue, for example to induce thermogenesis, and treat a disorder.

In an aspect, the programmable controller and/or digital processing unit can be located external to the body of the subject. The programmable controller can be located in the same unit with the one or more cooling elements. For example, the programmable controller and the one or more cooling elements can be incorporated into clothing, e.g., hat, vest, wrap, body suit, pants, shirt; bedding, e.g., pillow, sheet, blanket, mattress pad; furniture, e.g., bed, chair; or other stationary or ambulatory object unit. Alternatively, the programmable controller can be a located in a separate unit relative to one or more external and/or internal cooling elements. For example, the programmable controller can be incorporated into a computing device, e.g., a desktop or laptop computer; a dedicated handheld device; a multipurpose handheld device, e.g., a cell phone, a PDA, a handheld computer; or other accessory, e.g., a wrist watch-like accessory; in addition to clothing, bedding, furniture, or other object. In an aspect, the external programmable controller and the one or more external and/or internal cooling elements communicate via a wired connection. In an aspect, the external programmable controller and one or more external and/or internal cooling elements communicate wirelessly, e.g., via Bluetooth® wireless communication, radio frequency, or other wireless communication modality.

In an aspect, the programmable controller can be in an internal location in the body of a subject. The programmable controller can be located in the same implantable unit with the one or more cooling elements in contact with thermoresponsive tissue. For example, the programmable controller and one or more cooling elements can be implanted within or proximal to at least one lumen of a subject, e.g., at least one circulatory vessel, or the colon or large intestine. Alternatively, the programmable controller can be implanted at a location distant from the one or more implanted cooling elements. For example, the programmable controller may be implanted near the surface of the skin while the one or more cooling elements are implanted in or near a deep core tissue. The implanted programmable controller can be in either wired or wireless communication with the implanted one or more cooling elements. In an aspect, the implanted programmable controller can further include one or more transceiver for sending and receiving data from an external or outside source.

Device Including One or More Sensors in Communication with Programmable Controller and a Digital Processing Unit Other components of the device can include at least one digital processing unit operably connected to a programmable controller. A digital processing unit operably connected to a programmable controller can be configured to receive at least one signal from one or more sensors, including information regarding one or more physiological conditions of a vertebrate subject. The digital processing unit can be programmable and can include memory. The at least one digital processing unit can be configured to implement logic such as comparison, sorting, reduction, and/or endpoint determination. The digital processing unit can be configured to collect and analyze multiple data points in a relative fashion, including either serially or in parallel. The digital processing unit can be operably connected to the programmable controller and can be configured to receive information from at least one of a sensor, a timekeeping device, a user interface, and an outside operating source. The digital processing unit can process the information from the one or more sensors into at least one resulting instruction and providing the at least one resulting instruction to the programmable controller.

The programmable controller can be directed through a number of sources including, but not limited to, pre-programmed information in the programmable controller regarding one or more physiological conditions of the subject; information provided by user input regarding one or more one or more physiological conditions of the subject; or programming provided by the digital processing unit regarding one or more physiological conditions of the subject.

The programmable controller can be configured to receive at least one signal from the one or more sensors and to provide instructions in the form of at least one signal to the one or more cooling elements. The digital processing units can be configured to receive at least one signal from the one or more sensors and to process the signal into one or more resulting instructions and provide the instructions in the form of at least one signal to the programmable controller. The programmable controller can be configured to receive at least one signal from the one or more digital processing units and to provide instructions in the form of at least one signal to the one or more cooling elements. A signal can include, for example, an optic signal, a light signal, a chromatic signal, an acoustic signal, a vibrational signal, an infrared (IR) signal, an electronic signal, a digital signal, a radio signal, a wireless signal, or any other detectable signal. A signal from the one or more sensors, digital processing unit, or programmable controller can be part of the communication between the one or more sensors, the programmable controller, the digital processing unit, and/or the one or more cooling elements. For example, the programmable controller, the digital processing unit, or the one or more sensors can be configured with one or more transmitter and/or one or more receiver and can utilize for communication transmissions such as radiowaves. For example, the one or more sensor may include a means for transmitting radiofrequency signals and may include, e.g., an analyte sensor-enabled RFID tag (see., e.g., in Moore, *J. Diabetes Sci. Technol.* 3: 180-183, 2009, which is incorporated herein by reference). Miniaturized (0.5×0.5×5 mm) Implantable sensors are produced by BIORASIS Inc. including the GLUCOWIZZARD™, an implantable sensor that senses glucose levels and transmits the information to a proximal communicator. A syringe-implantable bio-sensor chip can be used that includes a passive transponder, glucose sensor and integrated circuitry. See, e.g., U.S. Pat. No. 7,125,382 to Zhou entitled "Embedded Bio-sensor System," which is incorporated herein by reference. See, e.g., Digital Angel Corporation, St. Paul, Minn. Transmission communications may include frequency-hopping spread spectrum technology such as Bluetooth® wireless technology. The acoustic transmission communication may include frequency-hopping spread spectrum technology such as Bluetooth® wireless technology.

The device including one or more signals from the one or more sensors can be part of the communication between the sensors and the digital processing unit or the programmable controller. A signal from the programmable controller can be part of the communication between the programmable controller and the one or more cooling elements. For example, where the one or more sensors are configured to emit an electromagnetic signal following detection of a physiological condition of the subject, the programmable controller can include an EM signal detection device, such as a detection device configured to detect non-visible light or light of a specific wavelength. See, for example, U.S. Patent Application No. 2003/0143580 to Straus, titled "Rapid and sensitive detection of molecules," which is incorporated herein by reference. In embodiments in which the one or more sensors are configured to emit optically detectable signals, the one or more sensors can include, in part or in whole, an optically permeable section (e.g. a window), and the one or more sensors or the programmable controller can include, in part, a spectrophotometer and/or light source configured to elicit signals related to information regarding a physiological condition of the subject. For example, the one or more sensors can include at least one of a chromogen, fluorescent agent, luminescent agent, a quantum dot, or a compound configured to exhibit alterable optical density. A light source associated with the one or more sensors can include, for example, a light emitting diode or a white light source, such as a source configured to provide light in a variable and/or specific wavelength, including infrared (IR) or ultraviolet (UV). See, for example, U.S. Pat. No. 5,183,740 to Ligler et al., titled "Flow immunosensor method and apparatus," U.S. Pat. No. 7,459,713 to Coates, titled "Integrated handheld sensing system approach for handheld spectral measurements having a disposable sample handling apparatus," U.S. Patent Application No. 2008/0265146 to Coates, titled "Integrated sensing module for handheld spectral measurements," which are herein incorporated by reference. For example, a sensor pair consisting of light emitter and light detector can be configured to be a part of the one or more sensors. The digital processing unit sensor can include a digital signal processor and/or software for converting the light signal into information able to be stored or communicated between the digital processing unit, programmable controller, and sensors. See, for example: U.S. Pat. No. 6,623,698 to Kuo, titled "Saliva-monitoring biosensor head toothbrush;" U.S. Pat. No. 7,314,453 to Kuo, titled "Handheld diagnostic device with renewable biosensor;" U.S. Patent Application No. 2003/0023189 to Kuo, titled "Handheld diagnostic device with renewable biosensor;" and U.S. Patent Application No. 2002/0127143 to Kuo, titled "Saliva-monitoring biosensor electrical toothbrush," which are herein incorporated by reference. In some embodiments, the one or more sensors can use electric pulses to measure the conductivity of one or more tissues of the subject to measure a physiological condition of the subject, e.g., pH, $pCO_2$, blood flow, blood pressure, skin temperature, core temperature, tissue temperature, or blood oxygenation. See, for example, U.S. Pat. Nos. 6,623,698 and 7,314,453 to Kuo.

The device including digital processing unit or programmable controller can include at least one communication unit including a telecommunication device, a display screen, a speaker, or a printer. For example, the programmable controller can be operable connected to at least one reporting device. The programmable controller, optionally in combination with the digital processing unit, can be operably connected to at least one reporting device, for example a visual display configured to indicate when a physiological condition in the subject has been detected.

The device including the programmable controller or the digital processing unit can include digital memory. For example, the programmable controller or the digital processing unit can include digital memory, e.g., random access, flash, read only, etc., that is configured to record received signals or sent signals, that is information regarding one or more physiological conditions of the subject, e.g., detected substances, time, temperature or pH associated with the detection, or other data. For example, the digital processing unit can include digital memory that is configured to include a medical history of the subject. For example, the digital processing unit can include digital memory that is configured to include medical information, such as information associating the one or more physiological conditions detected in the subject with a medical status.

The device including the programmable controller or the digital processing unit can be operably connected to a telecommunication device, which can include an antenna or a cable to transmit and receive information from a network or external computer device, such as a healthcare system computing device or an individual user's cell phone or personal data organizer (PDA). See, for example, U.S. Patent Application No. 2004/0078219 to Kaylor et al., titled "Healthcare networks with biosensors;" U.S. Patent Application No. 2004/0100376 to Lye et al., titled "Healthcare monitoring system;" and Lempert, "Digital house calls? Check your health at home," MSNBC Feb. 21, 2006; which are incorporated herein by reference. The programmable controller can also include additional elements or instrumentation as appropriate to a specific embodiment.

The device including the digital processing unit or the programmable controller can be configured to communicate with at least one network. The network can be a medical network, such as one that includes at least one medical history, for example a medical history of an individual user, or of a reference individual or group related to one or more physiological conditions of the subject. The medical history can include, for example, genetic or genomic information, drug use history, allergies, medical diagnoses, or surgical history. A network can be a public health response network. For example, the digital processing unit including the programmable controller can send and receive information from a local health department, such as to report infectious disease or environmental conditions that may affect one or more physiological conditions in the subject. Information stored on a network or within the digital processing unit can be accessed at a later time, for example, if there is a delayed response by the subject regarding the physiological condition or if there is a later report by another individual.

The device including the digital processing unit or the programmable controller can include a telecommunication device, such as a telecommunication device configured to communicate with a network, such as an area, localized, and/or centralized network. A network can include one or more database, including, but not limited to, one or more medical history, including for example, genetic or genomic information, drug use history, allergies, medical diagnoses, or surgical history. The programmable controller and/or digital processing unit can be configured as a portion of a network, which might include as a conductive medium part or all of the body. See, for example, U.S. Pat. No. 6,754,472 to Williams et al., titled "Method and apparatus for transmitting power and data using the human body," which is incorporated herein by reference. The programmable controller can be configured as a portion of a network that is integrated with part or all of a building, such as in a domotic, for instance the MavHome under study at the University of Texas at Arlington. The digital processing unit, and the programmable controller, or sensor can form, in part, a personal area network (PAN).

The programmable controller or the digital processing unit can be incorporated into another device, such as an individual user's cell phone, PDA, or laptop. An external device can be configured to communicate with the programmable controller or the digital processing unit or one or more sensors that measure the one or more physiological conditions of the subject.

The device including the programmable controller or the digital processing unit can include at least one communication device, such as a reporting device like a display screen, a speaker, or a printer and can be configured for interaction with a system user through a user interface such as a keyboard interface. For example, a communication device can be configured to accept queries or directions from at least one system user, such as an individual person or a computational, network, or robotic user.

The programmable controller can comprise multiple modules, for instance a handheld module configured to communicate with a separate component. The programmable controller can be configured as a size able to be held by a human hand, and can be configured to be in communication with the one or more sensors. In some embodiments the programmable controller can be configured to be wearable by a user, such as on an arm, waist, or back, and can be incorporated into a watch, armband, belt, waistpack, lumbar pack, or backpack. In some embodiments, the programmable controller, the digital processing unit and/or the one or more sensors can be configured to communicate through a wireless connection, such as radio frequency (RF) or other signals.

Device Including One or More Sensors in Communication with Programmable Controller The device including one or more cooling elements configured to be applied to one or more tissues of a vertebrate subject to modulate at least one activity of brown adipose tissue of the vertebrate subject, and a programmable controller configured to provide instructions to the one or more cooling elements in response to information regarding one or more physiological conditions of the vertebrate subject can further include one or more sensors operably connected to the programmable controller and configured to sense one or more indicator of the one or more physiological conditions. The one or more sensors can be operably connected to the programmable controller through a digital processing unit. The digital processing unit can be operably connected to the programmable controller and can be configured to receive information from the sensor, to process the information into at least one resulting instruction, and to provide the at least one resulting instruction to the programmable controller. The programmable controller is configured to provide instructions to the one or more cooling elements in response to information from the one or more sensors regarding one or more physiological conditions of the vertebrate subject. The one or more indicator of the one or more physiological conditions can include a plasma and/or localized tissue level of one or more analytes, e.g. a metabolic analyte, in the subject. In an aspect, the one or more analytes can include analytes associated with a disorder. In an aspect, the one or more metabolic analytes can include metabolic analytes associated with a metabolic disorder. The one or more metabolic analytes indicative of a metabolic disorder include, but are not limited to, glucose, free fatty acids, triglycerides, insulin, glucagon, pro-inflammatory molecules, cholesterol, low density lipoprotein (LDL), and high-density lipoprotein (HDL).

The one or more sensors are configured to provide data to the digital processing unit and/or the programmable controller regarding the plasma and/or tissue levels of analytes associated with a disorder. The programmable controller is configured to respond to the data received from the sensors by adjusting the one or more cooling elements to appropriately modulate the activity of brown adipose tissue in order to treat a disorder. Alternatively or in addition, the digital processing unit is configured to process the data from the sensor and provide instructions and/or programming to the programmable controller to adjust the one or more cooling elements to appropriately modulate the activity of brown adipose tissue to treat a disorder.

In an aspect, the one or more analytes can include analytes that can be indicative of brown adipose tissue activity. Such analytes include, but are not limited to, utilizable glucose, produced and/or released glycerol, free fatty acids, cAMP (indicative of beta-adrenergic receptor stimulation), hexokinase and phosphofructokinase or their enzymatic activities or products. For example, glucose accumulates in brown adipose tissue activated by exposure to cold. See, e.g., Cypess, et al., *N. Eng. J. Med.*, 360: 1509-1517, 2009; Virtanen, et al., *N Eng. J. Med.*, 360: 1518-1525, 2009, each of which is incorporated herein by reference. Similarly, the rate of glycerol and free fatty acid release from brown adipose tissue increases in response to cold acclimation as does the enzymatic activity of hexokinase and phosphofructokinase. See, e.g., Rabi, et al., *J. Appl. Physiol.*, 43: 1007-1011, 1977, which is incorporated herein by reference.

In an aspect, the one or more analytes can include a neurotransmitter. The level of norepinephrine increases in brown adipose tissue in response to cold exposure. See, e.g., Gabaldon, et al., *Am. J. Physiol. Regulatory Integrative Comp. Physiol.* 285: 91-98, 2003, which is incorporated herein by reference.

In an aspect, the one or more sensors configured to sense one or more physiological conditions, or indicators thereof, of the subject. The one or more physiological conditions can include heat generated by thermogenic activity of the brown adipose tissue. The one or more analytes can further include an analyte associated with thermogenic activity of the brown adipose tissue. To measure one or more analytes or other physiological condition associated with brown adipose tissue activity, the one or more sensors associated with the device are placed into or proximal to a depot of brown adipose tissue. The one or more sensors can be configured to provide data to the programmable controller or digital processing unit regarding analytes associated with the activity of the brown adipose tissue, for example, measurement of the activity of uncoupling protein 1 (UCP-1). UCP1, a protein specifically expressed in brown adipose tissue, provides an indication of basal and inducible energy expenditure in the form of thermogenesis (i.e., heat production) in brown adipose tissue. The digital processing unit can be configured to process the information and data received from the sensors into at least one resulting instruction and provide the at least one resulting instruction to the programmable controller. The programmable controller can be configured to provide instructions to the one or more cooling elements to alter function appropriately, e.g., by increasing or decreasing cooling of the tissue, so as to modulate the activity of the brown adipose tissue.

The device can include one or more sensors configured to sense one or more other physiological conditions of the subject including, but not limited to, pH, $pCO_2$, blood flow, blood pressure, skin temperature, core temperature, tissue temperature, or blood oxygenation. The one or more sensors can also be configured to sense measures of physical activity of the subject as a means for estimating daily energy expenditure. Measures of physical activity of a subject include, but are not limited to, body temperature, heart rate, skin resistance, motion/acceleration, and velocity.

The one or more sensors operably connected with the programmable controller can include, but are not limited to, one or more biosensors, chemical sensors, pressure sensors, temperature sensors, flow sensors, viscosity sensors, shear sensors (e.g., for measuring the effective shear modulus of the fluid at a frequency or strain-rate), pH sensors, optical sensors (e.g., charged couple device (CCD) array), optical waveguide sensors, acoustic sensors, surface acoustic wave sensors, quartz microbalance sensors, metal oxide sensors, bulk acoustic wave sensors, plate acoustic wave sensors, electrical sensors, magnetic sensors, interdigitated microelectrode sensors, electrochemical sensors, electrically conducting sensors, artificial noses, electronic noses, electronic tongues, semiconductive gas sensors, mass spectrometers, near infrared and infrared spectrometers, ultraviolet sensors, visible light-based sensors, fluorescence spectrophotometers, conductive-polymers, gas-fluorescence spectrophotometers, impedance spectrometers, aptamer-based biosensors, ion mobility spectrometry, photo-ionization detectors, amplifying fluorescent polymer sensors, ion mobility spectrometry, electrical impedance, microgravimetric sensors, cantilever and microcantilever sensors, accelerometers, global positioning devices, clocks or time-keeping devices. See, e.g., U.S. Pat. Nos. 5,522,394; 5,873,835; 6,409,674; 6,111,520; 6,278,379; 6,475,639; 6,802,811; 6,855,115, 6,517,482; 6,675,030; 6,836,678; 6,954,662; 7,184,810; 7,299,080, and U.S. Patent Application 2005/0277839, each of which is incorporated herein by reference.

For example, sensors can include a transdermal glucose monitor worn on the wrist. (GlucoWatch® glucose monitor, Cygnus, Inc. Redwood City, Calif.). The GlucoWatch® glucose monitor is configured to non-invasively and continuously monitor glucose using transdermal reverse iontophoresis. After calibration of glucose levels, the glucose monitor begins monitoring glucose. Batteries produce a small electrical current that draws fluid transdermally into the device. Electrode sensors measure the glucose in the fluid. The GlucoWatch® glucose monitor contains a built-in alarm that can be programmed to alert the user when results fall above or below pre-set levels.

The one or more sensors can include a single sensor or an array of sensors, and is not limited to a particular number or type of sensors. The one or more sensors can be very small, comprising a sensor or array of sensors, having, for example, a biosensor, a chemical sensor (Snow *Science*, 2005, 307: 1942-1945), a gas sensor (Hagleitner et al., *Nature*, 2001 414: 293-296), an electronic nose, a nuclear magnetic resonance imager (Yusa et al., *Nature*, 2005, 343: 1001-1005). The foregoing references are each incorporated herein by reference. Further examples of sensors are provided in *The Biomedical Engineering Handbook*, Second Edition, Volume I, J. D. Bronzino, Ed., Copyright 2000, CRC Press LLC, pp. V-1-51-9; Morrison et al., "Clinical Applications of Micro- and Nanoscale Biosensors" in *Biomedical Nanostructures*. Edited by K. E. Gonsalves, C. L. Laurencin, C. R. Halberstadt, L. S. Nair. 2008, John Wiley & Sons, Inc.; and U.S. Pat. No. 6,802,811, each of which is incorporated herein by reference.

The one or more sensors can be configured to detect an analyte that includes, but is not limited to, a biological marker, an antibody, an antigen, a peptide, a polypeptide, a neuropeptide, a protein, a complex, an enzyme, a hormone, a neurotransmitter, a nucleic acid, a cell (and, in some cases, a cell of a particular type, e.g. by methods used in flow cytometry), a cell fragment, a cellular component, a platelet, an organelle, a gamete, a pathogen, a lipid, a lipoprotein, an alcohol, an acid, an ion, an immunomodulator, a sterol, a carbohydrate, a saccharide, a polysaccharide, a glycoprotein, a metal, an electrolyte, a metabolite, an organic compound, an organophosphate, a drug, a therapeutic, a gas, a pollutant, or a tag. The one or more sensors can include one or more binding elements configured to interact with an analyte including, but not limited to, binding molecules, recognition elements, antibodies or fragments thereof, oligonucleotide or peptide based aptamers (see, e.g., Mok & Li *Sensors* 8: 7050-7084, 2008, which is incorporated herein by reference), receptors or ligands, artificial binding substrates (e.g. those formed by molecular imprinting), or any other examples of molecules and/or substrates capable of interacting with an analyte.

In an aspect, the device including the one or more sensors can include one or more optical sensors. An optical sensor can be configured to measure the optical absorption, optical emission, fluorescence, or phosphorescence, luminescence of an analyte or an associated tag or binding element, or of the brown adipose tissue, other tissues of interest, or combinations thereof. Such optical properties can be inherent optical properties of the analyte, e.g. autofluorescence, or can be optical properties of materials added or introduced into the body of the subject that interact with the analyte, the brown adipose tissue, other tissues of interest, or combinations thereof. Optical sensing of materials in blood, for example, is described in Mattley et al., "Blood characterization using UV/VIS spectroscopy" *Proc. SPIE Advances in Fluorescence Sensing Technology II*, Joseph R. Lakowicz; Ed. Vol. 2388, p. 462-470, 1995 and U.S. Pat. Nos. 5,589,932 and 7,027,134, each of which is incorporated herein by reference.

In an aspect, the one or more sensors can be configured to sense the accumulation of glucose in metabolically active brown adipose tissue. In this instance, a fluorescent analogue of glucose can be administered systemically, e.g. by the subject or health care provider or by the device under the control of the programmable controller, and accumulation of fluorescence measured in the brown adipose tissue depots. An example of a fluorescent analogue of glucose is 2-NBDG (2-[N-(7-nitrobenz-2-oxa-1,3-diazol-4-yl)amino]-2-deoxy-D-glucose) as described in Itoh, et al., *J. Cereb. Blood Flow Metab.* 24: 993-1003, 2004 (commercially available from Molecular Probes, Invitrogen, Carlsbad Calif.). Accumulated fluorescence associated with a fluorescently labeled glucose derivative, for example, can be detected in vivo in a subject using an implantable one-chip complementary metal-oxide semiconductor (CMOS). See, e.g., Tamura, et al., *J. Neurosci. Methods*, 173: 114-120, 2008, which is incorporated herein by reference. Uptake of glucose in metabolically active brown adipose tissue can also be measured using radiolabeled glucose, e.g., fluorodeoxyglucose ($^{18}$F-FDG), wherein the sensors are configured to detect the uptake of the radiolabeled glucose. See, e.g., Virtanen, et al., *N Engl. J. Med.* 360:1218-1525, 2009, which is incorporated herein by reference.

The device including the one or more sensors can include one or more sensors configured to sense the blood glucose levels in the subject. The one or more sensors can include a glucose sensor that is either an integral part of the device, wherein the sensors is operably connected to the programmable controller as described herein, or is in a separate device, for example a glucose sensing device in wireless communication with the programmable controller in the device described herein. A number of different glucose monitors have been described using, for example, pin prick, transdermal, or implantable devices. See, e.g., U.S. Pat. Nos. 4,436,094; 4,953,552; 5,497,772; U.S. Patent Applications 2010/0049021; 2010/0081910; each of which is incorporated herein by reference. The one or more sensors can include one or more electrochemical- or photochemical-based sensors wherein a measureable chemical reaction occurs in response to the presence of one or more analyte: For example, many electrochemical sensors use enzymes as specifiers for the analyte. The enzymes cause a chemical reaction, such as a reduction reaction, and electrons released by the reaction are transferred to a mediator molecule, which itself is converted. The mediator then transfers the electrons to an electrode for electrochemical measurement or transfers the electrons to an indicator molecule for photochemical responses. Ferrocene derivatives and hexacyanoferrate are examples of one-electron mediators. Quinones are an example of two-electron mediators. A glucose sensor included in the device uses as the specifier an oxidoreductase that oxidizes glucose to gluconolactone. Electrons from the glucose are then transferred to the oxidized form of a mediator molecule, which in turn delivers the electrons to an electrode. The amount of electric current generated is proportional to the amount of glucose in the sample, and electronics within the sensor convert the signal, and the signal is communicated to the programmable controller or the digital processing unit that is operably connected to the programmable controller. See, e.g., Hones, et al., *Diabetes Techn &Therap*, 10: Supplement 1 S10-S26, 2008. Examples of commercially available glucose monitors using such technology in measuring blood glucose levels of a subject include, but are not limited to, OneTouch® blood glucose monitors (LifeScan-Johnson & Johnson, Milpitas, Calif.), Accu-Chek® blood glucose monitors (F. Hoffman-Roche AG, Basel, Switzerland), and Ascencia® blood glucose monitors (Bayer HealthCare LLC, Tarrytown, N.Y.). In an aspect, the glucose sensor for measuring blood glucose levels of a subject can include a continuous monitoring system, examples of which include, but are not limited to Freestyle Navigator® glucose monitor (Abbot Diabetes Care, Alameda, Calif.), Guardian® Real-Time glucose monitor (Medtronic MiniMed, Northridge, Calif.), and DexCom™ SEVEN® glucose monitor (DexCom, San Diego, Calif.). See, e.g., Hermanides & DeVries, *Diabetologia*, 53: 593-596, 2010, which is incorporated herein by reference. The FreeStyle Navigator® glucose monitor, for example, is biocompatible chip implanted into the abdomen or back of the upper arm of a subject and includes an external receiver. Similarly, blood glucose sensor-enabled radio frequency identification (RFID) devices have been described for active monitoring of glucose. See, e.g., Moore, *J. Diabetes Sci. Technol.* 3: 180-183, 2009, which is incorporated herein by reference. Miniaturized (0.5×0.5×5 mm) implantable glucose sensors can include the GLUCOWIZZARD™ implantable glucose sensor that senses glucose levels and transmits the information to a proximal communicator. See, e.g., BIORASIS Inc., Storrs/Mansfield, Conn. A syringe-implantable biosensor chip can include a passive transponder, glucose sensor, and integrated circuitry. See, e.g., U.S. Pat. No. 7,125,382 to Zhou entitled "Embedded Bio-sensor System," which is incorporated herein by reference. See, e.g., Digital Angel Corporation, St. Paul, Minn. Other methods for continuous monitoring of blood glucose levels of a subject include transcutaneous fluorescence lifetime-based microsensors or subcutaneous microelectromechanical systems (MEMS)-based sensors. See, e.g., U.S. Pat. No. 6,304,766; Nielsen, et al., *J. Diabetes Sci. Technol.* 3: 98-109; Li, et al., *J. Diabetes Sci. Technol.* 2: 1066-1074, 2008, each of which is incorporated herein by reference.

In an aspect, the one or more sensors can use a charged coupled device (CCD) or complementary metal-oxide-semiconductor (CMOS) sensor, for example, in combination with a binding element that exhibits altered optical properties, e.g., fluorescence, in response to binding an analyte. For example, glycerol and/or free fatty acids can be analyzed using one or more of the sensors. A sensor for measuring a free fatty acid can include an acyl-CoA-binding protein which exhibits an increased fluorescence yield in response to binding a fatty acid. See, e.g., Wadum, et al., *Biochem. J.*, 365: 165-172, 2002, which is incorporated herein by reference.

In an aspect, the one or more sensor can include a binding element, e.g., an antibody or oligonucleotide aptamer, configured to exhibit Förster or fluorescence resonance energy transfer (FRET) in response to binding one or more analytes in the subject. FRET is a distance-dependent interaction between the excited states of two fluorophore molecules in which excitation is transferred from a donor molecule to an acceptor molecule without emission of a photon. For use in a sensor, one or more binding molecules, e.g., antibodies or oligonucleotide aptamers, associated with the one or more sensors are configured with at least one donor molecule and at least one acceptor molecule. The interaction of an analyte with the binding molecule of the sensor results in a conformation change in the binding molecule, leading to changes in the distance between the donor and acceptor molecules and changes in measurable fluorescence.

Donor and acceptor fluorophore pairs can be considered for FRET including, but not limited to, fluorescein and tetramethylrhodamine; IAEDANS and fluorescein; fluorescein and fluorescein; and BODIPY FL and BODIPY FL, and various Alexa Fluor pairings as described herein. The cyanine dyes Cy3, Cy5, Cy5.5 and Cy7, which emit in the red and far red wavelength range (>550 nm) as well as semiconductor quantum dots can also be used for FRET-based detection systems. Quenching dyes can also be used to quench the fluorescence of visible light-excited fluorophores, examples of which include DABCYL, the non-fluorescing diarylrhodamine derivative dyes QSY 7, QSY 9 and QSY 21 (Molecular Probes, Carlsbad, Calif., USA), the non-fluorescing Black Hole Quenchers BHQ0, BHQ1, BHQ2, and BHQ3 (Biosearch Technologies, Inc., Novato, Calif., USA) and Eclipse (Applera Corp., Norwalk, Conn., USA). A variety of donor fluorophore and quencher pairs can be considered for FRET associated with the binding molecule including, but not limited to, fluorescein with DABCYL; EDANS with DABCYL; or fluorescein with QSY 7 and QSY 9. In general, QSY 7 and QSY 9 dyes efficiently quench the fluorescence emission of donor dyes including blue-fluorescent coumarins, green- or orange-fluorescent dyes, and conjugates of the Texas Red and Alexa Fluor 594 dyes. QSY 21 dye efficiently quenches all red-fluorescent dyes. A number of the Alexa Fluor (AF) fluorophores (Molecular Probes-Invitrogen, Carlsbad, Calif., USA) can be paired with quenching molecules as follows: AF 350 with QSY 35 or DABCYL; AF 488 with QSY 35, DABCYL, QSY7 or QSY9; AF 546 with QSY 35, DABCYL, QSY7 or QSY9; AF 555 with QSY7 or QSY9; AF 568 with QSY7, QSY9 or QSY21; AF 594 with QSY21; and AF 647 with QSY 21.

The one or more sensors for sensing one or more physiological conditions of a subject can include surface plasmon resonance (for planar surfaces) or localized surface plasmon resonance (for nanoparticles). Surface plasmon resonance involves detecting changes in the refractive index on a sensor surface in response to changes in molecules bound to the sensor surface. In an aspect, the surface of the sensor is a solid support coated with a thin film of metal, e.g., gold. The one or more sensors include a matrix to which is immobilized one or more binding molecules, e.g., antibodies or aptamers, that recognize one or more analytes. The sensor is illuminated by monochromatic light. Resonance occurs at a specific angle of incident light. The resonance angle depends on the refractive index in the vicinity of the surface, which is dependent upon the concentration of analyte bound to the surface. See, e.g., Raghavan & Bjorkman Structure 3: 331-333, 1995, which is incorporated herein by reference.

The one or more sensors for sensing analytes can be one or more label-free optical biosensors that incorporate other optical methodologies, e.g., interferometers, waveguides, fiber gratings, ring resonators, and photonic crystals. See, e.g., Fan, et al., Anal. Chim. Acta 620: 8-26, 2008, which is incorporated herein by reference. The light-based signal or electrical signal to the sensor is converted by a transducer, e.g., within the digital processing unit, into within the digital processing unit, which then processes the data into information that can be stored, analyzed, and communicated, including, for example, at least one resulting instruction. The digital processing unit provides the at least one resulting instruction to the programmable controller.

The one or more sensors configured to provide information regarding one or more physiological conditions of the subject can include one or more microcantilevers. A microcantilever can act as a biological sensor by detecting changes in cantilever bending or vibrational frequency in response to binding of one or more analytes to the surface of the sensor. See, e.g., Lavrik et al., Rev. Sci. Inst, 75:4: 2229-2253, 2004, which is incorporated herein by reference. In an aspect, the sensor can include a microcantilever or a microbead as in an immunoaffinity binding array. In another aspect, a biochip can be formed that uses microcantilever bi-material, e.g., formed from gold and silicon, as sensing elements. See, e.g. Vashist J. Nanotech Online 3: DO: 10.2240/azojono0115, 2007, which is incorporated herein by reference. The gold component of the microcantilever can be coated with one or more binding molecules which upon binding one or more analytes causes the microcantilever to deflect. Aptamers or antibodies specific for one or more analytes can be used to coat microcantilevers. See, e.g., U.S. Pat. No. 7,097,662, which is incorporated herein by reference. The one or more sensors can incorporate one or more methods for microcantilever deflection detection including, but not limited to, piezoresistive deflection, optical deflection, capacitive deflection, interferometry deflection, optical diffraction grating deflection, and charge coupled device. The deflection is measured and transmitted as data by a transducer, e.g., within the digital processing unit, which then processes the data into information that can be stored, analyzed, and communicated, including, for example, at least one resulting instruction. The digital processing unit provides the at least one resulting instruction to the programmable controller. In some aspects, the one or more microcantilevers can be a nanocantilever with nanoscale components. The one or more microcantilevers and/or nanocantilevers can be arranged into arrays. Both microcantilevers and nanocantilevers can find utility in microelectomechnical systems (MEMS) and/or nanoelectomechnical systems (NEMS).

The one or more sensors for sensing analytes can include a field effect transistor (FET) based biosensor. In this aspect, interaction of one or more analytes with one or more binding elements of the sensor induces an electrical change that is detected by the transistor. See, e.g., U.S. Pat. No. 7,303,875, which is incorporated herein by reference. The signal is processed by the digital processing unit into at least one resulting instruction. The digital processing unit provides the at least one resulting instruction to the programmable controller.

The one or more sensors for sensing one or more analytes can incorporate electrochemical impedance spectroscopy. Electrochemical impedance spectroscopy can be used to measure impedance across a natural and/or artificial lipid bilayer. The sensor can incorporate an artificial bilayer that is tethered to the surface of a solid electrode. One or more receptor can be embedded into the lipid bilayer. The one or more receptors can be ion channels that open and close in response to binding of a specific analyte. The open and closed states can be quantitatively measured as changes in impedance across the lipid bilayer. The changes in impedance measured and transmitted as data by a transducer. See, e.g., Yang, et al., IEEE SENSORS 2006, EXCO, Daegu, Korea/Oct. 22-25, 2006, which is incorporated herein by reference. The signal is processed by the digital processing unit into at least one resulting instruction. The digital processing unit provides the at least one resulting instruction to the programmable controller.

The one or more sensors can include cells with binding molecules that induce a measurable or detectable change in the cells, e.g., a luminescent signal, when bound to analytes. For example, one can use a bioluminescent bioreporter integrated circuit in which binding of an analyte to an engineered cell induces expression of a reporter polypeptide linked to a luminescent response. See, e.g., U.S. Pat. No. 6,673,596; Durick & Negulescu Biosens. Bioelectron. 16: 587-592, 2001, each of which is incorporated herein by reference. Alternatively, the one or more cell can be engineered to emit an electrical signal in response to interacting with one or more analytes. In a further aspect, an implantable biosensor can include genetically modified cells that respond to binding analytes by emitting a measurable electrical signal in response to one or more intracellular second messenger molecules that in turn modulate the activity of one or more ion channels in the genetically modified cells. The genetically modified cells act as an implantable biosensor that can be coupled via an electrical or optical interface to digital processing unit that processes the signal into at least one resulting instruction and provides the at least one resulting instruction to a programmable controller. See U.S. Patent Application 2006/0234369 A1; which is incorporated herein by reference. In another aspect, a biosensor can include a microbial biosensor. For example, a microbial biosensor and an oxygen electrode can be used to sense free fatty acid. See, e.g., Schmidt, et al., *Biosensors Bioelectronics* 11: 1139-1145, 1996, which is incorporated herein by reference.

The one or more sensors can be configured to include an assembly for in vivo microdialysis. In vivo microdialysis allows for continuous sampling from the interstitial fluid of a tissue with minimal influence on surrounding tissues and/or whole body function. A microdialysis probe can be inserted into a tissue of interest, e.g., brown adipose tissue, and perfused at a constant flow rate with a physiological buffer, e.g., saline. The tip of the probe consists of a semi-permeable membrane through which compounds in the interstitial fluid of the tissue can diffuse and subsequently be sampled from the outlet tubing of the probe. For example, a linear, implantable microdialysis probe with outlet tubing for collection of analytes can be used to measure norepinephrine levels in brown adipose tissue in response to cold temperature exposure. See, e.g., Gabaldon, et al., *Am. J. Physiol. Regulatory Integrative Comp. Physiol.* 285: 91-98, 2003, which is incorporated herein by reference. This technique can also be used to assess lipolytic activity in adipose tissue by measuring glycerol and free fatty acids, the end-products of lypolysis. See, e.g., Flechtner-Mors, et al., *J. Pharm. Exp. Ther.,* 301: 229-233, 2002; Jensen, et al., *J. Pharm. Biomed. Anal.,* 43: 1751-1756, 2007, each of which is incorporated herein by reference.

The one or more sensors can include one or more temperature sensors configured to measure temperature in one or more tissues. For example, temperature sensors can be configured to measure heat generated as a result of thermogenesis in brown adipose tissue depots. The temperature sensor can be a thermistor, a thermocouple, or a resistive temperature detector. In an aspect, the temperature sensor is a probe thermometer inserted through the skin of the subject and into tissue, e.g., the brown adipose tissue, with wires extended out into the exterior of the subject to transmit internal temperature data to the external programmable controller. In an aspect, the temperature sensor is an implantable device that wirelessly transmits internal temperature data to an external programmable controller. An example of an implantable temperature sensor is described in U.S. Patent Application 2009/0012574, which is incorporated herein by reference. In an aspect, the temperature sensor is an integral component of a self-contained, fully implantable device.

The one or more temperature sensors can further include sensors configured to measure the skin and/or core temperature of the subject. Skin temperature can be measured, for example, using any of a number of patch-like temperature sensors (e.g., Level 1™ Skin Temperature Sensor, from Smiths Medical, Dublin, Ohio; VitalSense® Dermal Temperature, Philips—Respironics, Anover, Mass.). Non-invasive surrogate measurements of core temperature can be taken at a sublingual site, the axilla, and the tympanic membrane. Invasive measurements of core temperature can be taken using a rectal, esophagus, or gastrointestinal probe. For example, core temperature can be measured using an ingestible telemetric temperature pill (e.g., CorTemp®, from HQ, Inc., Saratoga, Fla.; VitalSense® Ingestible Capsule, from Philips—Respironics, Anover, Mass.). Temperature sensors can be quite small and integrated into the device. For example, the temperature sensors can include one or more semiconductor thermometers produced in the form of an integrated circuit, which are available commercially.

The one or more sensors can include one or more sensors that are calorimeters configured to measure caloric intake and/or energy expenditure. In an aspect, the one or more calorimeter can include an indirect calorimeter configured to assess the physical activity of the subject by periodically monitoring heart rate, body temperature, skin resistance, motion/acceleration sensing, velocity and providing an estimate of caloric intake/energy expenditure. The indirect calorimeter can include one or more of a temperature sensor, a heart rate sensor, an accelerometer, a global positioning system, or a combination thereof. See, e.g., U.S. Patent Application 2009/0240113, which is incorporated herein by reference. An example of a wireless patch system configured for estimating energy expenditure has been described and includes sensors, electrodes, and accelerometers. This system measures a variety of physiological conditions including temperature, heart rate, respiratory rate, and skin conductivity and uses this information in an algorithm to calculate the number of calories consumed, the number of calories burned, and the net yield. See, e.g., U.S. Patent Application 2010/0049004, which is incorporated herein by reference. Other examples of calorie counters based on activity measurements have been described. See, e.g., U.S. Pat. Nos. 4,100,401; 4,159,416; 5,815,954; and 7,334,472, each of which is incorporated herein by reference. Other means for performing calorimetry include, but are not limited to, the Haldane gravimetric method, open-circuit calorimeter with mask, spirographic method, assessment of heat loss and oxygen consumption.

In an aspect, a calorimeter can include a means for manually inputting data regarding caloric intake, wherein the food item and quantity eaten by a subject are entered into a software program and the number of calories estimated. See, e.g., U.S. Pat. Nos. 5,890,128; and 6,675,041, each of which is incorporated herein by reference. The software program for entering and estimating the caloric intake can be associated with the programmable controller of the device or with a digital processing unit of the device operably connected to the programmable controller. Alternatively, the software program can be contained in a separate device capable of communication with the programmable controller or digital processing unit of the device. For example, the software program can be part of a dedicated handheld device designed for electronic calorie counting or incorporated into another device such as, for example, a cell phone, a PDA, a portable laptop, or a wrist watch.

The one or more sensors of the device can be configured to send data regarding a physiological condition in the vertebrate subject to the programmable controller of the device or to a digital processing unit operably connected to the programmable controller. Conversely, the digital processing unit can be configured to instruct the one or more sensors to collect and transmit data or other information regarding one or more physiological conditions or indicators thereof at specified regular intervals and/or when triggered by sensed events or by initiation of particular device activity. The device may further include information storage. For example, measurement of one or more physiological condition may be collected and stored at specified times on a daily basis with an associated time stamp. More than one physiological condition may be measured simultaneously and associated with one another during processing. For example, measurement of localized brown adipose tissue temperature, or a localized temperature of an associated nerve tissue or circulatory tissue, can be assessed at the same time as measurement of blood glucose levels. A temperature measurement can also be triggered by other sensor activity such as when a measured exertion level reaches a specified limit value or immediately following caloric intake.

Device Including One or More Cooling Elements in Combination with One or More Medicaments and Method for Use in Treating a Disorder The device can be used in a method for treating a disorder in a vertebrate subject. The method can include applying cooling to one or more tissues of the vertebrate subject with one or more cooling elements, wherein the one or more cooling elements are configured to lower the temperature of the one or more tissues and thereby modulate at least one activity of the brown adipose tissue of the vertebrate subject, and controlling the one or more cooling elements with a programmable controller configured to provide instructions to the one or more cooling elements in response to information regarding one or more physiological conditions of the vertebrate subject. The method can further include providing one or more medicaments in combination with applying the device configured to cool one or more tissues for the treatment of a disorder, weight loss, metabolic disorder, diabetes, obesity, metabolic syndrome, or dyslipidemia. The one or more medicaments can be one or more agents able to modulate (e.g. initiate, induce, enhance, inhibit, or suppress) at least one activity of brown adipose tissue, such as thermogenesis or metabolic activity. The one or more medicaments can be one or more agents able to modulate at least one activity of brown adipose tissue, such as a recruitment, proliferation, differentiation, or adipogenesis. The one or more medicaments can be one or more agents able to modulate at least one activity of brown adipose tissue can be a neurostimulant. The one or more medicaments can be one or more agents able to modulate at least one activity of brown adipose tissue and can include, but are not limited to, a β-adrenergic receptor agonist, NPY agonist, leptin, UCP activating agent, thyroxine, serotonin reuptake inhibitor, MCH agonist, GLP-1 agonist, 5-HT2C agonist, 5-HT2A agonist, galanin antagonist, CRF agonist, urocortin agonist, melanocortin agonist, enterostain agonist, and transcription factor, cAMP analog, bone morphogenetic protein or agonist thereof. Treatment of a vertebrate subject with medicaments that include natural or synthetic PPARγ ligands can result in recruiting brown adipocytes or inducing proliferation of brown adipocytes in tissues of the vertebrate subject. PRDM16 expression in myoblasts can induce differentiation of myoblasts into brown adipocytes. PRDM16 stimulates brown adipogenesis by binding to PPAR and activating PPAR transcriptional function. Treatment of a vertebrate subject with medicaments including bone morphogenetic protein 7 (BMP7) or analogs thereof has been shown to specifically direct brown adipocyte differentiation in the vertebrate subject. Treatment of a vertebrate subject with the device as described herein can include or be combined with one or more medicaments including, but not limited to, cAMP analogs, thyroid hormone, insulin, thiazolidinediones, or retinoic acid, or analogs thereof, that can induce UCP1 expression and induce thermogenesis in brown adipose tissue. See, e.g., Saely, et al., "Brown versus White Adipose Tissue: A Mini-Review," *Gerontology*, Karger A G, Basel, Dec. 7, 2010, which is incorporated herein by reference.

The method for treating a disorder in a vertebrate subject can further include providing the device as described herein in combination with one or more medicaments configured to treat a metabolic disorder. The medicaments can include one or more medicaments for the treatment of weight loss, obesity, diabetes, dyslipidemia, hypercholesterolemia and/or metabolic syndrome. Examples of medicaments used for weight loss and treatment of obesity include, but are not limited to, lipase inhibitors (e.g., orlistat), appetite suppressants (e.g., sibutramine, rimonabant, phendimetrazine, diethylpropion, phentermine, bupropio, topiramate, zonisamide), agents that delay gastric emptying (e.g., hormones and their analogs such as exenatide and pramlintide), and metformin. Examples of medicaments used for the treatment of diabetes include, but are not limited to, insulin, sulfonylurea secretagogues (e.g., tolbutamide, acetohexamide, tolazamide, chlorporpamide, glipizide, glyburide, glimepiride, gliclazide), meglitinide secretagogues (e.g., repaglinide, nateglinide), biguanide insulin sensitizers (e.g., metformin), thiazolidinediones (e.g., rosiglitazone, pioglitazone), alpha-glucosidase inhibitors (e.g., miglitol, acarbose), glucagon-like peptide analogs and agonists (e.g., exenatide, liraglutide, taspoglutide), dipeptidyl peptidase-4 inhibitors (e.g., vildagliptin, sitagliptin, saxagliptin), and amylin analogues (e.g., pramlintide). Examples of medicaments used for the treatment of dyslipidemia and hypercholesterolemia include, but are not limited to, statins (e.g., atorvastatin, fluvastatin, lovastatin, pitavastatin, pravastatin, rosuvastatin, simvastatin), cholesterol absorption inhibitors (e.g., ezetimibe), bile acid sequestrants (e.g., cholestyramine, colestipol), fibrates (e.g., fenofibrate, gemifibrozil), and niacin.

In general, medicaments used to treat obesity, diabetes, dyslipidemia, and hypercholesterolemia as described above are also of use in treating aspects of metabolic syndrome. Additional aspects of metabolic syndrome, e.g., hypertension, can be treated with anti-hypertensive medicaments. Examples of medicaments for use in treating hypertension include, but are not limited to, diuretics (e.g., chlorthalidone, hydrochlorothiazide, metolazone, spironolactone, bumetanide), beta blockers (e.g., acebutanol, metoprolol, propranolol, carteolol, timolol), ACE inhibitors (e.g., benazepril, captopril, enalapril, moexipril), angiotensin II receptor blockers (e.g., candesartan, eprosartan, irbesarten, losartin), calcium channel blockers (e.g., amlodipine, diltiazem, nifedipine, verapamil), alpha blockers (e.g., doxazoin, prazosin, terazosin), combined alpha and beta-blockers (e.g., carvedilol, labetolol), central agonists (e.g., alpha methyldopa, clonidine, guanabenz acetate), peripheral adrenergic inhibitors (e.g., resiprine, guanadrel), and vasodilators (e.g., hydralazine, minoxidil).

Device Including One or More Cooling Elements in Combination with Power Source

The device including the one or more cooling elements configured to be applied to one or more tissues of a vertebrate subject to modulate at least one activity of brown adipose tissue of the vertebrate subject, and a programmable controller configured to provide instructions to the one or more cooling elements in response to information regarding one or more physiological conditions of the vertebrate subject, can include at least one power source configured to power the components of the device. The device can further include one or more sensors and/or one or more neurostimulators. The power source can be one or more of a wired power source and/or one or more of a wireless power source. In an aspect, a wired power source for powering the device can be derived from a standard electrical outlet. For example, a standard electrical outlet can be used to power an external refrigeration unit that circulates cooling fluid to the skin or internal tissue as well as to power an associated programmable controller. A wireless power source includes stored power, a battery, or a fuel cell. For an implantable device, the power source can be external, internal, or a combination thereof. The implanted device can be coupled to an external power source through a radio-frequency link. Alternatively, the implanted device can include a self-contained power source made using any means of generation or storage of energy, e.g., a primary battery, a replenishable or rechargeable battery, a thin film battery, a capacitor, or a supercapacitor. A replenishable or rechargeable self-contained power source can be replenished or recharged using a radio-frequency link, an optical link, or other energy-coupling link. See, e.g., U.S. Patent Application No. 2005/0143787, by B. Boveja, which is incorporated herein by reference. In an aspect, the power source for an implantable device is supplied from an external power source via a transcutaneous inductive coupling. See, e.g., U.S. Patent Application 2010/0076524, which is incorporated herein by reference.

The power source can include electrical energy generated by mechanical energy of a subject's movement. For example, the power source can be a linear motion electric power generator that uses a rare earth magnet and a coil positioned to move linearly back and forth relative to one another. The movement of the coil in the field of the magnet generates a current in the coil. See, e.g., U.S. Pat. No. 5,347,186, which is incorporated herein by reference. In this instance, power can be generated as the device moves, e.g., bounces up and down while jogging or while doing other physical activity, as exemplified by the nPower® PEG (Personal Energy Generator, from Tremont Electric, Tremont, Ohio). In an aspect, the power source can be one or more solar panel attached to one or more component of the device such as, for example, a portable refrigeration unit in a backpack with affixed solar panels. See, e.g., U.S. Patent Application 2009/0015022 which is incorporated herein by reference.

In an aspect, the power source can include a rubber film configured to harness energy associated with natural body movements. For example, the power source can include a material made of a ceramic piezoelectric material, e.g., fabricated lead zirconate titanate that is embedded in silicone rubber sheets. The rubber film can harness natural body movements such as walking and breathing as electricity when flexed, converting approximately 80% of mechanical energy into electrical energy. See, e.g., Qi, et al., *Nano Lett.*, 10: 524-528, 2010, which is incorporated herein by reference.

The power source can include one or more of a battery or microbattery, a fuel cell or biofuel cell, or a nuclear battery. One or more power sources of the same or different types can be included in the device, without limitation. Batteries for a small implantable device can include a microbattery, e.g., as available from Quallion LLC, Sylmar, Calif. (http://www.quallion.com), or one designed as a film (U.S. Pat. Nos. 5,338,625 and 5,705,293), each of which is incorporated herein by reference. Alternatively, the power source could be one or more fuel cell, for example, a biofuel cell, such as an enzymatic, microbial, or photosynthetic fuel cell (US2003/0152823A1; W003/106966A2; or Chen T et al.," *J. Am. Chem. Soc.* 2001, 123: 8630-8631, each of which is incorporated herein by reference). The fuel cell can be of any size, including the micro- or nano-scale. In an aspect, the power source can include laterally packaged piezoelectric fine wires that convert biomechanical energy (e.g., stretching muscles, beating heart, walking) into electrical energy using a nanogenerator. See, e.g., Yang et al., *Nature Nanotechnol.*, 4: 34-39, 2009; Yang et al., *Nano Lett.*, 9: 1201-1205, 2009, each of which is incorporated herein by reference. In another aspect, the power source can include a pressure-rectifying mechanism that utilizes pulsatile changes in blood pressure or an acceleration-rectifying mechanism as used in self-winding watches, or other types of flow-rectifying mechanism capable of deriving energy from other flow parameters. In an embodiment, the power source can be a nuclear battery. See, e.g., Wacharasindhut et al., *Appl. Phys. Lett.* 2009, 95: 014103, which is incorporated herein by reference.

In an aspect, the power source can be located remote from the device and can include an electrical power source connected to the structural element by a wire, an optical power source connected to the structural element by a fiber-optic line or cable, or a power receiver capable of receiving power from an acoustic source or electromagnetic source (e.g., infrared energy, or inductively coupled, as described in U.S. Pat. Nos. 6,170,485, and 7,212,110; U.S. Patent Application No. 2005/0228259; and Budgett et al., *J. Appl. Physiol.* 2007, 102: 1658-1663, each of which is incorporated herein by reference). The power source can include power generated from thermoelectric heating based on the differential between body temperature of a subject and the ambient temperature. See, e.g., U.S. Pat. No. 6,075,199; U.S. Patent Application 2009/0056328, each of which is incorporated herein by reference. In an aspect, the device can include a power transmitter capable of transmitting power (e.g., acoustic power, electrical power, or optical power) from the device to a secondary location. The secondary location can be, for example, one or more cooling elements, one or more sensors, another device, or combinations thereof.

The vertebrate subject can include, but is not limited to, human, equine, bovine, ovine, swine, rodent, canine, feline, avian, amphibian, or reptile.

PROPHETIC EXAMPLES

Example 1

Device for Treating Obesity in a Human Subject Including External Cooling Elements in a Vest A device is described that includes cooling elements operating under a programmable controller for cooling an area of the body of a human subject to modulate an activity of brown adipose tissue for the purpose of treating obesity in the human subject. The device is incorporated into a vest worn by the subject and includes cooling elements in direct contact with thermoreceptors associated with the skin of the subject. The cooling elements have a temperature range from approximately 0° C. to approximately 37° C. to achieve skin temperatures ranging from approximately 24° C. to approximately 32° C. to induce non-shivering thermogenesis in brown adipose tissue of the subject. The device includes a programmable controller operationally linked to multiple skin temperature sensors to control the level of cooling based on sensing the skin temperature of the subject.

The device includes a vest with cooling elements that directly contact the skin on the chest of the subject. The vest is equipped with an array of tubes that circulate a cooling fluid. The cooling fluid, e.g., water, circulates in a closed circuit through the array of tubes and into and out of a refrigeration unit. The refrigeration unit is positioned on the back of the vest. The refrigeration unit includes an array of Peltier elements that cool the circulating water and a small fan that dissipates the heat generated by the Peltier elements. A method for circulating cooling water with an array of Peltier elements is described in U.S. Pat. No. 4,829,771, which is incorporated herein by reference. The water is pumped from the refrigeration unit through an input tube and then spreads out into an array of smaller diameter tubes incorporated into the front surface of the vest. The circulating water is re-collected into an output tube and re-circulated back into the refrigeration unit for re-cooling. The Peltier element for cooling the water and the pump for circulating the water are powered using a rechargeable battery pack.

In another vest configuration, water cooling is facilitated by long-lasting freezer inserts in the refrigeration unit placed into the back of the vest. The back of the vest is well insulated in order to prevent the freezer inserts from uncontrollably cooling the skin of the subject's back and to prolong the cooling capacity of the freezer inserts. The water in the closed loop is controllably pumped past the freezer inserts and circulated to the front of the vest to cool the skin on the subject's chest.

The temperature and flow rate of the water through the array of tubes in the vest is controlled by a programmable controller in a wired connection to sensors and to control cooling elements of the vest. The programmable controller includes a user interface for inputting and receiving data, and a keypad and display screen. The programmable controller can control the output from the refrigeration unit based on input from temperature sensors in contact with the surface of the skin on the chest of the subject. The temperature sensors can sense the skin temperature and transmit this information to the programmable controller. The skin temperature sensors are integrated into the vest and in a wired connection to the programmable controller. The skin temperature sensors are oriented in the vest so that the sensors contact the subject's skin at sites distinct from the sites of active cooling. The skin temperature sensors are adapted from skin temperature sensors used for monitoring neonatal temperatures (e.g., Neo-Therm® Skin Temperature Sensor, from Smiths Medical, Dublin, Ohio). The programmable controller has been programmed so that if the skin temperature rises above 32° C., it instructs the cooling elements to increase cooling but if the skin temperature falls below 24° C., it instructs the cooling elements to decrease cooling. A temperature of 32° C. represents an average thermoneutral skin temperature while 24° C. represents a skin temperature in the extremities following environmental cold exposure. In general, the cooling elements are modulated by the programmable controller to keep the skin temperature between approximately 24° C. and 32° C. to induce non-shivering thermogenesis in brown adipose tissue of the human subject. The programmable controller, cooling system and skin temperature sensors of the device are wired together in the vest and are powered by a rechargeable battery pack.

Example 2

Device for Treating Obesity in a Human Subject Including External Cooling Peltier Elements in a Vest A device is described that includes cooling elements operating under a programmable controller for cooling an area of the body of a human subject to modulate an activity of brown adipose tissue for the purpose of treating obesity in the human subject. The device is incorporated into a vest worn by the subject and includes a number of small Peltier elements incorporated directly into the vest and positioned such that the cold surface of the Peltier elements are in contact with the skin of the subject, and the hot surface of the Peltier elements dissipates heat to the ambient environment on the outside surface of the vest. The Peltier elements have a temperature range from approximately 0° C. to approximately 37° C. to achieve skin temperatures ranging from approximately 24° C. to approximately 32° C. and thereby induce non-shivering thermogenesis in brown adipose tissue of the subject. The device includes a programmable controller operationally linked to multiple skin temperature sensors to control the level of cooling based on sensing the skin temperature of the subject.

The Peltier elements are controlled by a programmable controller incorporated into the vest. The programmable controller includes an attached user interface for inputting and receiving data and a keypad and a display screen. The programmable controller can control the cooling output from Peltier elements based on input from temperature sensors placed on the surface of the skin on the chest of the subject. The temperature sensors are dermal temperature patches attached to the face of the vest adjacent to the skin at one or more locations on the subject's skin and in wireless communication with the programmable controller associated with the cooling vest (e.g., Dermal Temperature Patch, from Philips-Respironics, Andover, Mass.). The programmable controller has been programmed so that if the skin temperature rises above 32° C., it instructs the cooling elements to increase cooling but if the skin temperature falls below 24° C., it instructs the cooling elements to decrease cooling. A temperature of 32° C. represents an average thermoneutral skin temperature while 24° C. represents a skin temperature in the extremities following environmental cold exposure. In general, the Peltier elements are modulated by the programmable controller to keep the skin temperature between approximately 24° C. and 32° C. to induce non-shivering thermogenesis in brown adipose tissue of the human subject. The cooling system and the programmable controller are powered by mechanical energy generated by the movements of the subject using an nPower® Personal Energy Generator (from Tremont Electric, Tremont, Ohio) incorporated into the back of the vest.

Example 3

Device for Facilitating Weigh Loss in a Human Subject Including External Cooling Elements Contacting Facial Skin A device is described that includes cooling elements operating under a programmable controller for cooling an area of the body of a human subject to modulate an activity of brown adipose tissue brown adipose tissue to facilitate weight loss in the human subject. The device is incorporated into a sleeping surface, e.g., a pillow, and includes cooling elements in direct contact with facial skin of the subject and in contact with the thermoreceptors associated the facial skin. The cooling elements have a temperature range from approximately 0° C. to approximately 37° C. to achieve a range of tissue temperatures ranging from approximately 24° C. to approximately 32° C. to induce non-shivering thermogenesis in brown adipose tissue of the subject. The device includes a programmable controller and a digital processing unit operably connected to the programmable controller. The programmable controller controls the level of cooling according to instructions received from the digital processing unit based on caloric intake, physical activity, and the desired weight loss regimen. The programmable controller of the device is incorporated into a refrigeration unit used to control the cooling elements. The device includes sensors that monitor the caloric intake and physical activity of the subject. The sensors are associated with a wrist watch-like accessory worn by the subject during waking hours. Data collected by the wrist watch-like accessory are wirelessly transmitted to the digital processing unit programmable controller at the end of the waking day. The digital processing unit processes the data into at least one resulting instruction and provides the at least one resulting instruction to the programmable controller. See, e.g., FIG. 1.

The device includes a pillow that comes in direct contact with the facial skin of a subject. An array of flexible rubber tubing for circulating a cooling fluid is incorporated into one surface of the pillow. The cooling fluid, e.g., water, circulates in a closed circuit through the array of tubing in the pillow and into and out of a separate refrigeration unit. The refrigeration unit is positioned proximal to the sleeping surface and is a small, commercially available, portable refrigerator/freezer unit (from, e.g., Engel USA, Jupiter, Fla.). The refrigeration unit is powered using a standard electrical plug or, when a plug is not available, using a rechargeable battery. The cooling water is pumped from the refrigeration unit through input tubing to spread out into an array of smaller diameter tubing on the pillow surface. The cooling water is recollected into output tubing and re-circulated back into the refrigeration unit for re-cooling.

The temperature and flow rate of the fluid are controlled by a programmable controller integrated into the refrigeration unit. A digital processing unit operably connected to the programmable controller and associated with the refrigeration unit can estimate the amount of cooling needed to facilitate weight loss based on data received regarding measurements of caloric intake and input from physical activity sensors and temperature sensors. The estimate of the amount of cooling needed to facilitate weight loss is dependent upon the caloric intake and physical activity level of the subject, the amount of thermogenesis generated by cooling the facial skin, and the desired rate of weight loss, e.g., 1 to 2 pounds per week. In general, weight loss is expected to occur when the energy expenditure, e.g., activity level and thermogenesis, exceeds the energy consumed, e.g., caloric intake.

The device includes a digital processing unit operably connected to a programmable controller. The digital processing unit is configured to receive information from sensor and process the information into at least one resulting instruction and provide the at least one resulting instruction to the programmable controller. The digital processing unit may be programmable and may include memory and software. The digital processing unit includes at least one processor, such as a microprocessor or digital signal processor, and an applications program for calculating energy expenditure and energy consumption by the subject. The data processing unit may further calculate an effect of the physiological condition of the subject on the energy expenditure and energy consumption by the subject.

The digital processing unit receives data from a wrist watch-like accessory that collects data regarding caloric intake and physical activity of the subject during waking hours. The digital processing unit can also receive data from an outside operating source, for example a computing device, such as a personal computing device, smart phone, or personal digital assistant. The wrist watch-like accessory has a user interface for input of caloric intake. See, e.g., U.S. Pat. No. 6,675,041, which is incorporated herein by reference. The wrist watch-like accessory can include access to a database having information regarding one or more analyte levels of normal subjects compared to subjects having a disease or disorder. The wrist watch-like accessory can include or interface with a nonphysiologic sensor, for example, an electronic food detector that can determine mass, volume, or weight of foodstuff to be eaten by the subject and can measure and quantitate caloric content and nutritional content of foodstuff that will be eaten by the subject. Data from the electronic food detector can be communicated to the digital processing unit or the programmable controller. See, e.g., U.S. Patent Application 2010/0125420; 2010/0125419; U.S. 2010/0125418; U.S. 2010/0125417; each of which is incorporated herein by reference. The subject manually enters the type and estimated quantity of food consumed during the course of waking hours. The wrist watch-like accessory also collects data from physical activity sensors that sense the activity of the subject as measured by sensing heart rate, body temperature, skin resistance, motion/acceleration, and velocity of the subject. See, e.g., U.S. Pat. No. 4,312,358, which is incorporated herein by reference. The data from the physical activity sensors are transmitted to the digital processing unit which then processes the data to estimate the physical activity level of the subject as reported in calories burned. Data collected by the wrist watch-like accessory regarding food consumed and physical activity during the day are transmitted wirelessly to the digital processing unit at the end of the waking day prior to the subject falling asleep on the pillow that includes the cooling device. The digital processing unit includes a database of calorie counts for various foods and uses the input data from the wrist watch-like accessory to calculate the daily caloric intake. The digital processing unit processes the information and provides an instruction to the programmable controller, which then adjusts the cooling element to deliver the necessary cooling to the subject.

In some cases, the digital processing unit is also in wireless communication with thermosensors implanted under the skin and in close proximity to brown adipose depots in the supraclavicular region of the subject. The thermosensors can monitor the heat generated in the brown adipose tissue depots in response to facial skin cooling. Telemetric sensors for measuring body temperatures are available in various sizes from Data Sciences International (St. Paul, Minn.). The digital processing unit uses the data regarding caloric intake, calories burned, and heat generated in the brown adipose depot to estimate energy consumption. The programmable controller provides instructions to the refrigeration unit to increase or decrease the temperature and/or rate of flow of the water circulating through the pillow to appropriately modulate non-shivering thermogenesis in the brown adipose tissue that results in an increase or decrease energy consumption and facilitates weight loss in the subject.

Weight loss in the subject is monitored on a daily to weekly basis using a standard bathroom scale. The amount of weight lost is manually entered into the wrist watch-like accessory. Alternatively, the bathroom scale can be fitted with a wireless transmitter that automatically transmits information regarding weight to the wrist watch-like accessory, which in turn can be downloaded into the digital processing unit. Based on the rate of weight loss over the course of days and/or weeks as well as the daily caloric intake and physical activity data, the digital processing unit instructs the programmable controller to adjust the temperature and the flow rate of the cooling fluid circulating through the pillow. Once the desired weight has been reached, the device is programmed to provide a level of cooling designed to maintain the current desired weight.

Example 4

Device for Treating Diabetes in a Human Subject Including Internal Cooling Elements Contacting Visceral Tissue A device is described that includes cooling elements operating under a programmable controller for cooling an area of the body of a human subject to modulate an activity of brown adipose tissue and thereby to treat a disorder, e.g. metabolic disorder such as diabetes in the human subject. The device includes multiple internal cooling elements that are applied to thermoresponsive tissue in an internal abdominal area to modulate an activity of a brown adipose tissue of the human subject, for example, to induce non-shivering thermogenesis in the brown adipose tissue of the subject. The cooling elements are anchored to the omentum and in contact with visceral tissues including visceral organs. The cooling elements have a temperature range from approximately 4° C. to approximately 37° C. to achieve a visceral tissue temperature ranging approximately 24° C. to approximately 35° C. to induce non-shivering thermogenesis in brown adipose tissue of the subject. The multiple cooling elements anchored to the omentum and in contact with visceral tissues can achieve an intra-abdominal regional hypothermia ranging from mild (32-36° C.) to moderate (24-32° C.) temperatures. The device further includes a programmable controller for adaptive programming dependent upon the level of glucose sensed in the blood of the subject. The device further includes a digital processing unit operatively linked to the programmable controller. The device further includes a blood glucose sensor operatively linked to the programmable controller through the digital processing unit to sense the levels of glucose in the subject. The digital processing unit can also receive data regarding food consumed and can determine an estimate of calories ingested at specific times of the day and/or during the course of the day. The digital processing unit can provide programming to the programmable controller. Typically, the level of glucose measured in the blood will fluctuate depending upon when the measurement is taken relative to when the last meal was eaten. See; e.g., FIG. 2.

The device includes multiple internal cooling elements anchored to the omentum and in contact with and cooling visceral tissues to achieve an intra-abdominal regional hypothermia. The elements includes a sterile, biocompatible indwelling tube filled with a circulating fluid, e.g., water, and connected in a closed circuit system to a refrigeration unit. The indwelling tube is surgically implanted into the abdomen, anchored onto the internal omentum and in contact with the visceral tissues. The portion of the indwelling tube in direct contact with the visceral tissues is designed to provide increased surface contact with the tissues, either by fanning out into a series of smaller diameter tubes, e.g., capillaries, or by spreading out into a flattened portion of the tube. The surgically implanted indwelling tube includes a port attached to the skin through which inlet and outlet tubes protrude from the skin and are accessible for attachment to the refrigeration unit to complete the closed circuit cooling system. An example of a port attached to the skin and designed for transcutaneous insertion of a tube is described in Nyman, et al., *J. Vasc. Interventional Biol.*, 20: 500-505, 2009, which is incorporated herein by reference. The device is designed to be ambulatory and includes a Peltier-driven portable refrigeration unit incorporated into a backpack or fanny pack. See, e.g., U.S. Patent Application 2009/0139248, which is incorporated herein by reference. The portable backpack refrigeration unit is powered by conversion of mechanical energy generated by the motion of the subject to electrical energy, using an electricity-generating backpack. See, e.g., U.S. Patent Application 2009/0015022, which is incorporated herein by reference.

The device includes a programmable controller that controls the temperature and flow of the fluid circulating into and out of the indwelling tube. The programmable controller is integrated into the portable refrigeration unit and includes a user interface. The user interface includes a monitor and keypad for use in entering and receiving instructions, programming or other information.

The device includes a digital processing unit operably linked to the programmable controller and configured to receive information from a sensor, a timekeeping device, a user interface, or an outside operating source and process the information and using the processed information provide instruction to the programmable controller.

The digital processing unit is operationally linked to a sensor that can measure glucose in the blood of the subject. Glucose is measured using a standard glucose monitor, e.g., GlucoMON®2 wireless glucose meter (from Diabetech LP, Dallas, Tex.), which can wirelessly send data regarding the blood glucose levels to the digital processing unit. The subject can also manually input via a user interface information regarding the food types and estimated quantity consumed during the day. These data are used by the digital processing unit to estimate the subject's caloric intake. The digital processing unit uses the data regarding the blood glucose levels and the caloric intake to program the programmable controller to control the temperature and flow of the circulating water to induce non-shivering thermogenesis in brown adipose tissue of the subject. An increase in non-shivering thermogenesis leads to increased intake of glucose into the brown adipocytes for glucose metabolism, and removal of glucose from circulation of the subject.

The device operating under a programmable controller for cooling one or more tissues may control glucose levels in the subject using the glucose monitor as described above. The degree of cooling by the cooling element is modulated by the programmable controller accordingly in response to the glucose monitor and instructions from the digital processing unit. In addition, the intake of glucose into metabolically active brown adipose tissue can be confirmed at certain time points, for example monthly, during a programmed cooling period, using the radioactive tracer $^{18}$F-fluorodeoxyglucose and positron emission tomography (PET) combined with computed tomography (CT) scanning. For analysis, the subject is injected with a bolus of $^{18}$F-fluorodeoxyglucose and subjected to PET-CT scanning. Cold-induced glucose uptake is monitored in brown adipose tissue of the supraclavicular tissue of the subject and observed as bright sections in the PET-CT scan. The larger the area of bright sections in the scan field, the greater the uptake of $^{18}$F-fluorodeoxyglucose into the tissue. See, e.g., Virtanen, et al., *N Engl. J. Med.*, 360: 1518-1525, 2009, which is incorporated herein by reference.

The use of additional medicaments in the treatment regimen is included in combination with application of the device described herein to further manage the levels of glucose in a human subject with diabetes. The health care provider can prescribe a twice daily injection of a glucagon-like peptide 1 (GLP-1) agonist, e.g., exenatide (Byetta®, Amylin Pharmaceuticals; San Diego, Calif./Eli Lilly; Indianapolis, Ind.), to further manage blood glucose levels in the subject. Exenatide slows adsorption of glucose from the gut, increases insulin secretion from the pancreas, lowers high levels of glucagon observed in subjects with diabetes after meals, and suppresses appetite. An alternative or additional treatment medicament includes oral treatment with rosiglitazone (Avandia®, GlaxoSmithKline), an insulin sensitizer that works by binding to the peroxisome proliferator-activated receptor (PPAR) in adipocytes and making the cells more responsive to insulin.

Example 5

Device for Treating Diabetes in a Human Subject Including Internal Cooling Elements Contacting Hypothalamus A device is described that includes cooling elements operating under a programmable controller for cooling an area of the body of a human subject to stimulate activity and/or proliferation of brown adipose tissue to treat a metabolic disorder, e.g., diabetes, in the human subject. The device includes an implantable cooling element placed into the preoptic area (POA) of the hypothalamus to induce non-shivering thermogenesis in brown adipose tissue of the subject. Direct cooling of the local environment of the POA evokes activation and thermogenesis in brown adipose tissue. See, e.g., Morrison, et al., *Exp. Physiol.*, 93: 773-797, 2008. The cooling element includes a Peltier element to controllably cool the hypothalamus. The Peltier element can achieve temperatures ranging from approximately 0° C. to approximately 37° C. to achieve a hypothalamus tissue temperature ranging from approximately 24° C. to approximately 36° C. to induce non-shivering thermogenesis in brown adipose tissue of the subject. The device further includes a programmable controller configured for adaptive programming. The programmable controller is incorporated into a wrist watch-like accessory worn by the subject and provides wireless control of the Peltier cooling element. The device further includes a digital processing unit operably linked to the programmable controller. The digital processing unit is also in communication with a glucose sensor for measuring the level of glucose in the blood of the subject. The device further includes an interface for manual or automatic input of information regarding the caloric intake at a certain time of day. The digital processing unit processes the data regarding current glucose levels and caloric intake in the subject and instructs the programmable controller to adjust the function of the cooling elements and to regulate the level of non-shivering thermogenesis in brown adipose tissue to provide control of blood glucose levels in the diabetic subject. See, e.g., FIG. 3.

The device includes an implantable cooling element for implantation into the hypothalamus of the subject. The implantable cooling element includes a Peltier element, a fine thermocouple probe, and a heat sink as described by Fujioka, et al., *Neurosci. Res.* 66: 402-405, 2010, which is incorporated herein by reference. A chip-sized Peltier element measuring approximately 6 mm by 6 mm (from, e.g., Ferrotec, Bedford, N.H.) is combined with a fine thermocouple probe (from, e.g., Physitemp Instruments, Inc., Clifton, N.J.) and a copper heat sink. This portion of the cooling element is covered with a fine layer of medical silicone or other biocompatible membrane. This portion of the cooling element is implanted into the hypothalamus using defined stereotactic parameters and a CT scan to assess proper positioning. See, e.g., Schoenen, et al., *Brain*, 128: 940-947, which is incorporated herein by reference. The copper heat sink is positioned on the heat dissipating side of the Peltier element and the heat from the heat sink is transferred to a circulating fluid that is part of a microchannel cooling system flowing between the implanted portion of the cooling element and a location adjacent to an exterior surface of the subject at the nape of the neck, e.g., adjacent to an epidermal surface or subcutaneous surface. Internal heat transferred from the Peltier element into the circulating fluid is transferred to the external ambient environment through a series of tubes associated with the microchannel cooling system. The thermocouple is used to measure the temperature of the hypothalamus tissue as it is being cooled and can be included in a closed loop system to modulate the activity of the Peltier element to maintain a desired tissue temperature. See, e.g., Osorio et al., *Medicon 2007, IFMBE Proceedings* 16: 911-914, 2007, which is incorporated herein by reference.

The programmable controller and digital processing unit of the device are located exterior to the subject and are incorporated into a dedicated-use handheld unit. The digital processing unit receives and processes information regarding physiological conditions from the sensors, determines whether additional cooling is required and instructs the programmable controller. The digital processing unit and/or programmable controller function in the absence of user input, but may also include a user interface allowing for input and receipt of data, programming, or other information. The user interface includes a key pad as well as a display screen for entering data. The digital processing unit receives information from the glucose sensor via wireless radio frequency and may employ bluetooth technology. The programmable controller communicates with the Peltier element via wireless radio frequency.

The digital processing unit is in communication with an implantable glucose sensor capable of sensing the subject's blood glucose levels. The subject is equipped with a biocompatible glucose sensor chip implanted into the abdomen or back of the upper arm of the subject, such as the sensor forming part of the Freestyle Navigator® glucose monitor. See, e.g., Abbot Diabetes Care, Alameda, Calif. The Freestyle Navigator® glucose monitor is capable of taking glucose measurements on a continuous basis, e.g., once every minute, and can communicate with an external receiver. The external receiver is included in the digital processing unit. The digitized output data stream from the sensor is stored and processed by the digital processing unit.

The human subject uses a food diary incorporated into the handheld unit to enter data regarding the type and quantity of food consumed during the course of the day. The handheld unit includes memory for storing a database containing information regarding calories and carbohydrate content of various foods, and the digital processing unit includes a computational algorithm designed to estimate caloric intake as well as carbohydrate intake based on these input data. Postprandial blood glucose levels reflect the amount of carbohydrates consumed by the subject. This information is processed by the digital processing unit, which provides instructions and programming to the programmable controller for adjusting the cooling function of the device including the Peltier element. The programmable controller adjusts the amount of cooling delivered to the hypothalamus as instructed by the digital processing unit based on the blood glucose levels and the caloric intake and content. Additional medicaments can also be included in the treatment regimen including medicaments specific for treating Type 1 and Type 2, e.g., insulin, a secretagogue, an insulin sensitizer, thiazolidinedione, an α-glucosidase inhibitor, a glucagon-like peptide analog, a dipeptidyl peptidase-4 inhibitor, an amylin analogue, or combinations thereof.

Example 6

Device for Treating Obesity in a Human Subject, Including Internal Cooling Elements Utilizing an Endothermal Chemical Composition Contacting Colon Tissue

A device is described that includes cooling elements operating under a programmable controller for cooling an area of the body of a human subject to modulate an activity of brown adipose tissue and thereby treat a metabolic disorder, e.g., obesity, in the human subject. The device includes a cooling element that uses an endothermal chemical composition. The portion of the device that includes the cooling element is inserted into the colon to facilitate cooling of thermoresponsive tissue within the colon. The cooling elements are designed to present a temperature range from approximately 4° C. to approximately 37° C. to achieve a colon tissue temperature ranging from approximately 24° C. to approximately 32° C. to induce non-shivering thermogenesis in brown adipose tissue of the subject. The device further includes an external, wrist-mounted programmable controller configured for adaptive programming. The wrist-mounted programmable controller includes a digital processing unit and a glucose sensor, as well as a monitor for caloric intake and caloric expenditure during the course of the day. The wrist-mounted programmable controller is in wireless communication with the cooling element inserted into the colon. See, e.g., FIG. 4.

The device includes an implantable portion configured for placement into the colon, with a cooling element containing an endothermal chemical composition. The implantable portion of the device resembles a self-expanding stent for insertion into the lower colon. See, e.g., U.S. Pat. Nos. 5,876,445; 7,105,175; U.S. Patent Applications 2009/0081271, each of which is incorporated herein by reference. The implantable portion of the device includes two sets of micro-reservoirs, each containing a distinct endothermic chemical, citric acid or sodium bicarbonate, which upon mixing draws heat from the surrounding environment resulting in cooling. The micro-reservoirs are incorporated into the wall of the stent-like structure. Examples of implantable stents with at least two reservoirs are described in U.S. Patent Applications 2009/0319026 and 2009/0149947, which is incorporated herein by reference. Each micro-reservoir containing either citric acid or sodium bicarbonate is covered with a gold foil that, in the presence of a triggering event such as a voltage, dissolves and releases the contents of the micro-reservoir. See, e.g., Grayson, et al., *Proc. IEEE*, 92: 6-21, 2004, which is incorporated herein by reference. Citric acid and sodium bicarbonate released from the micro-reservoirs mix in a common chamber creating an endothermic reaction. The common chamber is in direct contact with the luminal surface of the colon allowing for localized cooling. The common chamber also includes a semi-permeable diffusion membrane through which the byproducts of the endothermic reaction can diffuse out of the chamber and into the lumen of the colon. Application of voltage to the microreservoirs containing the endothermal chemical composition is triggered wirelessly by the wrist-mounted programmable controller.

The implantable portion of the device including micro-reservoirs containing an endothermal chemical composition is inserted into the colon using standard methods for colonic stenting. See, e.g., Piccinni, et al., *World J. Gastroenterol.*, 10: 758-764, 2004, which is incorporated herein by reference. The subject undergoes one or more colonic enemas to cleanse the colon prior to placement of the device. The subject is placed in a supine position and is administered one or more sedatives and/or analgesics commonly used for colonoscopy. The stent-like implantable portion of the device is deployed along a guide wire using fluoroscopic and endoscopic guidance. Endoscopic and/or x-ray images are used to assess proper placement of the implantable portion of the device.

The device further includes a wrist-mounted programmable controller that can send wireless instructions to the portion of the device implanted in the colon. The wrist-mounted programmable controller includes a user interface with a keypad and LCD screen for inputting and receiving data. The wrist-mounted programmable controller includes a digital programming unit operationally linked to and capable of receiving information from sensors that can detect glucose and fatty acids in the blood of the subject. The glucose and fatty acid sensors are incorporated into the underside of the wrist-mounted programmable controller and are in direct contact with the skin of the subject. A number of examples of wrist-mounted sensors for sensing analytes in the blood, including glucose and fatty acids, have been described. See, e.g., U.S. Pat. Nos. 4,953,552; 5,551,953; 5,752,512; 6,151,517, each of which is incorporated herein by reference.

The user interface of the wrist-mounted programmable controller can receive input data regarding type and quantity of food consumed by the subject during the course of the day. The data entered by the subject into the food diary is used to estimate the caloric intake. The wrist-mounted programmable controller also includes activity sensors, operationally linked to the digital processing unit, for sensing the activity of the subject. Such sensors sense heart rate, body temperature, skin resistance, motion/acceleration, and velocity. See, e.g., U.S. Pat. No. 4,312,358, which is incorporated herein by reference. Data from the sensors are processed by the digital processing unit to estimate the calories burned during the course of the day. The digital processing unit of the wrist-mounted programmable controller processes the data regarding the blood glucose and fatty acid levels, caloric intake, and estimated caloric expenditure and based on the outcome provides one or more instructions for the programmable controller to wirelessly control the release of the endothermic chemicals from the micro-reservoirs in the implantable portion of the device to control cooling of the thermoresponsive tissue of the subject.

The subject's weight is monitored on a daily basis using a standard bathroom scale. The amount of weight lost is manually entered into the wrist-mounted programmable controller. Alternatively, the bathroom scale can be fitted with a wireless transmitter that automatically transmits information regarding weight to the wrist-mounted programmable controller. By processing the data acquired regarding the rate of weight loss over the course of days and/or weeks as well as the daily caloric intake and physical activity data, the digital processing unit provides instruction to the wrist-mounted programmable controller, which adjusts the frequency of the release of the two endothermic chemicals in the implantable portion of the device.

The medicament rosiglitazone (Avandia®, GlaxoSmithKline, Inc.) is included in the treatment regimen to the augment brown adipose tissue mediated non-shivering thermogenesis treatment. The medicament rosiglitazone has been shown to increase the expression of uncoupling protein 1 (UCP-1) in brown adipocytes. See, e.g., Teruel, et al., *J. Biol. Chem.*, 278: 263-269, 2003, which is incorporated herein by reference. Rosiglitazone is dosed orally once or twice daily with a total daily dose ranging from 4 to 8 mg.

To further augment the brown adipose tissue-mediated non-shivering thermogenesis, an infusion pump containing norepinephrine, an activator of brown adipocyte activity, is implanted into or in close proximity to the brown adipose tissue depots in the supraclavicular region of the subject. The infusion pump can periodically release minute, localized amounts of norepinephrine to stimulate the activity of the brown adipocytes. An example of an implantable infusion pump is the SynchroMed® II Pump (from Medtronic, Minneapolis, Minn.). The use of an infusion pump for administering norepinephrine/noradrenaline to a subject is described in Nagasaka, *J. Appl. Physiol.*, 32: 199-202, 1972, which is incorporated herein by reference.

The use of additional medicaments is included in the treatment regimen in combination with the device described herein to further manage weight loss in an obese subject. The subject can choose to include an over-the-counter weight loss pill, e.g., orlistat (Alli®, GlaxoSmithKline, Inc.), in his or her treatment regimen.

Example 7

Device Including Passive Cooling Elements Contacting a Great Vein for Treating Metabolic Syndrome in a Human Subject A device is described that includes cooling elements operating under a programmable controller for cooling an area of the body of a human subject to modulate an activity of brown adipose tissue and thereby treat a metabolic disorder, e.g., metabolic syndrome, in the human subject. The device acts by lowering circulating glucose levels and stimulating weight loss through induction of non-shivering thermogenesis in brown adipose tissue of the subject. The device includes a cooling element to apply a cooling temperature to thermoresponsive tissue in a great vein, e.g., the pulmonary vein, of the subject. The cooling element is a passive cooling system that can controllably cool pulmonary vein thermoreceptors with little or no energy input. The passive cooling system is implanted into the subject and includes a deep portion and a shallow portion. The deep portion of the passive cooling system is in close proximity to or in direct contact with the pulmonary vein. The shallow portion of the passive cooling system is implanted just below the surface of the subject's skin and participates in passive heat transfer with the ambient environment. The passive cooling system can achieve temperatures ranging from approximately 0° C. to approximately 37° C. to achieve a pulmonary vein temperature of approximately 32° C. to induce non-shivering thermogenesis in the subject. The device further includes a programmable controller incorporated into the arm rest of a subject's wheel chair and configured for adaptive programming. The programmable controller includes a digital processing unit in communication with sensors that can measure physiological indicators specific to metabolic syndrome including levels of glucose and cholesterol, and blood pressure. See, e.g., FIG. 5.

The device described herein includes a passive cooling system including a deep portion and a shallow portion able to cool pulmonary vein thermoreceptors to induce non-shivering thermogenesis in brown adipose tissue of the subject with minimal energy input to the device. The passive cooling system includes a series of tubes and a low-energy pump that can circulate a fluid, e.g., water in a closed loop through the deep and shallow portions of the system. The deep portion of the passive cooling system is implanted in close proximity to or in direct contact with the pulmonary vein. The shallow portion of the passive cooling system is implanted just below the surface of the skin where the temperature of the subject is closer to ambient temperature, and heat exchange with the external environment is possible. The shallow portion of the passive cooling system is configured in a tentacle-like structure, allowing the fluid to be spread out over a larger surface area to encourage more rapid cooling or equilibrium with the outside environment. The internal body temperature at the site of the deep portion of the passive cooling system is approximately 37° C., whereas the skin temperature is approximately 32° C. or cooler depending upon the ambient temperature. The fluid in the passive cooling system is pumped from the relatively cooler environment of the shallow portion to the relatively warmer environment of the deep portion of the device. The cooling capacity of the shallow portion of the passive cooling device can be increased by application of cold packs to the surface of the skin overlaying the shallow portion of the implanted passive cooling system. The pump for circulating the fluid through the implanted passive cooling system is powered by a body heat energy generator incorporated into the implanted portion of the device. See, e.g., U.S. Pat. No. 6,075,199, which is incorporated herein by reference.

The device further includes an external programmable controller mounted into the armrest of the subject's wheelchair and configured to send wireless instructions to the implanted passive cooling system. The armrest-mounted programmable controller includes a user interface with a keypad and LCD screen for inputting data, programming instructions, and other information. The digital processing unit of the armrest-mounted programmable controller can receive data regarding the subject's blood levels of glucose, fatty acids, and cholesterol, all indicators of metabolic syndrome. Blood glucose levels are measured using an implantable glucose sensor such as described in U.S. Pat. No. 7,577,470, which is incorporated herein by reference. The implanted glucose sensor is in wireless communication with the armrest-mounted programmable controller. The blood levels of fatty acids and cholesterol are measured using standard clinical assays as part of a medical visit, and the data is either entered manually or via wireless communication from an outside computing device into the armrest-mounted programmable controller. Blood pressure is measured using a form of wrist-mounted blood pressure monitor associated with the armrest of the wheelchair. Commercial examples of wrist mounted blood pressure measuring devices have been described. See, e.g., Vasotrac® Blood Pressure Monitor, from Medwave, Arden Hills, Minn.; Omron® Wrist Blood Pressure Monitor, from Omron Global, Schaumburg, Ill.

The armrest-mounted programmable controller and its digital processing unit further include the capability of collecting data regarding caloric intake and caloric expenditure. Caloric intake is estimated from the type and quantity of food ingested by the subject during the course of the day. Data regarding the type and quantity of food is manually entered into the armrest-mounted programmable controller or is communicated wirelessly from an outside computing device and/or outside sensing device. The outside sensing device can include a nonphysiologic sensor, for example, an electronic food detector that can determine mass, volume, or weight of foodstuff to be eaten by the subject and can measure and quantitate caloric content and nutritional content of foodstuff that will be eaten by the subject. Data or other information from the electronic food detector can be communicated to the digital processing unit or the programmable controller. See, e.g., U.S. Patent Application 2010/0125420; 2010/0125419; U.S. 2010/0125418; U.S. 2010/0125417; each of which is incorporated herein by reference. If a wheelupholstery-bound subject experiences little or no physical activity, the caloric expenditure over a 24 hour period may closely match the resting metabolic rate of the subject. The resting metabolic rate of the subject is estimated based on parameters of gender, height, weight, age, temperature, muscular activity, ventilation capacity, caloric intake, drugs, hormones and emotional state entered into the programmable controller using the user interface. See, e.g., Lyznicki, et al., *Am. Fam. Physician,* 63: 2185-2196, 2001, which is incorporated herein by reference.

By definition, a subject with metabolic syndrome is overweight, especially in and around the abdomen, and exhibits multiple traits that can include elevated glucose levels, insulin resistance, elevated serum triglycerides, decreased HDL cholesterol, and elevated blood pressure. The digital processing unit processes data from periodic monitoring of these physiological conditions and their indicators, including and comparing the data to baseline values and to values from normal individuals, and provides instruction to the armrest-mounted programmable controller. The armrest-mounted programmable controller wirelessly modulates the action of the pump associated with the implanted passive cooling system to control the temperature of the fluid reaching the deep portion of the system. The action of the pump is adjusted in response to wireless instructions from the armrest-mounted programmable controller. Delivery of more or less cooling to the pulmonary vein thermoreceptors modulates the metabolic activity of the brown adipose tissue, resulting in increased or decreased levels of non-shivering thermogenesis; net increases in non-shivering thermogenesis serve to lower glucose levels and stimulate weight loss in the subject. In the long term, continued exposure to cold increases the mass of the brown adipose tissue. Increases in mass of the brown adipose tissue in response to long term cooling are monitored using $^{18}$F-fluorodeoxyglucose metabolic labeling and PET-CT scanning. See, e.g., Klingenspor, *Exp. Physiol.* 88: 141-148, 2003; van Marken Lichtenbelt, et al., *N. Eng., J. Med.,* 360: 1500-1508, 2009, each of which is incorporated herein by reference.

Additional medicaments are optionally included in the subject's treatment regimen and can include medicaments specifically designed to treat one or more conditions associated with metabolic syndrome, e.g., one or more of insulin, secretagogue, insulin sensitizer, thiazolidinedione, α-glucosidase inhibitor, glucagon-like peptide analog, dipeptidyl peptidase-4 inhibitor, amylin analogue, or combinations thereof; to treat high cholesterol, e.g., one or more of a statin, cholesterol absorption inhibitor, bile acid sequestrant, fibrates, niacin, or combinations thereof; to treat high blood pressure, e.g., one or more of a diuretic, beta blocker, ACE inhibitor, angiotensin II receptor blocker, calcium channel blocker, alpha blocker, vasodilator, or combinations thereof. The combination of medicaments prescribed by the subject's health care provider is dependent upon which aspects of metabolic syndrome are experienced by the subject.

Each recited range includes all combinations and sub-combinations of ranges, as well as specific numerals contained therein.

All publications and patent applications cited in this specification are herein incorporated by reference to the extent not inconsistent with the description herein and for all purposes as if each individual publication or patent application were specifically and individually indicated to be incorporated by reference for all purposes.

Those having ordinary skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having ordinary skill in the art will recognize that there are various vehicles by which processes and/or systems and/or other technologies disclosed herein can be effected (e.g., hardware, software, and/or firmware), and that the preferred vehicle will vary with the context in which the processes and/or systems and/or other technologies are deployed. For example, if a surgeon determines that speed and accuracy are paramount, the surgeon may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies disclosed herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those having ordinary skill in the art will recognize that optical aspects of implementations will typically employ optically-oriented hardware, software, and or firmware.

In a general sense the various aspects disclosed herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices disclosed herein, or a microdigital processing unit configured by a computer program which at least partially carries out processes and/or devices disclosed herein), electrical circuitry forming a memory device (e.g., forms of random access memory), and/or electrical circuitry forming a communications device (e.g., a modem, communications switch, or optical-electrical equipment). The subject matter disclosed herein may be implemented in an analog or digital fashion or some combination thereof.

At least a portion of the devices and/or processes described herein can be integrated into a data processing system. A data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

The herein described components (e.g., steps), devices, and objects and the description accompanying them are used as examples for the sake of conceptual clarity and that various configuration modifications using the disclosure provided herein are within the skill of those in the art. Consequently, as used herein, the specific examples set forth and the accompanying description are intended to be representative of their more general classes. In general, use of any specific example herein is also intended to be representative of its class, and the non-inclusion of such specific components (e.g., steps), devices, and objects herein should not be taken as indicating that limitation is desired.

With respect to the use of substantially any plural or singular terms herein, the reader can translate from the plural to the singular or from the singular to the plural as is appropriate to the context or application. The various singular/plural permutations are not expressly set forth herein for sake of clarity.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable or physically interacting components or wirelessly interactable or wirelessly interacting components or logically interacting or logically interactable components.

While particular aspects of the present subject matter described herein have been shown and described, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an"; the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, or A, B, and C together, etc.). Virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method for modulating an activity of a brown adipose tissue in a vertebrate subject comprising:
inducing non-shivering thermogenesis in brown adipose tissue by applying cooling to one or more tissues of the vertebrate subject with one or more cooling elements, wherein the one or more cooling elements are configured to lower the temperature of the one or more tissues and thereby induce non-shivering thermogenesis in the brown adipose tissue of the vertebrate subject, wherein at least a portion of the one or more cooling elements is implanted into the one or more tissues,
and controlling the one or more cooling elements with a programmable controller configured to provide instructions to the one or more cooling elements in response to information regarding one or more physiological conditions of the vertebrate subject, the one or more physiological conditions of the vertebrate subject including a plasma level of one or more metabolic analytes.

2. The method of claim 1, further comprising sensing with one or more sensors the information regarding the one or more physiological conditions and communicating the information from the one or more sensors to the programmable controller.

3. The method of claim 1, further comprising sensing with one or more sensors the information regarding the one or more physiological conditions and communicating the information from the one or more sensors to a digital processing unit, processing the information with the digital processing unit into at least one resulting instruction, and providing by the digital processing unit the at least one resulting instruction to the programmable controller.

4. The method of claim 3, wherein processing the information with the digital processing unit includes comparing the information regarding the one or more physiological conditions to information of a standard value or preprogrammed value.

5. The method of claim 1, further comprising receiving the information regarding the one or more physiological conditions from an outside operating source to a receiver including at least one of the programmable controller or a digital processing unit.

6. The method of claim 5, wherein the outside operating source includes a computing device or a human operator.

7. The method of claim 1, wherein the information regarding the one or more physiological conditions includes a sugar level or a fatty acid level in the vertebrate subject.

8. The method of claim 1, further comprising implanting the programmable controller in the vertebrate subject.

9. The method of claim 8, further comprising implanting the programmable controller within a lumen of the vertebrate subject.

10. The method of claim 1, further comprising implanting at least a portion of one or more cooling elements within a lumen of the vertebrate subject.

11. The method of claim 10, further comprising implanting the at least a portion of one or more cooling elements within a circulatory vessel of the vertebrate subject.

12. The method of claim 10, further comprising implanting the at least a portion of one or more cooling elements within a colon or a large intestine of the vertebrate subject.

13. The method of claim 1, wherein the one or more tissues include thermoresponsive tissue of the vertebrate subject.

14. The method of claim 1, wherein the one or more tissues include nervous tissue of the vertebrate subject.

15. The method of claim 1, wherein the one or more tissues include a cutaneous tissue of the vertebrate subject.

16. The method of claim 1, wherein the one or more tissues include brown adipose tissue.

17. The method of claim 1, wherein the one or more tissues include tissue in a core of the body of the vertebrate subject.

18. The method of claim 1, wherein the one or more tissues includes one or more blood vessels or lymph vessels.

19. The method of claim 1, wherein the one or more cooling elements are configured to cool by electrical cooling activity.

20. The method of claim 19, wherein the one or more cooling elements are configured to cool by Peltier cooling activity.

21. The method of claim 19, wherein the one or more cooling elements are configured to cool by heat pumps.

22. The method of claim 21, wherein the one or more heat pumps are configured to transfer heat to one or more tissues including blood or skin of the vertebrate subject.

23. The method of claim 1, wherein the one or more cooling elements are configured to cool by one or more implantable deep tissue heat-extracting components in combination with one or more surface tissue heat-releasing components.

24. The method of claim 1, wherein the one or more cooling elements are configured to cool by chemical cooling activity.

25. The method of claim 1, wherein the one or more cooling elements include one or more of nanoparticles, microparticles, paramagnetic particles, magnetic particles, or chemical core particles.

26. The method of claim 25, wherein the one or more chemical core particles include endothermal chemical reactants.

27. The method of claim 1, further comprising injecting the implantable portion of the one or more cooling elements.

28. The method of claim 1, wherein the one or more implantable cooling elements include one or more endothermic biodegradable particles.

29. The method of claim 28, wherein the one or more endothermic biodegradable particles include one or more solid ice ($H_2O$) particles.

30. The method of claim 1, further comprising cooling the tissue with the one or more implantable cooling elements to attain a tissue temperature from approximately 4° C. to approximately 36° C.

31. The method of claim 1, further comprising cooling the tissue with the one or more implantable cooling elements to attain a tissue temperature from approximately 12° C. to approximately 20° C.

32. The method of claim 1, further comprising cooling the tissue with the one or more implantable cooling elements to attain a tissue temperature from approximately 24° C. to approximately 32° C.

33. The method of claim 1, further comprising cooling the tissue with the one or more implantable cooling elements to attain a tissue temperature approximately 16° C. or lower.

34. The method of claim 1, wherein the programmable controller is incorporated in clothing, bedding, furniture, or upholstery.

35. The method of claim 1, further comprising powering the one or more cooling elements and programmable controller with a power source.

36. The method of claim 35, wherein the power source includes stored power, a battery, a fuel cell, or beamed power.

37. The method of claim 1, wherein the vertebrate subject is undergoing treatment for at least one of weight loss, diabetes, obesity, metabolic syndrome, dyslipidemia, or hypercholesterolemia.

38. The method of claim 1 further comprising applying one or more medicaments for treatment of weight loss, metabolic disorder, diabetes, obesity, metabolic syndrome, dyslipidemia, or hypercholesterolemia, to the one or more tissues in combination with the one or more cooling elements of the device.

39. The method of claim 38, wherein the one or more medicaments include one or more of β-adrenergic receptor agonist, NPY antagonist, leptin, UCP activating agent, thyroxine, serotonin reuptake inhibitor, MCH antagonist, GLP-1 agonist, 5-$HT_{2C}$ agonist, 5-$HT_{2A}$ agonist, galanin antagonist, CRF agonist, urocortin agonist, melanocortin agonist or enterostatin agonist.

40. The method of claim 1, further comprising applying neurostimulation with a neurostimulator to the one or more tissues.

41. The method of claim 1, further comprising applying neurostimualtion with a neurostimulator to one or more second tissues other than the one or more tissues.

42. The method of claim 41, wherein the one or more other tissues include nerve tissue.

43. The method of claim 41, wherein the neurostimulator is one of an electric neurostimulator, magnetic neurostimulator, ultrasonic neurostimulator, or microwave neurostimulator.

44. A method for inducing weight loss in a vertebrate subject:
inducing non-shivering thermogenesis in brown adipose tissue by applying cooling to one or more tissues of the vertebrate subject with one or more cooling elements, wherein the one or more cooling elements are configured to lower the temperature of the one or more tissues and thereby induce non-shivering thermogenesis in the brown adipose tissue of the vertebrate subject, wherein at least a portion of the one or more cooling elements is implanted into the one or more tissues,
and controlling the one or more cooling elements with a programmable controller configured to provide instructions to the one or more cooling elements in response to information regarding one or more physiological conditions of the vertebrate subject, the one or more physiological conditions of the vertebrate subject including a glucose level.

45. The method of claim 44, further comprising sensing with one or more sensors the information regarding the one or more physiological conditions and communicating the information from the one or more sensors to the programmable controller.

46. The method of claim 44, further comprising sensing with one or more sensors the information regarding the one or more physiological conditions and communicating the information from the one or more sensors to a digital processing unit, processing the information with the digital processing unit into at least one resulting instruction, and providing by the digital processing unit the at least one resulting instruction to the programmable controller.

47. The method of claim 46, wherein processing the information with the digital processing unit includes comparing the information regarding the one or more physiological conditions to information of a standard value or preprogrammed value.

48. The method of claim 44, further comprising receiving the information regarding the one or more physiological conditions from an outside operating source to a receiver including at least one of the programmable controller or a digital processing unit.

* * * * *